(12) United States Patent
Barth et al.

(10) Patent No.: US 10,030,010 B2
(45) Date of Patent: Jul. 24, 2018

(54) ROUTE OF SYNTHESIS FOR THE PREPARATION OF SUVOREXANT

(71) Applicant: Sandoz AG, Basel (CH)

(72) Inventors: Roland Barth, Kundl (AT); Kathrin Höferl-Prantz, Kundl (AT); Frank Richter, Kundl (AT); Gerhard Widschwenter, Kundl (AT)

(73) Assignee: Sandoz AG (CH)

( * ) Notice: Subject to any disclaimer, the term of this patent is extended or adjusted under 35 U.S.C. 154(b) by 0 days.

(21) Appl. No.: 15/501,295

(22) PCT Filed: Aug. 4, 2015

(86) PCT No.: PCT/EP2015/067995
§ 371 (c)(1),
(2) Date: Feb. 2, 2017

(87) PCT Pub. No.: WO2016/020405
PCT Pub. Date: Feb. 11, 2016

(65) Prior Publication Data
US 2017/0217947 A1    Aug. 3, 2017

(30) Foreign Application Priority Data
Aug. 4, 2014    (EP) .................................. 14179727

(51) Int. Cl.
| | |
|---|---|
| *C07D 243/08* | (2006.01) |
| *C07D 403/10* | (2006.01) |
| *C07D 413/14* | (2006.01) |
| *C07D 249/06* | (2006.01) |

(52) U.S. Cl.
CPC .......... *C07D 413/14* (2013.01); *C07D 243/08* (2013.01); *C07D 249/06* (2013.01); *C07D 403/10* (2013.01)

(58) Field of Classification Search
CPC ... C07D 243/08; C07D 403/10; C07D 413/14

USPC .................................................. 540/492, 575
See application file for complete search history.

(56) References Cited

U.S. PATENT DOCUMENTS

2007/0249589 A1    10/2007    Aebi et al.

FOREIGN PATENT DOCUMENTS

| | | |
|---|---|---|
| DE | 2628347 A1 | 1/1978 |
| WO | 2004024720 A1 | 3/2004 |
| WO | 2008033764 A2 | 3/2008 |
| WO | 2008069997 A1 | 6/2008 |
| WO | 2012148553 A1 | 11/2012 |
| WO | 2013007371 A2 | 1/2013 |
| WO | 2013169610 A1 | 11/2013 |

OTHER PUBLICATIONS

International Search Report and Written Opinion for PCT/ EP2015/ 067995, dated Nov. 2, 2016, 14 pages.
Wuts, Peter G.M, et al., Greene's Protective Groups in Organic Synthesis, Fourth Edition, John Wiley & Sons, Inc., 2007, Chapter 7.

*Primary Examiner* — Brenda L Coleman
(74) *Attorney, Agent, or Firm* — Luedeka Neely Group, P.C.

(57) ABSTRACT

The present invention relates to a process for the preparation of a compound of formula (A), Further, the present invention relates to the respective compound (A) as such and to its use in the preparation of antifungal agent.

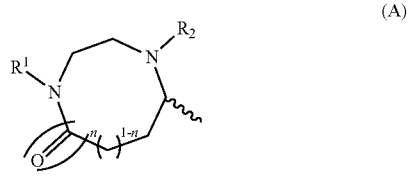

16 Claims, 7 Drawing Sheets

ROUTE OF SYNTHESIS FOR THE PREPARATION OF SUVOREXANT

This application is a Section 371 national phase entry of PCT application PCT/EP2015/067995, filed Aug. 4, 2015. This application also claims the benefit of the earlier filing date of European patent application 14179727.4, filed Aug. 4, 2014.

The present invention relates to a process for the preparation of a compound of formula (A)

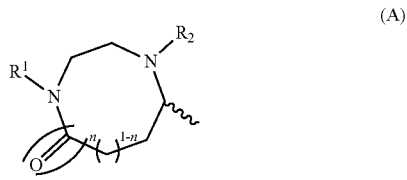

or a pharmaceutically acceptable salt or solvate thereof, to a compound (A) as such, as well as to a compound (A) obtained or obtainable by said process. Further, the present invention relates to processes for the preparation of intermediate compounds useful in the synthesis of the invention and the intermediate compounds as such.

BACKGROUND OF THE INVENTION

Orexin is a neurotransmitter that regulates wakefulness and appetite. Orexins are excitatory neuropeptides that have a critical role in maintaining wakefulness. Orexin receptors are found in the mammalian brain and may have numerous implications in pathologies such as depression; anxiety; addictions; obsessive compulsive disorder; affective neurosis; depressive neurosis; anxiety neurosis; dysthymic disorder; behavior disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinson's disease; Cushing's syndrome/disease; basophile adenoma; prolactinoma; hyperprolactinemia; hypophysis tumor/adenoma; hypothalamic diseases; inflammatory bowel disease; gastric dyskinesia; gastric ulcers; Froehlich's syndrome; adenohypophysis disease; hypophysis disease; adenohypophysis hypofunction; adenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardial infarction; ischemic or hemorrhagic stroke; subarachnoid hemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection, e.g. HIV, post-chemotherapy pain; post-stroke pain; post-operative pain; neuralgia; conditions associated with visceral pain such as irritable bowel syndrome, and angina; migraine; urinary bladder incontinence, e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general orexin system dysfunction.

Some orexin receptor antagonists are capable of influencing at least some of the above described pathological conditions. In particular, orexin receptor antagonists capable of promoting sleep in animals and humans are described in the art. One example for such an orexin receptor antagonist is [(7R)-4-(5-chloro-1,3-benzoxazol-2-yl)-7-methyl-1,4-diazepan-1-yl][5-methyl-2-(2H-1,2,3-triazol-2-yl)phenyl]methanone which has the structure according to Formula I

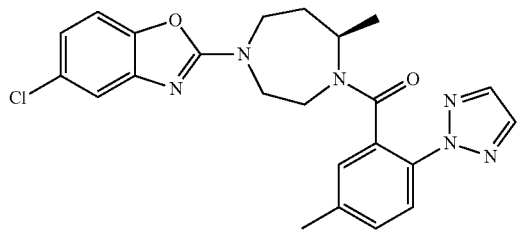 [SMILES: Cc1ccc(-n2nccn2)c(C(=O)N2CCN(c3nc4cc(Cl)ccc4o3)CC[C@H]2C)c1]

and which is, e.g., described in US 2008/0132490, WO 2008/069997 and Cox et al. (2010) *Journal of Medicinal Chemistry*, 53(14): 5320-5332. Alternative names for this compound are 5-chloro-2-{(5R)-5-methyl-4-[5-methyl-2-(2H-1,2,3-thiazol-2-yl)benzoyl]-1,4-diazepan-1-yl}-1,3-benzobenzoxazol and [(R)-4-(5-chloro-benzooxazol-2-yl)-7-methyl-[1,4]diazepan-1-yl]-(5-methyl-2-[1,2,3]triazol-2-yl-phenyl)-methanone.

The synthesis of [(7R)-4-(5-chloro-1,3-benzoxazol-2-yl)-7-methyl-1,4-diazepan-1-yl][5-methyl-2-(2H-1,2,3-triazol-2-yl)phenyl]methanone (herein also referred to as "Suvorexant" or "orexin receptor antagonist") is described in WO 2008/069997. There, a synthesis that is based on a chiral resolution by chiral HPLC (high performance liquid chromatography) is described. The first step of this synthesis involves a 1,4-addition of Boc-ethylenediamine to methyl vinylketone followed by a Cbz-protection of the free amine to give a Boc-protected intermediate. The Boc-protecting group is then cleaved with HCl and a 7-membered ring is closed by a reductive amination reaction sequence to give a racemic compound which after re-protection of the free amine with a Boc-protective group is resolved by preparative chiral HPLC. The resulting enantiomerically pure amine is then coupled with a triazole benzoic acid derivative under standard peptide coupling conditions. Hydrogenation cleaves the Cbz-protecting group and the resulting amine is then finally coupled with a benzoxazole derivative to give Suvorexant. However, in this linear sequence a large number of steps is needed to provide Suvorexant with only rather low yields. Further, the synthesis is disadvantageous in that a chiral resolution by preparative HPLC is needed, a process which is costly and thus not suitable for the preparative scale.

A further synthesis of Suvorexant is described in WO 2012/148553. This process patent discloses a different route towards Suvorexant. According to WO 2012/148553, chloroaminophenol is condensed with thiophosgene to give mercaptobenzoxazole which is then converted into a ketone by treatment with oxalyl chloride/DMF followed by a one-pot reaction with mono Boc-protected ethylenediamine and vinylketone. The Boc-protecting group is then cleaved to give an intermediate which is then cyclized by a transfer hydrogenation with a costly and very specific ruthenium catalyst to give an enantiomerically pure compound comprising a free amine group. The amine is then coupled with the acid chloride of a triazole benzoic acid derivative to give Suvorexant.

A stereoselective Suvorexant synthesis includes a tandem enantioselective transamination/ring formation and is described in WO2013/169610. The synthesis starts with the preparation of a mesylate under standard conditions which is then converted into an amine in the presence of a (R)-selective sitagliptin transaminase and the intermediately formed amine cyclizes to give the seven-membered diazepane ring. This step requires a strict control of process parameters to suppress the formation of an undesired impurity (regioisomer). Further, a very specific and sensitive enzyme needs to be employed which again renders the process disadvantageous for the preparative scale.

Thus, there is still the need for an improved synthesis of Suvorexant which provides Suvorexant in high yields and which overcomes the disadvantages of the processes described in the prior art, such as the use of costly and complex catalyst systems and sensitive enzymes.

SUMMARY OF THE INVENTION

Surprisingly, it was found that this object can be solved by a process for the preparation of a compound of formula (A)

(A)

or a pharmaceutically acceptable salt or solvate thereof, wherein (A) is preferably (A*)

(A*)

and wherein $R^1$ is selected from the group consisting of H, $PG^1$ and $R^A$ with $R^A$ being and wherein $R^2$ is selected from the group consisting of H, $PG^2$ and $R^B$ with $R^B$ being and wherein $PG^1$ and $PG^2$ are, independently of each other, suitable protecting groups, and wherein n is 0 or 1, the process comprising (a) providing a compound of formula (II)

(II)

wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, (b) reacting the compound of formula (II) with a base and optionally reducing the compound to give the compound of formula (A), preferably (A*).

Further, the present invention relates to a compound of formula (A)

(A)

or a pharmaceutically acceptable salt or solvate thereof, wherein (A) is preferably (A*)

wherein $R^1$ is selected from the group consisting of H, $PG^1$ and $R^A$ with $R^A$ being

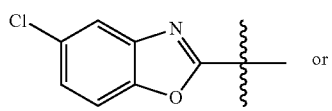 or

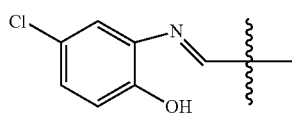

and wherein $R^2$ is selected from the group consisting of H, $PG^2$ and $R^B$ with $R^B$ being

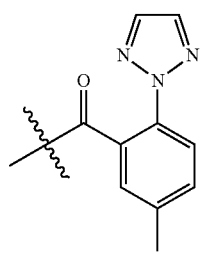 [SMILES: *C(=O)c1cc(C)ccc1-n1nccn1]

and wherein $PG^1$ and $PG^2$ are, independently of each other, suitable protecting groups, and wherein n is 0 or 1, and wherein in case n=0 and $R^1$ is $R^A$, $R^2$ is not $R^B$ or H or, wherein in case n=0 and $R^1$ is $R^A$, $R^B$ is $PG^1$ and wherein in case n=0 and $R^1$ is H, $R^2$ is not $R^B$ or, wherein in case n=0 and $R^1$ is H, $R^2$ is H or $PG^2$ and wherein in case n=0 and $R^1$ is Cbz $R^2$ is not H or Boc or $R^B$ and wherein when n=1 $R^1$ and $R^2$ are not both H.

Further, the present invention also relates to a compound (IX)

(IX)

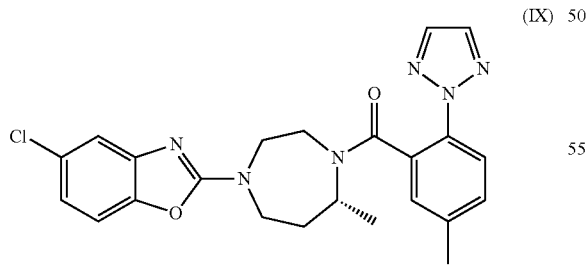

obtained or obtainable by the above described method, wherein the compound comprises less than 5% by weight, more preferably less than 2% by weight, more preferably less than 1% by weight, more preferably less than 100 ppm, of the regio-isomeric side product (IX-S) as impurity (IX-S)

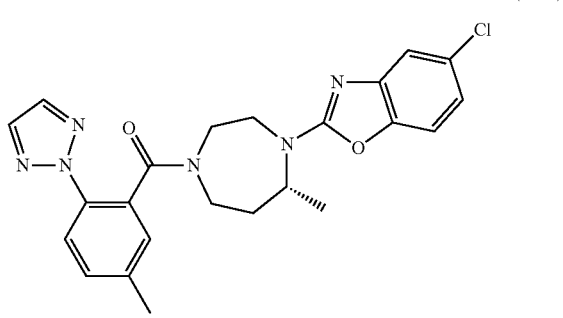

based on the total weight of the compound (IX), which includes the compound (IX-S). Preferably, the compound (IX) does not comprise the region-isomeric compound (IX-S) as impurity.

Further, the present invention relates to the use of a compound of formula (A), or (A*), as described above, for the preparation of a compound of formula (IX)

(IX)

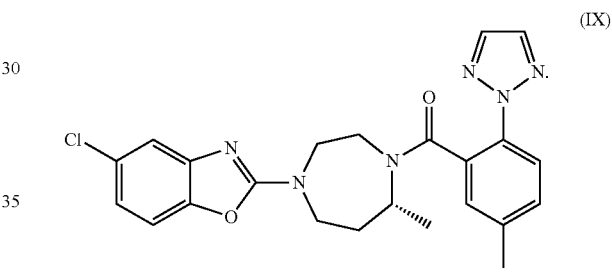

Further, the present invention relates to crystalline compound of formula (VIIb-H), preferably of formula (VIIb*-H) and salts, preferably crystalline salt thereof.

Further, the present invention relates to crystalline form (A) of compound (VIIb-H), to crystalline form (I) of compound (VIIb*-H), to crystalline form (I-S) of the sulphate salt of compound (VIIb*-H) and to crystalline form (I-Cl) of the hydrochloride salt of compound (VIIb*-H), all as disclosed herein below.

DETAILED DESCRIPTION

The process for the preparation of a compound of formula (A)

(A)

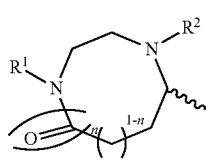

or a pharmaceutically acceptable salt or solvate thereof, wherein (A) is preferably (A*)

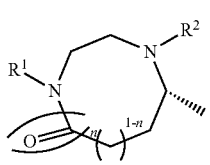
(A*)

and wherein $R^1$ is selected from the group consisting of H, $PG^1$ and $R^A$ with $R^A$ being

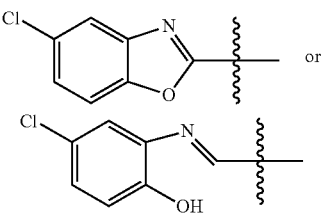
or and wherein $R^2$ is selected from the group consisting of H, $PG^2$ and $R^B$ with $R^B$ being

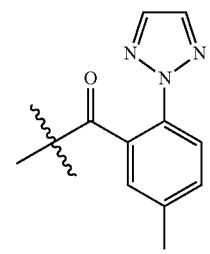

and wherein $PG^1$ and $PG^2$ are, independently of each other, suitable protecting groups, and wherein n is 0 or 1, comprises (a) providing a compound of formula (II)

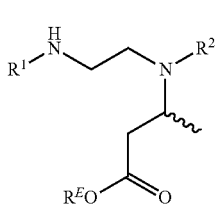
(II)

wherein $R^E$ is selected from the group consisting of H, alkyl, aryl, alkylaryl, heteroaryl cycloalkyl and heterocycloalkyl, more preferably wherein $R^E$ is alkyl, more preferably wherein $R^E$ is methyl, ethyl or propyl, more preferably wherein $R^E$ is methyl, (b) reacting the compound of formula (II) with a base and optionally reducing the compound to give the compound of formula (A), preferably (A*).

The Compound A

As described above, the compound of formula (A) has the structure

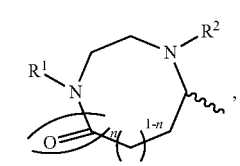
(A)

wherein n is 1 or 0. Thus the compound (A) has, e.g., the structure (Ia) or (Ib)

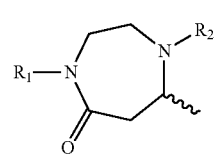
(Ia)

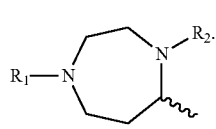
(Ib)

Thus, the present invention also relates to a method, as described above, and to a compound obtained or obtainable by said method, wherein the compound (A) has the structure

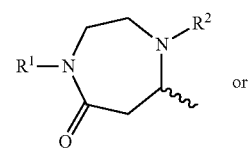
(Ia)

or

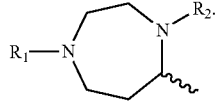
(Ib)

Residue $R^1$:

As described above, $R^1$ is selected from the group consisting of H, $PG^1$ and $R^A$ with $R^A$ being

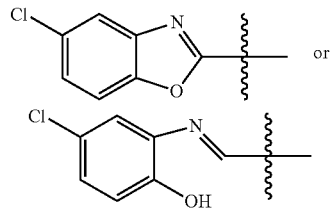
or wherein $PG^1$ is a suitable protecting group.

Thus, the compound of formula (A) has, e.g., a structure selected from the group consisting of

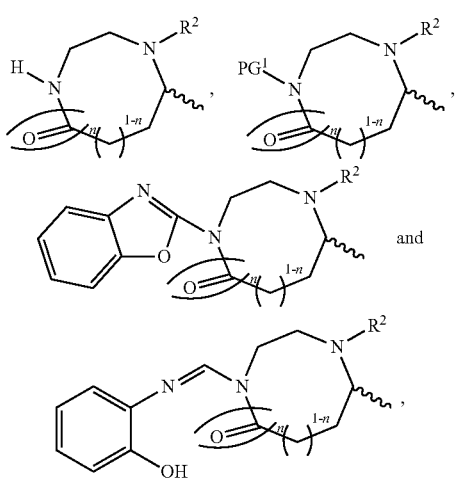

i.e. a structure selected from the group consisting of

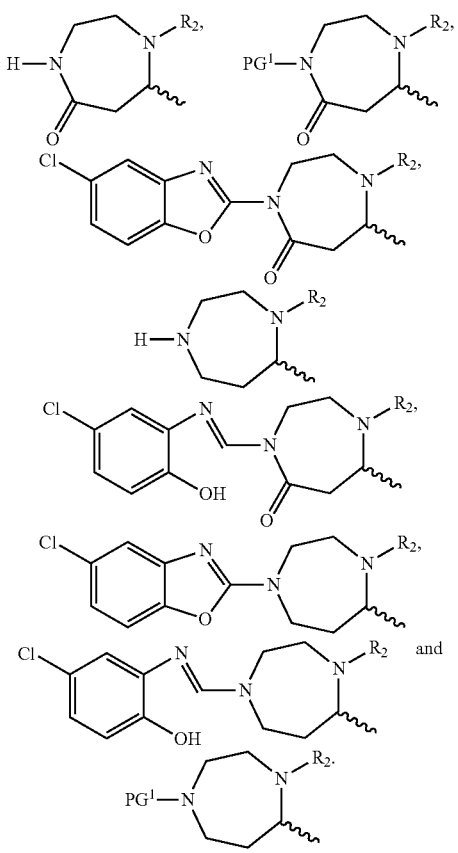

The term "suitable protecting group" as used herein is denoted to encompass any amino protecting group. The term "protecting group" as such refers to a chemical moiety that can be selectively attached to and removed from a particular chemically reactive functional group in a molecule to prevent it from participating in undesired chemical reactions. The protecting group will vary depending on reaction conditions to be employed and the presence of additional reactive or protecting groups in the molecule. It is understood that the term "amino protecting group" is a chemical moiety being attached to a former amino group. After removal of the protecting group, the free amine is regained. Representative protecting groups for amino groups are well known to those skilled in the art and are described, for example, in T. W. Greene and G. M. Wuts, *Protecting Groups in Organic Synthesis*, Third Edition, Wiley, N.Y., 1999, and references cited therein.

An "amino-protecting group" preferably includes both acyclic as well as cyclic protecting groups. A "cyclic protecting group" is a group which, together with the N to which it is bound, forms a cyclic group. Preferred protecting groups for $PG^1$ include, but are not limited to, carbamates, such as Boc (t-butyloxycarbonyl, Cbz (carboxybenzyl), Fmoc (fluorenylmethyloxycarbonyl), Alloc (allyloxycarbonyl), methyl and ethyl carbamates; trityl, benzyl, benzylidene, tosyl, PNZ, trifluoroacetate, phtalimide and the like; cyclic imide derivatives, such as succinimide and phthalimide; amides, such as formyl, (un)substituted acetyl, and benzoyl; and trialkyl silyl groups, such as t-butyldimethylsilyl and triisopropylsilyl. Particularly preferred amino-protecting groups include Boc, Cbz, Fmoc, benzyl, acetyl, benzoyl, trityl, Cbz, PNZ, Alloc, Trifluoroacetate, Phthalimide and the like. Most preferably, $PG^1$ is wherein $PG^2$ is selected from the group consisting of Benzyl, t-butyloxycarbonyl (Boc), Cbz, PNZ, Alloc, Trifluoroacetate and Phthalimide, more preferably $PG^1$ is a Boc group or a Cbz group, more preferably Boc.

Thus, compound A is preferably selected from the group consisting of

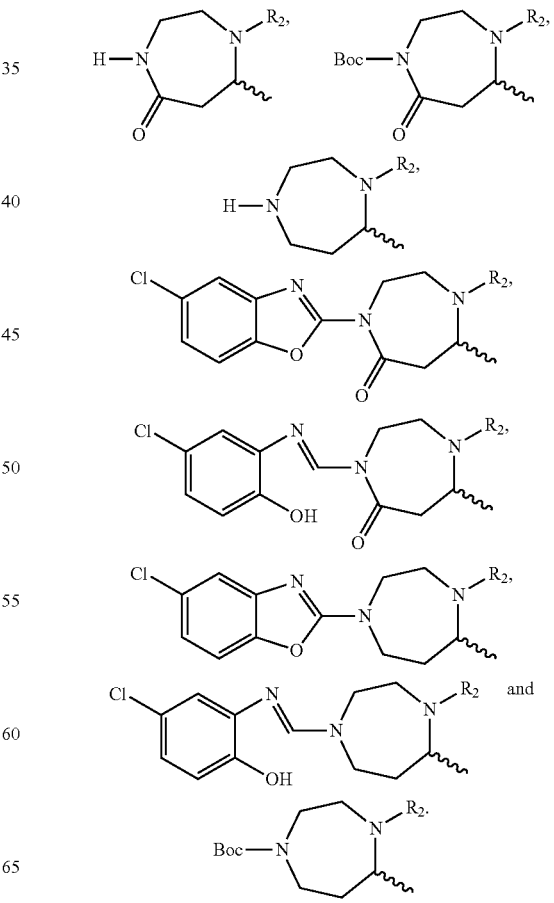

Preferably R¹ is selected from the group consisting of H,

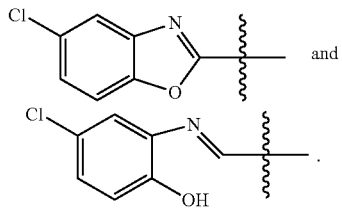

and

Most preferably R¹ is H.

Residue R²:

As descried above, R² is selected from the group consisting of H, PG² and R^B with R^B being

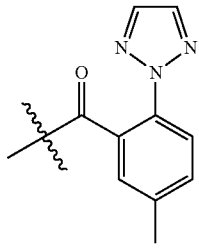 [SMILES: *C(=O)c1cc(C)ccc1-n1nccn1]

and wherein PG² is a suitable protecting group, and wherein n is 0 or 1.

Thus, the compound of formula (A) has, e.g., a structure selected from the group consisting of

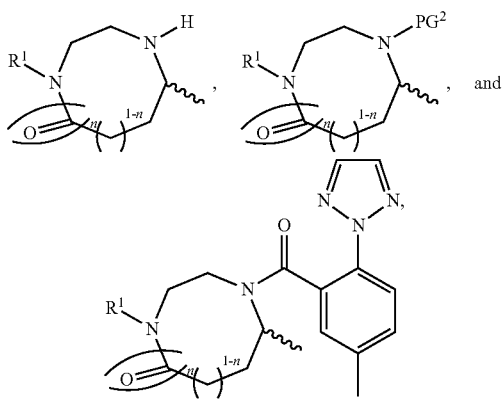

i.e. a structure selected from the group consisting of

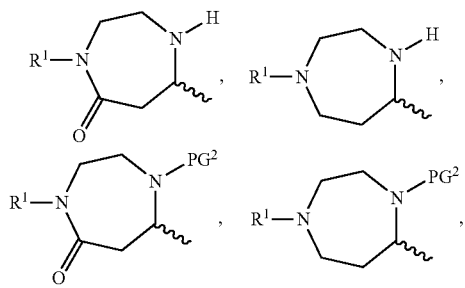

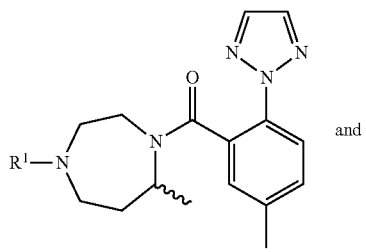

and

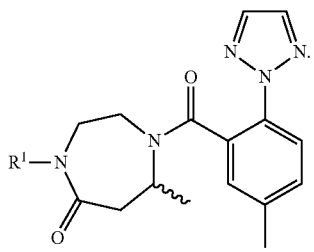

PG² is a suitable protecting group as defined above in connection with PG¹. Preferred protecting groups for PG² include, but are not limited to, carbamates, such as Boc (t-butyloxycarbonyl, Cbz (carboxybenzyl), Fmoc (fluorenylmethyloxycarbonyl), Alloc (allyloxycarbonyl), methyl and ethyl carbamates; trityl, benzyl, benzylidene, tosyl, PNZ, trifluoroacetate, phtalimideand the like; cyclic imide derivatives, such as succinimide and phthalimide; amides, such as formyl, (un)substituted acetyl, and benzoyl; and trialkyl silyl groups, such as t-butyldimethylsilyl and triisopropylsilyl. Particularly preferred amino-protecting groups include Boc, Cbz, Fmoc, benzyl, acetyl, benzoyl, trityl, Cbz, PNZ, Alloc, Trifluoroacetate, Phthalimide and the like. Most preferably, PG¹ is wherein PG² is selected from the group consisting of Benzyl, t-butyloxycarbonyl (Boc), Cbz, PNZ, Alloc, Trifluoroacetate and Phthalimide, more preferably PG² is a Boc group or a Cbz group, more preferably Cbz.

Thus, compound A is preferably selected from the group consisting of

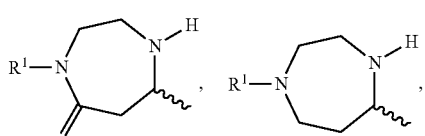

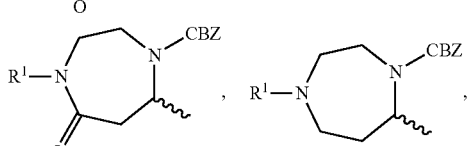

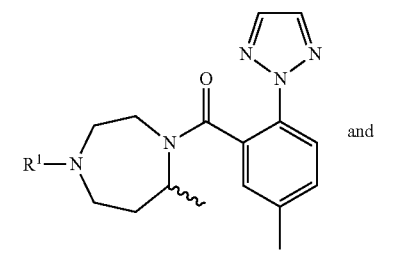

and

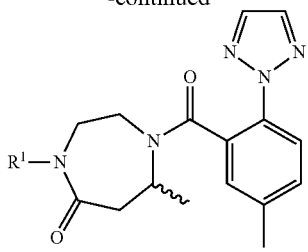

It is to be understood that in case R¹ and R² are both protecting groups, PG¹ and PG² preferably differ from each other. In this case, R¹ and R² are preferably orthogonal protecting groups.

The term "orthogonal protecting group" refers to a protecting group that is chemically resistant under one set of selected conditions, but is liable under another set of conditions, i.e. under certain conditions either PG¹ is cleaved and PG² is not, or vice versa. In such case, PG¹ is preferably Boc and PG² is preferably Cbz.

A bond shown as "⁓" in any one of the compounds shown above and below is denoted to represent a single bond, wherein the resulting structure including the bond "⁓" encompasses the single (isolated) S isomer or the single (isolated) R isomer as well as mixtures of the S and R isomer.

Preferably, compound A e.g. has as structure selected from the structure shown in the table below:

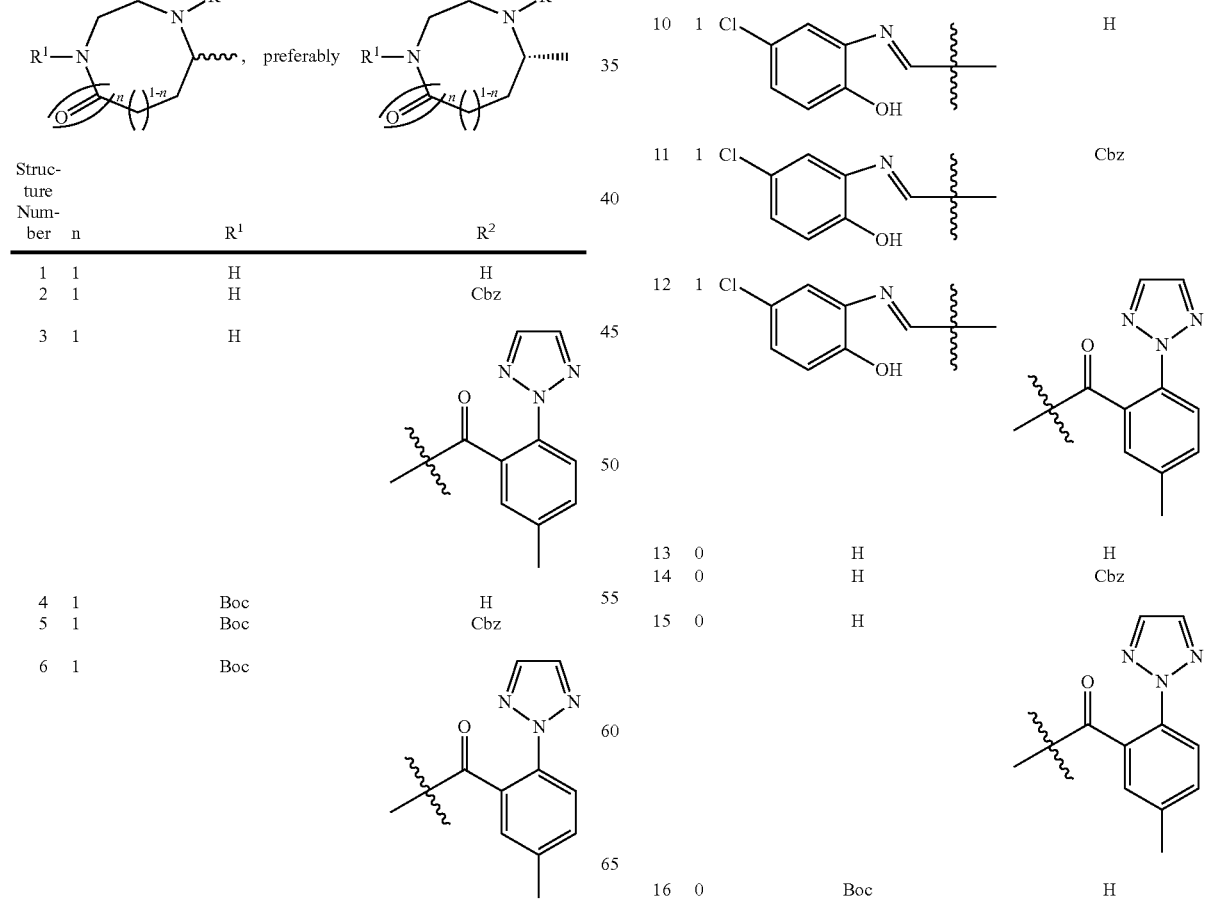

-continued

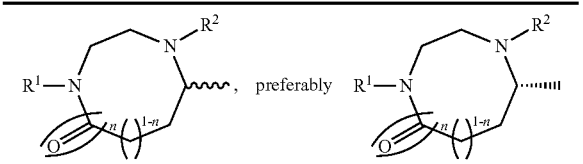

| Structure Number | n | R¹ | R² |
|---|---|---|---|
| 17 | 0 | Boc | Cbz |
| 19 | 0 | Boc | (triazole-phenyl-ketone group) |
| 19 | 0 | (Cl-benzoxazole) | H |
| 20 | 0 | (Cl-benzoxazole) | Cbz |
| 21 | 0 | (Cl-benzoxazole) | (triazole-phenyl-ketone group) |
| 22 | 0 | (Cl-hydroxyphenyl-imine) | H |
| 23 | 0 | (Cl-hydroxyphenyl-imine) | Cbz |
| 24 | 0 | (Cl-hydroxyphenyl-imine) | (triazole-phenyl-ketone group) |

Thus, the present invention also relates to a method for the preparation of a compound (A), as described above, and a compound obtained or obtainable by said process, wherein the compound has a structure selected from any one of the structures 1 to 24 shown above.

In particular, the present invention relates to a compound of formula (IX) shown above (which corresponds to structure 21 shown above), the compound being obtained or obtainable by the above described process, wherein said compound comprises less than 5% by weight, more preferably less than 2% by weight, more preferably less than 1% by weight, more preferably less than 100 ppm, of the regio-isomeric side product (IX-S) as impurity (IX-S)

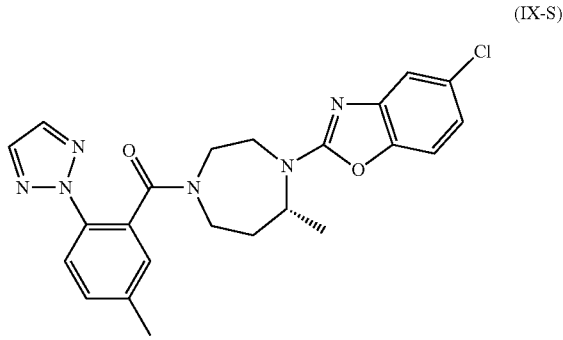 [SMILES: Cc1ccc(-n2nccn2)c(C(=O)N2CC[C@@H](C)N(c3nc4cc(Cl)ccc4o3)CC2)c1]

based on the total weight of the compound (IX), which includes the compound (IX-S). Preferably, the compound (IX) does not comprise the region-isomeric compound (IX-S) as impurity.

Further, the present invention also relates to a compound of formula (A) as such (A)

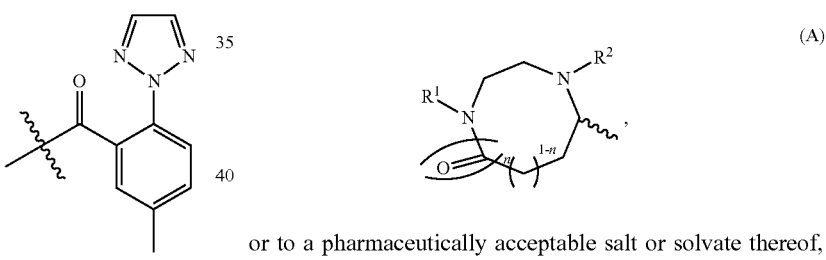

or to a pharmaceutically acceptable salt or solvate thereof, wherein (A) is preferably (A1)

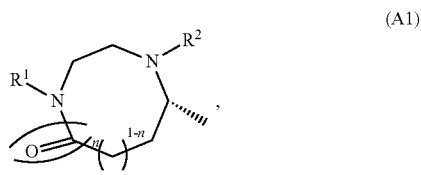

wherein R¹ is selected from the group consisting of H, PG¹ and R^A with R^A being

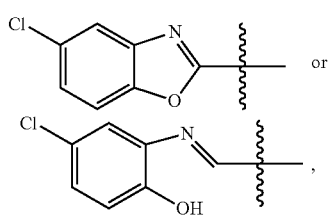

and wherein R² is selected from the group consisting of H, PG² and R^B with R^B being

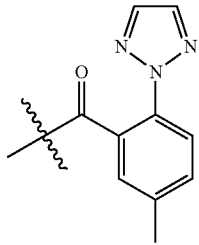 [SMILES: *C(=O)c1cc(C)ccc1-n1nccn1]

and wherein PG¹ and PG² are, independently of each other, suitable protecting groups,
and wherein n is 0 or 1, and wherein
in case n=0 and R¹ is R^A, R² is not R^B or H or, wherein in case n=0 and R¹ is R^A R^B is PG¹
and wherein in case n=0 and R¹ is H, R² is not R^B or, wherein in case n=0 and R¹ is H, R² is H or PG²
and wherein in case n=0 and R¹ is Cbz R² is not H or Boc or R^B
and wherein when n=1 R¹ and R² are not both H.

In case, R¹ is R^A and R² is R^B and n is 0, the compound having the structure (IX) preferably comprises less than 5% by weight, more preferably less than 2% by weight, more preferably less than 1% by weight, more preferably less than 100 ppm, of the regio-isomeric side product (IX-S) as impurity

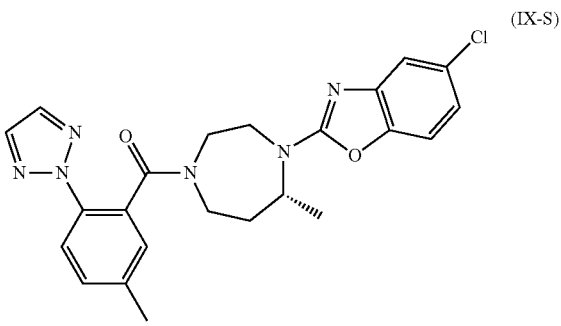 [SMILES: Cc1ccc(-n2nccn2)c(C(=O)N2CC[C@@H](C)N(c3nc4cc(Cl)ccc4o3)CC2)c1]

based on the total weight of the compound (IX), which includes the compound (IX-S). Preferably, the compound (IX) does not comprise the region-isomeric compound (IX-S) as impurity.

Preferably, the present invention relates to any one of the compounds 1 to 24 shown above as such. This will be outlined hereinunder in further detail.

Step (b)

In step (b) of the process of the invention, the compound of formula (II)

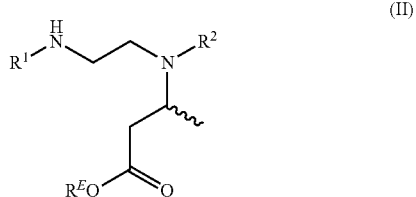

after is reacted with a base, and optionally subsequently reduced, to give, optionally further steps, the compound (A). Upon reaction with the base, the 7-membered ring of compound (A) is formed ("cyclization reaction").

The reaction may be carried out in any suitable solvent known to those skilled in the art. Preferably, the cyclization reaction is carried out in an organic solvent, more preferably in a solvent selected from the group consisting of $R^E$—OH, tetrahydrofuran, 2-methyltetrahydrofuran, methyltertbutylether, diethylether, diisopropylether, toluene, acetonitrile and mixtures of two or more thereof, with $R^E$ being as described above and below, preferably wherein $R^E$ is selected from the group consisting of alkyl, aryl, alkylaryl, heteroaryl cycloalkyl and heterocycloalkyl. Preferably the solvent has the structure $R^E$—OH, with $R^E$ being as described above and below, preferably wherein $R^E$ is selected from the group consisting of alkyl, aryl, alkylaryl, heteroaryl cycloalkyl and heterocycloalkyl, more preferably wherein $R^E$ alkyl, more preferably wherein $R^E$ methyl, ethyl or propyl, more preferably wherein $R^E$ methyl. Preferably, the cyclization is carried out at a temperature in the range of from −20 to 80° C., more preferably in the range of from 0 to 50, more preferably in the range of from 20 to 30° C. During the reaction, the temperature may be varied or held essentially constant.

Preferably, as base, a base selected from the group consisting of $NaOR^E$, Na-tert.butoxid, K-tert.butoxid, $NaNH_2$, DBU, Tetramethylguanidin, Na—$CH_2S(O)CH_3$ and mixtures of two or more thereof is employed, with $R^E$ being selected from the group consisting of alkyl, aryl, alkylaryl, heteroaryl cycloalkyl and heterocycloalkyl, more preferably wherein $R^E$ alkyl, more preferably wherein $R^E$ methyl, ethyl or propyl, more preferably wherein $R^E$ methyl. Most preferably, the base is sodium methanolate.

The weight ratio of base to compound of formula (II) is preferably in the range of from 0 to 8, more preferably in the range of from 1 to 5.

Generally, when providing the reaction mixture to be reacted in (b), the sequence of mixing the components of the reaction mixture is not subject to specific restrictions. Preferably, the compound of formula (II) is first admixed with at least a portion of a suitable solvent and, to the resulting mixture, the base is added which, for example, can be employed as mixture with at least a portion of the solvent or as such.

Compound (II) is preferably allowed to react with the base for a time in the range of from 0 to 24 h, more preferably in the range of from 0 to 5 h, more preferably in the range of from 0 to 3 h.

In case compound (A) has the structure (Ia) (which means that n in compound (A) is 1), in step (b) the compound of formula (II) is reacted with a base to give, optionally after further steps, the compound (A). In this case, no additionally reduction step is necessary. Directly upon reaction with the base, the 7-membered ring of compound (A) is formed ("cyclization reaction").

In case compound (A) has the structure (Ib) (which means that n in compound (A) is 0), in step (b) the compound of formula (II) is reacted with a base to give, as intermediate product, the compound of formula (Ia), which is thereafter reduced to give, optionally after further steps, the compound (A). In this case, a reduction of the carbonyl group is thus carried out.

Thus, the present invention also relates to a process, as described above, as well as to a compound obtained or obtainable by said process, wherein the compound of formula (A) has the structure of formula (Ib), and wherein in step (b), upon reaction with the base, a compound of formula (Ia) is formed

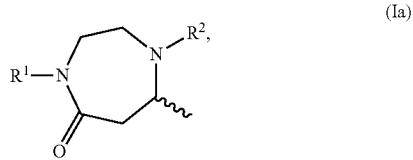

and wherein step (b) further comprises reducing the compound of formula (Ia).

It is to be understood that in this case compound (Ia) may be isolated or may be directly reduced in situ to give the compound of formula (Ib). If such isolation is carried out, this may be carried out by any method known to those skilled in the art. Such isolation may comprise one or more stages wherein preferably at least one stage comprises a purification, such as an extraction and/or a precipitation and/or filtration.

Preferably, step (b) comprises (b1) reacting the compound of formula (II) with a base to give a composition comprising a compound of formula (Ia)

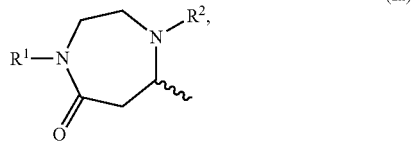

(b2) optionally purifying the composition obtained in (b1),
(b3) optionally reducing the compound of formula (Ia) to give a compound of formula (Ib)

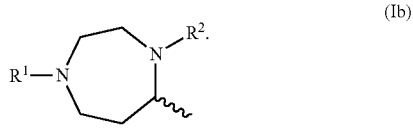

As mentioned above with respect to step (b), also step (b1) is preferably carried out in an organic solvent, more preferably in a solvent selected from the group consisting of methanol, ethanol, propanol, isopropanol, butanol, s-butanol, t-butanol, tetrahydrofuran, 2-methyltetrahydrofuran, methyltertbutylether, diethylether, diisopropylether, toluene, acetonitrile and mixtures of two or more thereof. Preferably the solvent has the structure $R^E$—OH is employed, with $R^E$ being as described above and below, preferably wherein $R^E$ is selected from the group consisting of alkyl, aryl, alkylaryl, heteroaryl cycloalkyl and heterocycloalkyl, more preferably wherein $R^E$ is alkyl, more preferably wherein $R^E$ is methyl, ethyl or propyl, more preferably wherein $R^E$ is methyl.

Preferably, step (b1) is carried out at a temperature in the range of from −20 to 80° C., more preferably in the range of from 0 to 50, more preferably in the range of from 20 to 30° C. During the reaction, the temperature may be varied or held essentially constant.

As to step (b3), step (b3) is carried out in an organic solvent, more preferably in a solvent selected from the group consisting of methanol, ethanol, nPrOH (n-propanol), i-PrOH (isopropanol), THF (tetrahydrofuran), 2-MeTHF (2-methyl-tetrahydrofuran), MTBE (Methyl-tert-butylether), DIPET (diisopropylethylether), toluene, acetonitrile, $CH_2Cl_2$ and mixtures of two or more thereof.

Preferably, step (b3) is carried out at a temperature in the range of from −20° C. to 110° C.

Preferably, in step (b3), the compound is reduced by reaction with a reducing agent selected from the group consisting of $NaBH_4$, $NaCNBH_3$, $NaBH(OAc)_3$, $LiAlH_4$, $LiBH_4$ and $H_2$ in the presence of transition metals, wherein the transition metal is preferably selected from the group consisting of IR, Pt, Fe, Rh, Pd, Re, Ru, Ni and Co. More preferably, the reducing agent is selected from the group consisting of $NaBH_4$, $NaCNBH_3$, $NaBH(OAc)_3$, $LiAlH_4$ and $LiBH_4$, more preferably the reducing agent is $NaBH_4$, $NaCNBH_3$ or $NaBH(OAc)_3$, more preferably $NaBH_4$.

Preferably, the compound (A) has the structure (Ia*) or (Ib*)

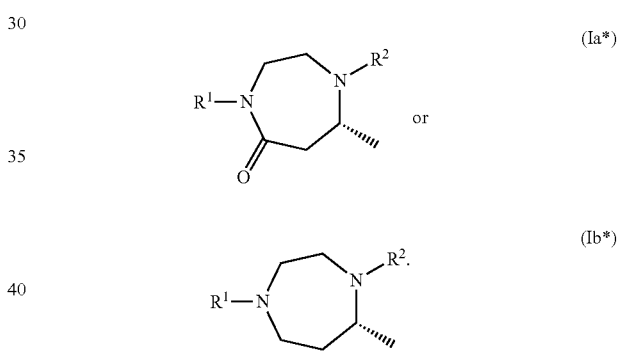

Thus, in step (b), preferably compound (Ia*) or (Ib*) is prepared. Thus, preferably, in step (b) of the process of the invention, the compound of formula (II)

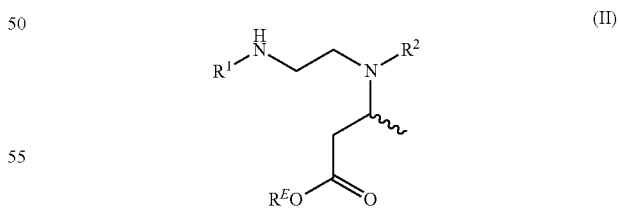

is reacted with a base and optionally subsequently reduced to give, optionally after further steps, the compound (A), with (A) being (Ia*) or (Ib*). Upon reaction with the base, the 7-membered ring of compound (A) is formed ("cyclization reaction").

It is to be understood that since compound (II) comprises the single bond shown as "〰", i.e. that compound (II) has either the structure

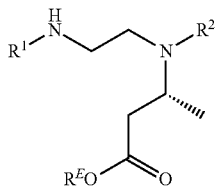
(II*)

or consists of a mixture of

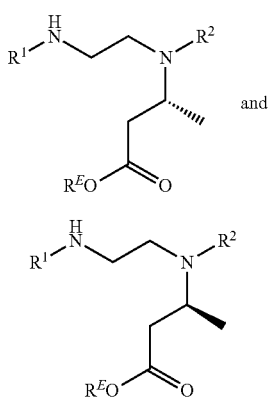

as mentioned above.

In case compound (A) has the structure (A*), such as (Ia*) or (Ib*), preferably in step (a) compound (II) is provided in the correct stereochemistry, i.e. as compound (II*)

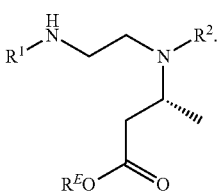
(II*)

This compound is then employed in step (b) instead of the racemic mixture consisting of (II*) and (II**) shown above.

According to an alternative preferred embodiment, in case compound (II) consists of a racemic mixture, in step (b), in the cyclization reaction of compound (II), a compound (A) consisting of a racemic mixture is obtained. Preferably, in this case, a chiral resolution of (A) us carried out. More preferably, in this case, $R^2$ is H, and compound (A) is (A1),

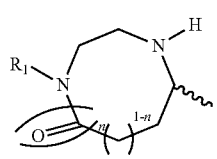
(A1)

which consists of a racemic mixture of the compounds (A1*) and (A1**) is obtained,

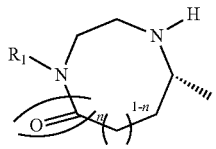
(A1*)

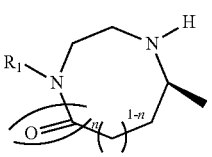
(A1**)

wherein the compound (A1) contains from 20 to 75% by weight-% of the compound of formula (A1*) based on the total weight of the sum of (A1*) and (A1**), and wherein this mixture is then resolved by chiral resolution to finally give, optionally after further steps, the compound (A) in which $R^2$ is H.

Preferably, this is carried out by (I) adding a single stereoisomer of a chiral acid and precipitating, preferably crystallizing, a chiral acid salt (T) of compound (A1), thereby obtaining a mixture comprising the precipitated, preferably crystallized, tartaric acid salt (T) and the solvent, (II) preferably separating the precipitated, preferably crystallized, chiral acid salt (T) of the compound of formula (A1) from the mixture obtained in (I), wherein the chiral acid salt (T) contains at least 80% by weight of the chiral acid salt of the compound of formula (A1*) based on the total weight of the chiral acid salt of the compound of formula (A1), (III) converting the chiral acid salt (T) to the free base.

Preferably, in step (I), upon addition of the chiral acid in a suitable solvent, a chiral acid salt (T*) of at least part of the compound of formula (II) is formed, and at least part of this chiral acid salt (T*) formed is precipitated, preferably crystallized, thereby obtaining a mixture comprising the precipitated, preferably crystallized, tartaric acid salt (T) and the solvent.

The chiral acid is preferably a single stereoisomer of a tartaric acid derivative, more preferably of a tartaric acid derivative selected from the group consisting of Ditoluoyl tartaric acid, Dibenzoyl tartaric acid, Dianisoyl tartaric acid, Dibenzoyl tartaric acid mono(dimethylamide) and a mixture of two or more thereof.

The term "single stereoisomer of a chiral acid" in this context is denoted to mean that the chiral acid comprises less than 1% by weight, preferably less than 0.5% by weight, more preferably less than 0.1% by weight, more preferably less than 0.05% by weight, more preferably less than 0.01% by weight, more preferably essentially no, more preferably no impurities of respective other stereoisomers of the chiral acid, based on the total weight of the chiral acid. In case the chiral acid is a tartaric acid derivative being a mixture of two or more of 2,3-Ditoluoyl tartaric acid, 2,3-Dibenzoyl tartaric acid, 2,3-Dianisoyl tartaric acid and 2,3-Dibenzoyl tartaric acid mono(dimethylamide), respectively, this means that of each of the chiral acid derivatives within the mixture only a single stereoisomer is present.

Preferably, the process comprises (I) forming a chiral acid salt, preferably a tartaric acid salt, (T*) of at least part of the compound of formula (A1) by treating the compound of formula (A1) with a single stereoisomer of a chiral acid, preferably of a tartaric acid derivative selected from the group consisting of Ditoluoyl tartaric acid, Dibenzoyl tartaric acid, Dianisoyl tartaric acid, Dibenzoyl tartaric acid mono(dimethylamide) and a mixture of two or more thereof, in a suitable solvent, and precipitating, preferably crystallizing, at least part of the tartaric acid salt (T*) formed, thereby obtaining a mixture comprising the precipitated, preferably crystallized, tartaric acid salt (T) and the solvent;

(II) preferably separating the precipitated, preferably crystallized, chiral acid salt (T) of the compound of formula (A1) from the mixture obtained in (I), wherein the chiral acid salt (T) of the compound of formula (A1) contains at least 80% by weight of the chiral acid salt of the compound of formula (A1*) based on the total weight of the chiral acid salt of the compound of formula (A1), (III) converting the chiral acid salt (T) of (A1) to the free base (A1*).

Thus, the present invention also relates to a process, as described above, and a compound obtained or obtainable by the above described method, the method comprising (a) providing a compound of formula (II),

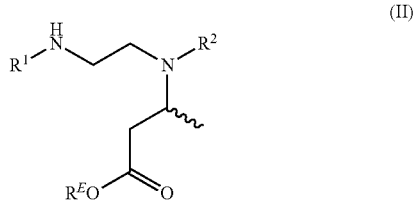

wherein $R^E$ is selected from the group consisting of H, alkyl, aryl, alkylaryl, heteroaryl cycloalkyl and heterocycloalkyl, more preferably wherein $R^E$ is alkyl, more preferably wherein $R^E$ is methyl, ethyl or propyl, more preferably wherein $R^E$ is methyl, (b) reacting the compound of formula (II) with a base and optionally reducing the compound and/or purifying the compound, to give a compound (A1) which consists of an enantiomeric mixture of the compounds (A1*) and (A1**),

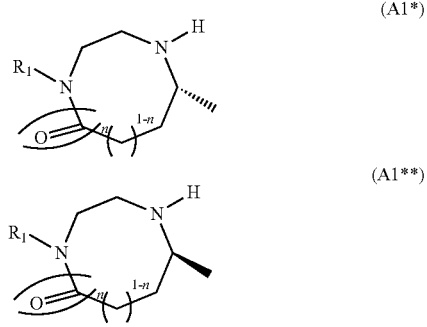

(I) forming a chiral acid salt, preferably a tartaric acid salt, (T*) of at least part of the compound of formula (A1) by treating the compound of formula (A1) with a single stereoisomer of a chiral acid, preferably a single stereoisomer of a tartaric acid derivative, more preferably of a tartaric acid derivative selected from the group consisting of Ditoluoyl tartaric acid, Dibenzoyl tartaric acid, Dianisoyl tartaric acid, Dibenzoyl tartaric acid mono(dimethylamide) and a mixture of two or more thereof, in a suitable solvent, and precipitating, preferably crystallizing, at least part of the tartaric acid salt (T*) formed, thereby obtaining a mixture comprising the precipitated, preferably crystallized, tartaric acid salt (T) and the solvent, (II) preferably separating the precipitated, preferably crystallized, chiral acid salt (T) of the compound of formula (A1) from the mixture obtained in (I), wherein the chiral acid salt (T) of the compound of formula (A1) contains at least 90% by weight of the chiral acid salt of the compound of formula (A1*) based on the total weight of the chiral acid salt of the compound of formula (A1), (III) converting the chiral acid salt (T) of (A1) to the free base (A1*), wherein (A) is (A1*).

Step (I)

The compound of formula (A1) employed in (I) contains of from 20 to 75% by weight, more preferably of from 40 to 60% by weight, of the compound of formula (A1*) based on the total weight of the sum of (A1*) and (A1**).

In step (b), at least part of the compound of formula (A1) obtained in the cyclization reaction is transformed into the corresponding chiral acid salt, preferably tartaric acid salt, (T*). The chiral acid salt (T*) contains the chiral acid salt of the compound of formula (A1*), e.g. in an amount in the range of from 1 to 80% by weight, such as in the range of from 10 to 70% by weight, or in the range of from 30 to 60% by weight, or in the range of from 45 to 55% by weight, based on the total amount of the chiral acid salt (T*).

Subsequently, at least part of (T*) is precipitated, preferably crystallized. This is preferably achieved by contacting (treating) the compound of formula (A1) in a suitable solvent with the chiral acid. Thereby, a mixture comprising the crystallized chiral acid salt (T) of the compound of formula (A1*) and the solvent is formed. As mentioned above, the precipitated, preferably crystallized, tartaric acid salt (T) of the compound of formula (A1) contains at least 90% by weight of chiral acid salt of the compound of formula (A1*) based on the total weight of the chiral acid salt of the compound of formula (A1).

It is to be noted that the mixture obtained in step (I) may comprise further compounds, in particular non crystalline forms of the compound of formula (A1) and salts thereof. Preferably, the mixture obtained in (I) comprises non-crystalline forms of the compound of formula (A1**) and chiral acids salts thereof.

The chiral acid salt (T*) of the compound of formula (A1) is denoted to encompass all chiral acid salts of compound (A1) formed in step (I) including the chiral acid salt (T) which precipitates as well as all chiral acid salts formed which remain dissolved. Thus, the chiral acid salt (T*) may comprise a mixture of chiral acid salts of compounds of formula (A1*) and (A1**).

Preferably, in step (I) and (II), thus a chiral resolution of the stereoisomers (A1*) and (A1**) is carried out.

As to the solvent used in step (I), any suitable organic solvent in which the compound of formula (A1) is sufficiently soluble may be used. In particular, the solvent is selected from the group consisting of EtOH, i-PrOH, nPrOH, acetone, toluene, MTBE, $CH_2Cl_2$, ethyl acetate, acetone, isopropanol, methanol, water, formic acid ethyl ester, isopropyl acetate, propyl acetate, butyl acetate, acetonitrile, tetrahydrofuran, dichloromethane, methylisobutylketone, toluene, hexane, cyclohexane, heptane and mixtures of two or more thereof. More preferably, the suitable solvent comprises acetone or methanol, more preferably the suitable solvent is acetone or methanol.

It is to be understood that in step (I) a further solvent may be added in order to precipitate, preferably crystallize, the chiral acid salt (T). In this case, the mixture obtained in (I) preferably additionally comprises said further solvent.

This further solvent may be added prior to, together with or after the addition of the chiral acid to the compound of formula (A1). According to a preferred embodiment, the compound of formula (A1) is dissolved in the suitable solvent mentioned above and a mixture, preferably a solution of the chiral acid, in a further solvent is added to the solution, wherein the further solvent and the suitable solvent may be the same or may be different.

In particular, the further solvent is selected from the group consisting of EtOH, i-PrOH, nPrOH, acetone, toluene, MTBE, $CH_2Cl_2$, ethyl acetate, acetone, isopropanol, methanol, water, formic acid ethyl ester, isopropyl acetate, propyl acetate, butyl acetate, acetonitrile, tetrahydrofuran, dichloromethane, methylisobutylketone, toluene, hexane, cyclohexane, heptane and mixtures of two or more thereof. More preferably, the suitable solvent comprises acetone or methanol, more preferably the further solvent is acetone or methanol. More preferably, the suitable solvent and the further solvent are the same, in particular both comprise acetone or methanol, preferably both are acetone or methanol.

Thus, the present invention also relates to a process for the preparation of a chiral acid salt (T) of a compound of formula (A1), as described above, and a chiral acid salt (T) of compound of formula (A1), obtained or obtainable by said process, wherein step (I) comprises dissolving the compound of formula (A1) in the suitable solvent and adding a solution of the chiral acid dissolved in a further solvent to the solution, wherein the further solvent and the suitable solvent are preferably the same, more preferably acetone or methanol.

Preferably, the compound of formula (A1) is dissolved in the suitable solvent and the mixture is heated to a temperature in the range of from 20 to 80° C., more preferably to a temperature in the range of from 30 to 60° C., more preferably to a temperature in the range of from 30 to 50° C., more preferably to a temperature in the range of from 30 to 40° C., prior to the addition of the tartaric acid. During the heating step, the temperature may be varied, constantly or stepwise, or held essentially constant. Preferably, the mixture is heated until a clear solution of the compound of formula (A1) in the suitable solvent is obtained. Optionally, the mixture is afterwards cooled to room temperature.

The precipitation, preferably the crystallizing, in step (I) is preferably carried out at a temperature in the range of from 0 to 60° C., wherein the temperature is preferably continuously or stepwise decreased during step (b). The chiral acid may thus e.g. be added to a solution of the compound of formula (A1) in the suitable solvent which has been previously heated or which has been previously heated and afterwards cooled to a specific temperature, or which has not been previously heated.

After the addition of the chiral acid derivative, and optionally the further solvent, the mixture may again be heated or alternatively be cooled, or the temperature may be held constant. Preferably, the mixture is cooled to a temperature in the range of from 0 to 50° C., more preferably to a temperature in the range of from 0 to 40° C., more preferably to a temperature in the range of from 10 to 30° C.

Preferably, the mixture obtained in step (I) consists of the chiral acid salt (T), optionally unreacted chiral acid derivative, optionally unreacted compound of formula (A1), optionally further chiral acid salts (salt (T*) minus the amount of precipitated chiral acid salt (T), the suitable solvent and optionally the further suitable solvent.

Step (II)

In the optional step (II) of the process of the invention, the chiral acid salt (T) is separated from the mixture obtained in step (I).

It is to be understood that, if the chiral acid is a tartaric acid or tartaric acid derivative, a salt between two molecules of (A) and one molecule of the chiral acid may be formed. Such salts are thus encompassed by the term "the acid salt (T)". The separation may be carried out by any suitable method known to those skilled in the art. Preferably, the separating in step (II) is carried out by centrifugation or filtration, preferably filtration.

It is to be understood that the separated salt may be subjected to a further treatment such as an after-treatment such as a purification step and/or lyophilization.

Preferably, the obtained chiral acid salt (T) of the compound formula (A1) contains at least 95% by weight, more preferably at least 96% by weight, more preferably at least 97% by weight, more preferably at least 98% by weight, more preferably at least 99% by weight, more preferably at least 99.5% by weight, more preferably at least 99.9% by weight, of the tartaric salt of the compound of formula (A1*), based on the total weight of chiral acid salt of the compound of formula (A1), i.e. based on the sum of (A1**) and (A1*). More preferably, the chiral acid salt (T) of the compound of formula (A1) consists of the chiral acid salt of the compound of formula (A1*).

Preferably, the chiral acid is a di-benzoyl tartaric acid or a di-toluoyl tartaric acid.

According to a preferred embodiment, A1 is (Ia),

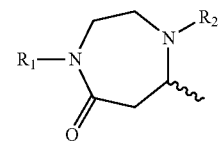

with $R^2$=H,
and consists of a mixture of (Ia*) and (Ia**)

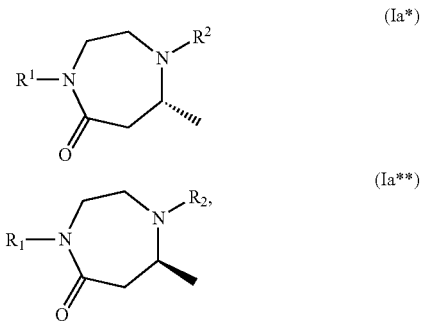

(Ia*)

(Ia**)

wherein $R^2$=H. In this case, the chiral acid is preferably or a di-toluoyl tartaric acid, more preferably L-di-toluoyl tartaric acid (LTTA). Most preferably $R^2$=H and $R^1$=H and the chiral acid is L-di-toluoyl tartaric acid. In this case, the suitable solvent is preferably methanol.

According to a further preferred embodiment, A1 is (Ib), with $R^2$=H, and consists of a mixture of (Ib*) and (Ib**)

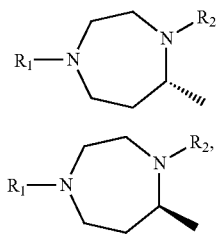

(Ib*)

(Ib**)

wherein $R^2$=H. In this case, the chiral acid is preferably a di-benzoyl tartaric acid, more preferably D-di-benzoyl tartaric acid (DBTA). Most preferably $R^2$=H and $R^1$=Cbz and the chiral acid is D-di-benzoyl tartaric acid. In this case, the suitable solvent is preferably acetone.

As mentioned above, the compound (A) is preferably being used for the preparation of the compound of formula (IX) (Suvorexant). Thus, the present invention also relates to a process for the preparation of a compound of formula (IX), comprising
(A) preparing a compound of formula (A) as described hereinunder and above, wherein in case n=0, at least one of $R^A$ or $R^B$ is H or a protecting group,
(B) transforming the compound (A) into the compound of formula (IX).

According a preferred embodiment, compound (A) has the structure (Ia), preferably (Ia*), with $R^1$ being H and with $R^2$ being $PG^2$. Thus, the present invention preferably relates to a process for the preparation of a compound and a compound obtained or obtainable by said process, the compound having the structure

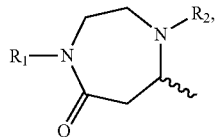

(Ia)

or being a pharmaceutically acceptable salt or solvate thereof, wherein (Ia) is preferably (Ia*)

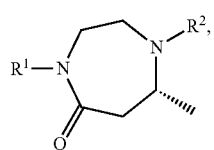

(Ia*)

and wherein $R^1$ is H and $R^2$ is $PG^2$, the process comprising
(a) providing a compound of formula (II),

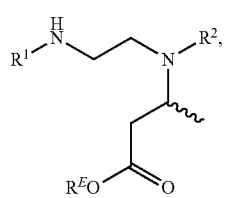

(II)

preferably of formula (II*),
wherein $R^E$ is selected from the group consisting of H, alkyl, aryl, alkylaryl, heteroaryl cycloalkyl and heterocycloalkyl, more preferably wherein $R^E$ is alkyl, more preferably wherein $R^E$ is methyl, ethyl or propyl, more preferably wherein $R^E$ is methyl,
(b) reacting the compound of formula (II), preferably of formula (II*), with a base, to give the compound of formula (Ia), with $R^1$ being H and with $R^2$ being $PG^2$, preferably (Ia*) with $R^1$ being H and with $R^2$ being $PG^2$. Preferably, compound (Ia), with $R^1$ being H and with $R^2$ being $PG^2$, thus compound

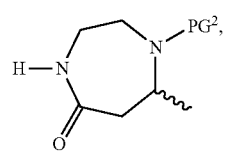

more preferably compound (Ia*) with $R^1$ being H and with $R^2$ being $PG^2$, thus compound

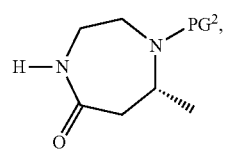

is used for the preparation of Suvorexant. Thus, the present invention also relates to the use of the compound of formula (Ia), preferably (Ia*), in which $R^1$ is H and $R^2$ is $PG^2$, for the preparation of Suvorexant.

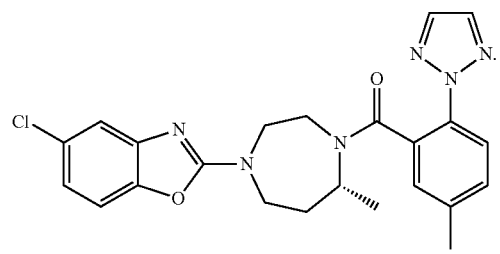

Further, the present invention relates to a process for the preparation of a compound of formula (IX) and a compound of formula (IX) obtained or obtainable by said process comprising
(A) providing a compound of formula (Ia) by a process comprising
(a) providing a compound of formula (II)

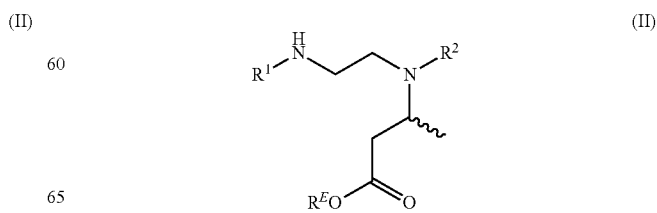

(II)

wherein R$^E$ is selected from the group consisting of H, alkyl, aryl, alkylaryl, heteroaryl cycloalkyl and heterocycloalkyl, more preferably wherein R$^E$ is alkyl, more preferably wherein R$^E$ is methyl, ethyl or propyl, more preferably wherein R$^E$ is methyl, and wherein R$^1$ is H and R$^2$ is PG$^2$, (b) reacting the compound of formula (II) with a base, to give the compound of formula (Ia), with R$^1$ being H and with R$^2$ being PG$^2$, preferably (Ia*) with R$^1$ being H and with R$^2$ being PG$^2$, (B) transforming the compound of step (A) into the compound of formula (IX).

Preferably, step (B) comprises (c1) removal of the protecting group PG$^2$, (d1) reacting the compound of formula (Ia) with R$^1$ and R$^2$ being H with a compound of formula (XI)

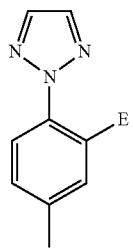

(XI)

wherein E is —COOH or a reactive carboxy group, to give a compound of formula (VIIa) in which R$^1$ is H,

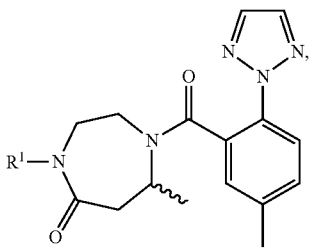

(VIIa)

preferably

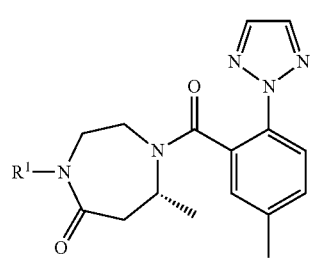

(VIIa*)

(e1) reducing the compound, to give a compound of formula (VIIb) in which R$^1$ is H

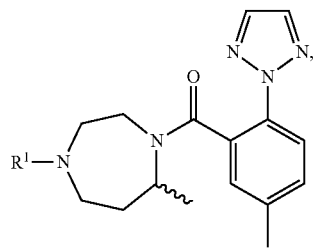

(VIIb)

preferably

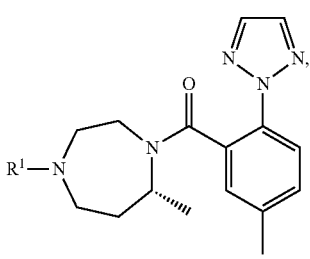

(VIIb*)

preferably with a reducing agent selected from the group consisting of NaBH$_4$, NaCNBH$_3$, NaBH(OAc)$_3$, LiAlH$_4$, LiBH$_4$ and H$_2$ in the presence of transition metals, wherein the transition metal is preferably selected from the group consisting of Ir, Pt, Fe, Rh, Pd, Re, Ru, Ni and Co, (f1) reacting the compound of formula (VIIb), preferably (VIIb*) with a compound of formula (XII)

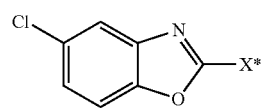

(XII)

wherein X* is a leaving group, preferably Cl.

In an embodiment, (e1) optionally comprises (e1-1) preparing a salt of the compound of formula (VIIb) in which R$^1$ is H, preferably (VIIb*) in which R$^1$ is H and preferably wherein the salt is an hydrochloride salt or a sulphate salt, (e1-2) optionally purifying the compound obtained in (e1) or (e1-1), wherein preferably purifying comprises crystallizing the compound obtained in (e1) or (e1-1), (e1-3) optionally transforming the crystalline salt of (e1-2) in the free base of formula (VIIb), preferably (VIIb*).

Preferably, in step (e1-2), the crystalline form (A) or the crystalline form (I) is obtained.

Preferably in step (e1-2), the crystalline form (I-S) or the crystalline form (I-Cl) are obtained. Crystalline forms (A), (I), (I-S) and (I-Cl) are disclosed herein below.

The present invention further relates to a compound obtained or obtainable by said process (this includes a salt thereof). Further, the present invention relates to a compound of formula (VIIa), preferably (VIIa*), as mentioned above. Further the present invention relates to a compound (VIIb), preferably (VIIb*), as mentioned above.

The present invention relates to a compound of formula (VIIb) or a salt thereof, more preferably (VIIb*), in which R$^1$ is H, which are in a crystalline form.

A crystalline form of the compound (VIIb) in which R¹ is H is crystalline form (A) and has an X-ray powder diffraction pattern comprising a peak at 2-theta angle of approximately 12.4°±0.2°. Preferably, the crystalline form (A) in which R¹ is H has an X-ray powder diffraction pattern comprising peaks at 2-theta angles of approximately 4.8±0.2°, 12.4°±0.2°, 14.2°±0.2°, 19.9°±0.2° and 20.8°±0.2° or has an X-ray powder diffraction pattern comprising peaks at 2-theta angles of approximately 7.7±0.2°, 11.4°±0.2°, 12.4°±0.2°, 16.2°±0.2° and 18.1°±0.2°. More preferably, the crystalline (A) thereof in which R¹ is H has an X-ray powder diffraction pattern comprising peaks at 2-theta angles of approximately 4.8±0.2°, 12.4°±0.2°, 14.2°±0.2°, 19.9°±0.2° and 20.8°±0.2°. The X-ray powder diffraction pattern is as measured at a temperature in the range of from 15 to 25° C. with Cu-Kα$_{1,2}$ radiation having a wavelength of 0.15419 nm.

Alternatively crystalline form (A) has an X-ray powder diffraction pattern comprising a peak at 2-theta angle of approximately 12.4°±0.2°, more preferably has an X-ray powder diffraction pattern comprising peaks at 2-theta angles of approximately 4.8±0.2°, 12.4°±0.2°, 14.2°±0.2°, 19.9°±0.2° and 20.8°±0.2. The X-ray preferably further comprises peaks at one or more than one or all of 2-theta angles of 21.6°±0.2°, 22.6°±0.2° 22.9°±0.2 and 27.8°±0.2. ° The X-ray powder diffraction pattern is measured at a temperature in the range of from 15 to 25° C. with Cu-Kα$_{1,2}$ radiation having a wavelength of 0.15419 nm.

A crystalline form of compound (VIIb*) wherein R¹ is H is crystalline form (I) and has an X-ray powder diffraction pattern comprising a peak at 2-theta angle of approximately 11.3°±0.2°, more preferably has an X-ray powder diffraction pattern comprising peaks at 2-theta angles of 11.3±0.2°, 12.3°±0.2°, 13.3°±0.2°, 16.0°±0.2°, 20.0±0.2°. Preferably, the X-ray powder diffraction pattern further comprises peaks at 2-theta angles of 16.5°±0.2°, 18.3. °±0.2°, 20.1°±0.2°, 22.7°±0.2°. The X-ray powder diffraction pattern is as measured at a temperature in the range of from 15 to 25° C. with Cu-Kα$_{1,2}$ radiation having a wavelength of 0.15419 nm.

Compound of formula (VIIb) and of formula (VIIb*) or salt thereof and the crystalline form thereof as disclosed below are preferably obtained or obtainable by a process as described above, wherein step (e1) preferably comprises reducing the compound, to give a compound of formula (VIIb) in which R¹ is H

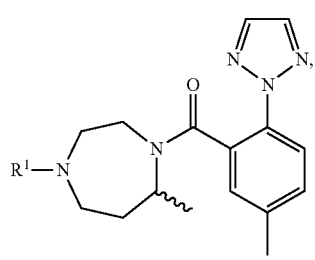

(VIIb)

preferably

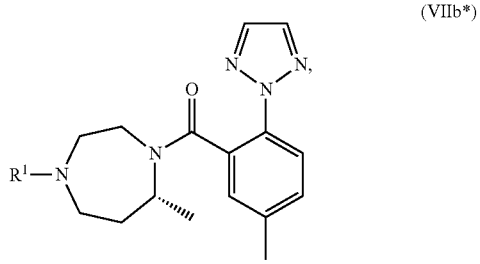

(VIIb*)

preferably with a reducing agent selected from the group consisting of NaBH$_4$, NaCNBH$_3$, NaBH(OAc)$_3$, LiAlH$_4$, LiBH$_4$ and H$_2$ in the presence of transition metals, wherein the transition metal is preferably selected from the group consisting of IR, Pt, Fe, Rh, Pd, Re, Ru, Ni and Co, more preferably wherein the reducing agent is selected from the group consisting of NaBH$_4$, NaCNBH$_3$, NaBH(OAc)$_3$, LiAlH$^4$, and LiBH$_4$, more preferably the reducing agent is NaBH$_4$, NaCNBH$_3$ or NaBH(OAc)$_3$, more preferably NaBH$_4$, and crystallizing the crude product, preferably from a mixture comprising heptane, ethyl acetate and NEt$_3$ and obtaining a crystalline compound of formula (VIIb), preferably of formula (VIIb*).

Regarding the crystalline compound of formula (VIIb) and of formula (VIIb*) wherein R¹ is H they are preferably the crystalline forms (A) and (I), respectively as disclosed above.

According to a further embodiment the process further comprises preparing the salt of the crude product of the reduction step or of the crystalline solid.

According to a further embodiment, the process further comprises crystallizing the salt obtained.

Regarding the salt, the salt is preferably selected from the group consisting of hydrochloride salt and sulphate salt. Preferably, the salts are in a crystalline form.

Regarding the crystalline salts of compound of formula (VIIb*) wherein R¹ is H they are preferably in the crystalline forms (I-S) and (I-Cl) as disclosed below.

Regarding the crystallizing of compound (VIIb) or (VIIb*) preferably wherein R¹ is H, the crystallizing is preferably from a solvent, preferably an organic solvent, wherein preferably the organic solvent is selected from the group consisting of ethyl acetate, methanol, CH$_2$Cl$_2$, acetonitrile, isopropyl acetate, acetone, ethanol, isopropanol, toluene, butanol, isobutanol, t-butanol, tetrahydrofuran, methyltetrahydrofuran, cyclohexane and mixture thereof. Preferably, when ethyl acetate is used as the crystallization solvent of the compound of formula (VIIb*) the crystalline form (I) is obtained.

Regarding the crystallizing of the salt compound (VIIb) or (VIIb*) preferably wherein R¹ is H, the crystallizing is preferably from a solvent, preferably and organic solvent, wherein preferably the organic solvent is selected from the group consisting of ethyl acetate, methanol, CH$_2$Cl$_2$, acetonitrile, isopropyl acetate, acetone, ethanol, isopropanol, toluene, butanol, iso-butanol, t-butanol, tetrahydrofuran, methyltetrahydrofuran, cyclohexane and mixture thereof. Preferably, when the solvent is selected from the group consisting of ethyl acetate, methanol, CH$_2$Cl$_2$, and mixture thereof, preferably a mixture of methanol, CH$_2$Cl$_2$ is used as the crystallization solvent of the sulphate salt of the compound of formula (VIIb*) the crystalline form (I-S) is obtained. Preferably, when ethyl acetate is used as the crystallization solvent of the hydrochloride salt of the compound of formula (VIIb*) the crystalline form (I-Cl) is obtained.

Regarding the crystallizing of compound (VIIb) or (VIIb*) preferably wherein $R^1$ is H, the crystallizing is preferably carried out at a temperature in the range of from −30 to 70° C., more preferably in the range of from −10 to 50° C., most preferably in the range of from 10 to 30° C.

Regarding the crystallizing of the salt compound (VIIb) or (VIIb*) preferably wherein $R^1$ is H, the crystallizing is preferably carried out at a temperature in the range −30 to 70° C., more preferably in the range of from −10 to 50° C., most preferably in the range of from 10 to 30° C.

According to a further preferred embodiment, compound (A) has the structure (Ib), preferably (Ib*), with $R^1$ being H and with $R^2$ being $PG^2$. Thus, the present invention preferably relates to a process for the preparation of a compound and a compound obtained or obtainable by said process the compound having the structure

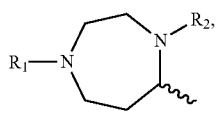

(Ib)

or being a pharmaceutically acceptable salt or solvate thereof, wherein (Ib) is preferably (Ib*)

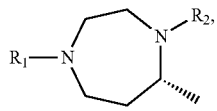

(Ib*)

and wherein $R^1$ is H and $R^2$ is $PG^2$, the process comprising
(a) providing a compound of formula (II),

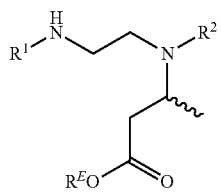

(II)

preferably (II*), wherein $R^E$ is selected from the group consisting of H, alkyl, aryl, alkylaryl, heteroaryl cycloalkyl and heterocycloalkyl, more preferably wherein $R^E$ is alkyl, more preferably wherein $R^E$ is methyl, ethyl or propyl, more preferably wherein $R^E$ is methyl,
(b) reacting the compound of formula (II) with a base, and reducing the resulting compound of formula (Ia), to give the compound of formula (Ib), with $R^1$ being H and with $R^2$ being $PG^2$, preferably (Ib*) with $R^1$ being H and with $R^2$ being $PG^2$.

Preferably, compound (Ib) with $R^1$ being H and with $R^2$ being $PG^2$, thus compound

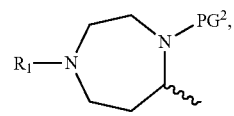

more preferably compound (Ib*) with $R^1$ being H and with $R^2$ being $PG^2$, thus compound

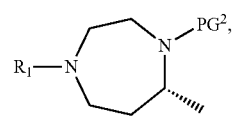

is used for the preparation of Suvorexant. Thus, the present invention also relates to the use of the compound of formula (Ib), preferably (Ib*), in which $R^1$ is H and $R^2$ is $PG^2$, for the preparation of compound (IX) (Suvorexant)

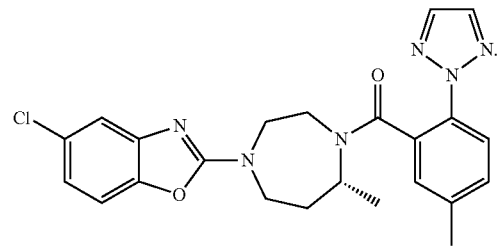

Further, the present invention relates to a process for the preparation of a compound of formula (IX) comprising
(A) providing a compound of formula (Ib) by a process comprising
   (a) providing a compound of formula (II),

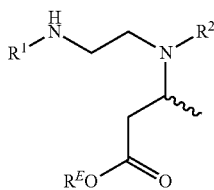

(II)

preferably (II*), wherein $R^E$ is selected from the group consisting of H, alkyl, aryl, alkylaryl, heteroaryl cycloalkyl and heterocycloalkyl, more preferably wherein $R^E$ is alkyl, more preferably wherein $R^E$ is methyl, ethyl or propyl, more preferably wherein $R^E$ methyl, wherein $R^1$ is H and $R^2$ is $PG^2$,
   (b) reacting the compound of formula (II) with a base, to give the compound of formula (Ia),

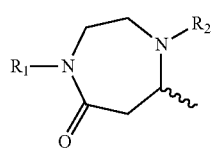

(Ia)

with R¹ being H and with R² being PG², preferably (Ia*) with R¹ being H and with R² being PG², and reducing the resulting compound of formula (Ia), preferably (Ia*).

(B) transforming the compound of step (A) into the compound of formula (IX).

Preferably, step (B) comprises
(c1) removal of the protecting group PG²,
(d1b) reacting the compound of formula (Ib) with R¹ and R² being H with a compound of formula

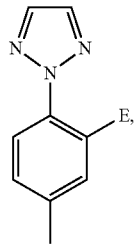

(XI)

wherein E is —COOH or a reactive carboxy group, to give a compound of formula (VIIb) in which R¹ is H

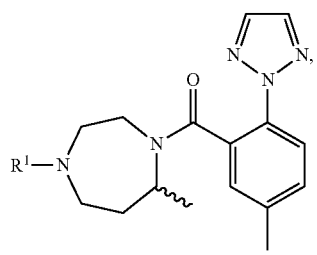

(VIIb)

preferably

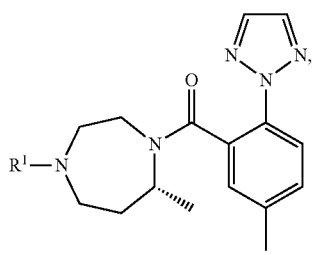

(VIIb*)

(f1) reacting the compound of formula (VIIb), preferably (VIIb*) with a compound of formula (XII)

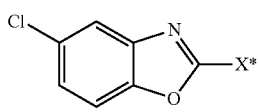

(XII)

wherein X* is a leaving group, preferably Cl.

In an embodiment (d1b) optionally comprises
(d1b-1) optionally preparing a salt of the compound of formula (VIIb) in which R¹ is H, preferably (VIIb*) in which R¹ is H and preferably wherein the salt is an hydrochloride salt or a sulphate salt, (d1b-2) optionally purifying the compound obtained in (d1b) or (d1b-1), wherein preferably purifying comprises crystallizing the compound obtained in (d1b) or (d1b-1), (d1b-3) optionally transforming the crystalline salt of (d1b-2) in the free base of formula (VIIb), preferably (VIIb*).

Preferably, in step (d1b-2), the crystalline form (A) or the crystalline form (I) is obtained. Preferably in step (d1b-2), the crystalline form (I-S) or the crystalline form (I-Cl) are obtained. Crystalline forms (A), (I), (I-S) and (I-Cl) are disclosed herein below.

The present invention further relates to a compound obtained or obtainable by said process.

According to a further preferred embodiment, compound (A) has the structure (Ia), preferably (Ia*), with R¹ being H and with R² being

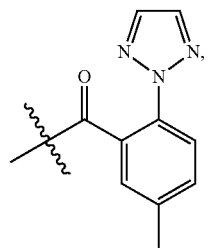

i.e. the structure (VIIa), preferably (VIIa*), with R¹ being H.

Thus, the present invention preferably relates to a process for the preparation of a compound, and a compound obtained or obtainable by said process, the compound having the structure (VIIa), preferably (VIIa*), with R¹ being H, the process comprising (a) providing a compound of formula (II),

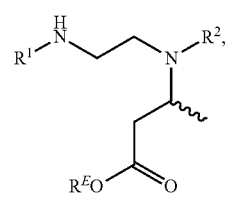

(II)

preferably (II*), wherein $R^E$ is selected from the group consisting of H, alkyl, aryl, alkylaryl, heteroaryl cycloalkyl and heterocycloalkyl, more preferably wherein $R^E$ is alkyl, more preferably wherein $R^E$ is methyl, ethyl or propyl, more preferably wherein $R^E$ is methyl, and wherein R² is

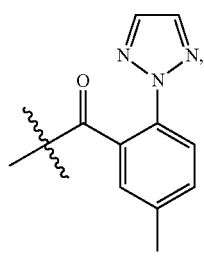

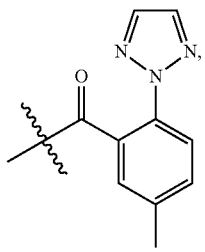

(b) reacting the compound of formula (II), preferably (II*), with a base to give the compound of formula (VIIa), preferably (VIIa*).

Preferably, compound (Vila), preferably (VIIa*), with $R^1$=H, is used for the preparation of compound (IX) (Suvorexant).

Thus, the present invention also relates to the use of a compound (VIIa), preferably (VIIa*), with $R^1$=H, for the preparation of compound (IX)

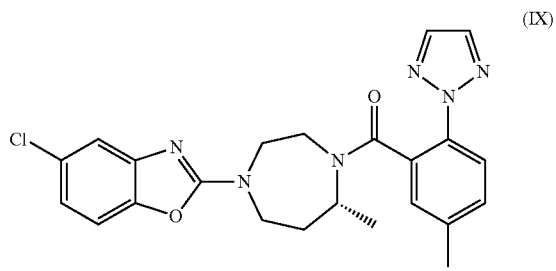 [SMILES: Cc1ccc(-n2nccn2)c(C(=O)N2CCN(c3nc4cc(Cl)ccc4o3)CC[C@H]2C)c1]

(IX)

Further, the present invention relates to a process for the preparation of a compound of formula (IX) comprising (A) providing a compound of formula (VIIa) by a process comprising (a) providing a compound of formula (II)

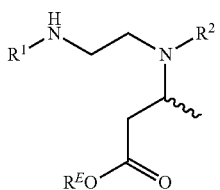

(II)

wherein $R^E$ is selected from the group consisting of H, alkyl, aryl, alkylaryl, heteroaryl, cycloalkyl and heterocycloalkyl, more preferably wherein $R^E$ alkyl, more preferably wherein $R^E$ methyl, ethyl or propyl, more preferably wherein $R^E$ methyl, and wherein $R^2$ is (b) reacting the compound of formula (II) with a base, to give the compound (Vila), preferably (VIIa*), with $R^1$=H, (B) transforming the compound of step (A) into the compound of formula (IX).

Preferably, step (B) further comprises (e1) reducing the compound to give a compound of formula (VIIb) in which $R^1$ is H, preferably (VIIb*) in which $R^1$ is H, (f1) reacting the compound of formula (VIIb), preferably (VIIb*), with a compound of formula (XII)

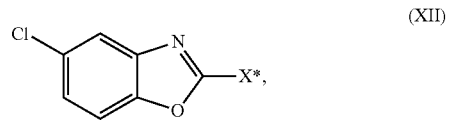

(XII)

wherein X* is a leaving group, preferably Cl,

In an embodiment, (e1) optionally comprises (e1-1) optionally preparing a salt of the compound of formula (VIIb) in which $R^1$ is H, preferably (VIIb*) in which $R^1$ is H and preferably wherein the salt is an hydrochloride salt or a sulphate salt, (e1-2) optionally purifying the compound obtained in (e1) or (e1-1), wherein preferably purifying comprises crystallizing the compound obtained in (e1) or (e1-1), (e1-3) optionally transforming the crystalline salt of (e1-2) in the free base of formula (VIIb), preferably (VIIb*).

Preferably, in step (e1-2), the crystalline form (A) or the crystalline form (I) is obtained. Preferably in step (e1-2), the crystalline form (I-S) or the crystalline form (I-Cl) are obtained. Crystalline forms (A), (I), (I-S) and (I-Cl) are disclosed herein below.

The present invention further relates to a compound obtained or obtainable by said process. Further, the present invention relates to a compound of formula (VIIb), preferably (VIIb*), as mentioned above. Further the present invention relates to the use of a compound (VIIb), preferably (VIIb*), as mentioned above.

According a further preferred embodiment, compound (A) has the structure (Ib), preferably (Ib*), with $R^1$ being H and with $R^2$ being

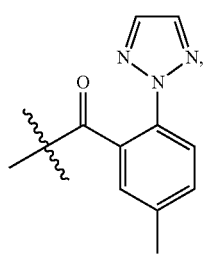 [SMILES: *C(=O)c1cc(C)ccc1-n1nccn1]

i.e. the structure (VIIb), preferably (VIIb*), with $R^1$ being H.

Thus, the present invention preferably relates to a process for the preparation of a compound, and a compound obtained or obtainable by said process, the compound having the structure (VIIa), preferably (VIIa*), with $R^1$ being H, the process comprising (a) providing a compound of formula (II),

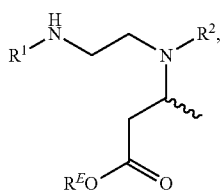

(II)

preferably (II*), wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, and wherein $R^2$ is

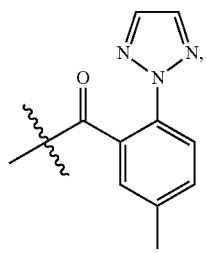

(b) reacting the compound of formula (II), preferably (II*), with a base, and reducing the resulting compound to give a compound of formula (VIIb), preferably (VIIb*).

In an embodiment, (b) optionally further comprises (b1-1) optionally preparing a salt of the compound of formula (VIIb) in which $R^1$ is H, preferably (VIIb*) in which $R^1$ is H and preferably wherein the salt is an hydrochloride salt or a sulphate salt, (b1-2) purifying the compound obtained in (b) or (b1-1), wherein preferably purifying comprises crystallizing the compound obtained in (b) or (b1-1), (b1-3) optionally transforming the crystalline salt of (b1-2) in the free base of formula (VIIb), preferably (VIIb*).

Preferably, in step (b1-2), the crystalline form (A) or the crystalline form (I) is obtained. Preferably, in step (b1-2), the crystalline form (I-S) or the crystalline form (I-Cl) are obtained. Crystalline forms (A), (I), (I-S) and (I-Cl) are disclosed herein below.

Preferably, compound (VIIb), preferably (VIIb*), with $R^1$=H, is used for the preparation of Suvorexant.

Thus, the present invention also relates to the use of compound (VIIb), preferably (VIIb*), with $R^1$=H, for the preparation of compound (IX)

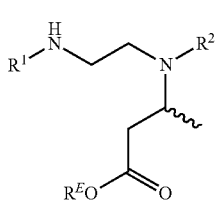

Further, the present invention relates to a process for the preparation of a compound of formula (IX) comprising (A) providing a compound of formula (VIIb) by a process comprising (a) providing a compound of formula (II), preferably (II*).

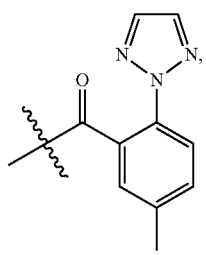

(II)

wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, and wherein $R^2$ is

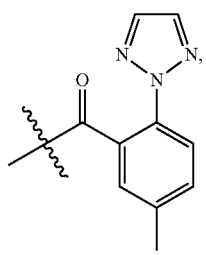

(b) reacting the compound of formula (II), preferably (II*), with a base to give the compound of formula (VIIa), preferably (VIIa*), and reducing the resulting compound to give a compound of formula (VIIb), preferably (VIIb*), (B) transforming the compound of step (A) into the compound of formula (IX).

In an embodiment, (b) optionally further comprises (b1-1) optionally preparing a salt of the compound of formula (VIIb) in which $R^1$ is H, preferably (VIIb*) in which $R^1$ is H and preferably wherein the salt is an hydrochloride salt or a sulphate salt, (b1-2) optionally purifying the compound obtained in (b) or (b1-1), wherein preferably purifying comprises crystallizing the compound obtained in (b) or (b1-1), (b1-3) optionally transforming the crystalline salt of (b1-2) in the free base of formula (VIIb), preferably (VIIb*).

Preferably, in step (b1-2), the crystalline form (A) or the crystalline form (I) is obtained. Preferably, in step (b1-2), the crystalline form (I-S) or the crystalline form (I-Cl) are obtained. Crystalline forms (A), (I), (I-S) and (I-Cl) are disclosed herein below.

Preferably, step (B) comprises (f1) reacting the compound of formula (VIIb), preferably (VIIb*), with a compound of formula (XII)

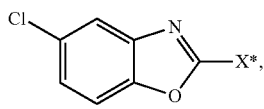
(XII)

wherein X* is a leaving group, preferably Cl.

The present invention further relates to a compound obtained or obtainable by said process.

According a further preferred embodiment, compound (A) has the structure (Ia), preferably (Ia*), with $R^1$ being $R^A$ and with $R^2$ being $PG^2$. Preferably, $R^A$ is

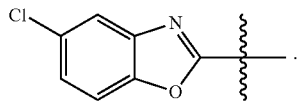 [SMILES: *c1nc2cc(Cl)ccc2o1]

Thus, the present invention preferably relates to a process for the preparation of a compound, and a compound obtained or obtainable by said process, the compound having the structure

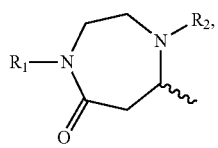
(Ia)

or being a pharmaceutically acceptable salt or solvate thereof, wherein (Ia) is preferably (Ia*)

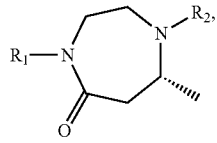
(Ia*)

and wherein $R^1$ is $R^A$ with $R^A$ being

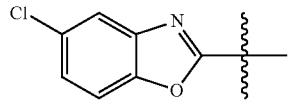 [SMILES: *c1nc2cc(Cl)ccc2o1]

and $R^2$ is $PG^2$, the process comprising (a) providing a compound of formula (II)

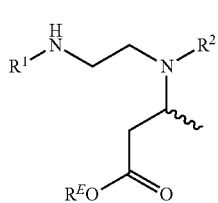
(II)

wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, wherein $R^1$ is $R^A$ with $R^A$ being

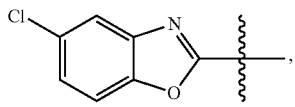 [SMILES: *c1nc2cc(Cl)ccc2o1]

and $R^2$ is $PG^2$, preferably the compound of formula (Ia*), wherein $R^1$ is $R^A$ with $R^A$ being

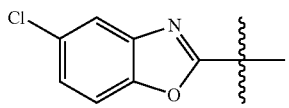 [SMILES: *c1nc2cc(Cl)ccc2o1]

and $R^2$ is $PG^2$, (b) reacting the compound of formula (II) with a base, to give the compound of formula (Ia),
wherein $R^1$ is $R^A$ with $R^A$ being

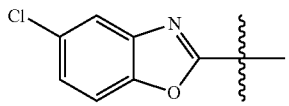 [SMILES: *c1nc2cc(Cl)ccc2o1]

and $R^2$ is $PG^2$, preferably the compound of formula (Ia*), wherein $R^1$ is $R^A$ with $R^A$ being

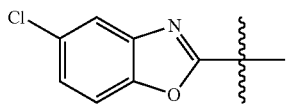 [SMILES: *c1nc2cc(Cl)ccc2o1]

and $R^2$ is $PG^2$.

The compound of formula (Ia) wherein $R^1$ is $R^A$ with $R^A$ being

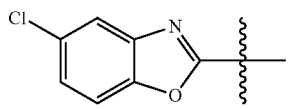 [SMILES: *c1nc2cc(Cl)ccc2o1]

and wherein $R^2$ is $PG^2$ is hereinunder and above referred to as compound (VIIIa)

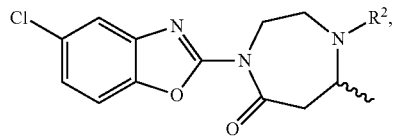
(VIIIa)

the respective single isomer as (VIIIa*)

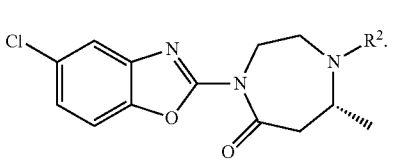
(VIIIa*)

Preferably, compound (VIIIa), more preferably compound (VIIIa*), is used for the preparation of Suvorexant. Thus, the present invention also relates to the use of compound (VIIIa), more preferably of compound (VIIIa*), for the preparation of Suvorexant

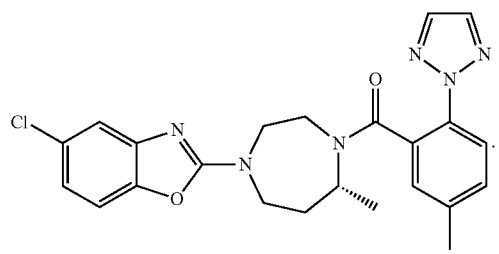 [SMILES: Cc1ccc(-n2nccn2)c(C(=O)N2CCN(c3nc4cc(Cl)ccc4o3)CC[C@H]2C)c1]

Further, the present invention relates to a process for the preparation of a compound of formula (IX) comprising
(A) providing a compound of formula (VIIIa) by a process comprising
  (a) providing the compound of formula (II),

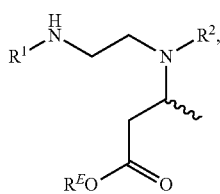
(II)

preferably (II*),
wherein $R^E$ is selected from the group consisting of H, alkyl, aryl, alkylaryl, heteroaryl cycloalkyl and heterocycloalkyl, more preferably wherein $R^E$ is alkyl, more preferably wherein $R^E$ is methyl, ethyl or propyl, more preferably wherein $R^E$ is methyl, wherein $R^1$ is $R^A$ with $R^A$ being

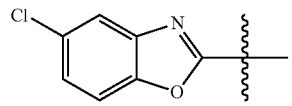

and $R^2$ is $PG^2$, preferably the compound of formula (Ia*), wherein $R^1$ is $R^A$ with $R^A$ being

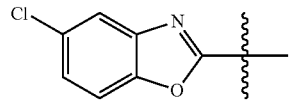 [SMILES: *c1nc2cc(Cl)ccc2o1]

and $R^2$ is $PG^2$,
  (b) reacting the compound of formula (II) with a base, to give the compound of formula (VIIIa), preferably (VIIIa*),
(B) transforming the compound of step (A) into the compound of formula (IX).
Preferably, step (B) further comprises
(c1) removal of the protecting group $PG^2$,
(d1) reacting the compound of formula (VIIIa), preferably the compound of formula (VIIIa*), with a compound of formula

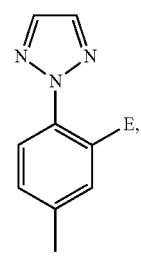
(XI)

wherein E is —COOH or a reactive carboxy group, to give a compound

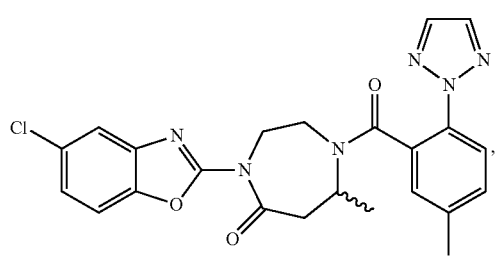 [SMILES: Cc1ccc(-n2nccn2)c(C(=O)N2CCN(c3nc4cc(Cl)ccc4o3)C(=O)CC2C)c1]

preferably a compound

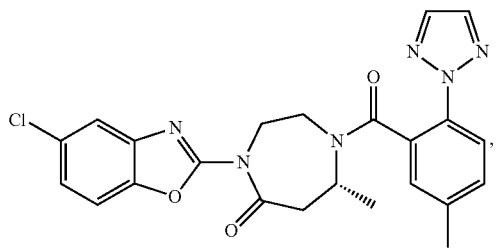 [SMILES: Cc1ccc(-n2nccn2)c(C(=O)N2CCN(c3nc4cc(Cl)ccc4o3)C(=O)C[C@H]2C)c1]

(e1) reducing the compound obtained in (f1).

The present invention further relates to a compound obtained or obtainable by said process. Further, the present invention relates to a compound of formula (VIIIa), preferably (VIIIa*), as mentioned above. Further the present invention relates to the use of a compound (VIIIa), preferably (VIIIa*), as mentioned above.

According to a further preferred embodiment, compound (A) has the structure (Ib), preferably (Ib*), with $R^1$ being $R^A$ and with $R^2$ being $PG^2$. Preferably, $R^A$ is

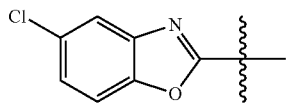 [SMILES: *c1nc2cc(Cl)ccc2o1]

Thus, the present invention preferably relates to a process for the preparation of a compound, and a compound obtained or obtainable by said process, the compound having the structure

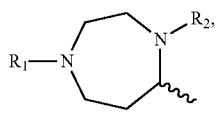

(Ib)

or being a pharmaceutically acceptable salt or solvate thereof, wherein (Ib) is preferably (Ib*)

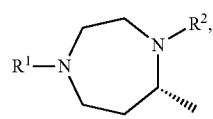

(Ib*)

and wherein $R^1$ is $R^A$ with $R^A$ being

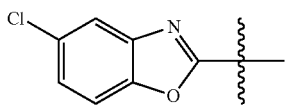 [SMILES: *c1nc2cc(Cl)ccc2o1]

and $R^2$ is $PG^2$, the process comprising (a) providing a compound of formula (II)

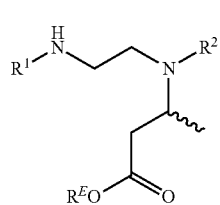

(II)

preferably (II*), wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, wherein $R^1$ is $R^A$ with $R^A$ being

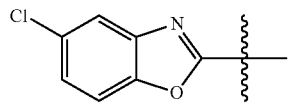 [SMILES: *c1nc2cc(Cl)ccc2o1]

and $R^2$ is $PG^2$, preferably the compound of formula (Ia*), wherein $R^1$ is $R^A$ with $R^A$ being

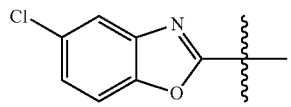

and $R^2$ is $PG^2$, (b) reacting the compound of formula (II) with a base, and reducing the compound to give the compound of formula (Ib), wherein $R^1$ is $R^A$ with $R^A$ being

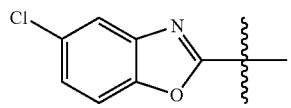 [SMILES: *c1nc2cc(Cl)ccc2o1]

and $R^2$ is $PG^2$, preferably the compound of formula (Ib*), wherein $R^1$ is $R^A$ with $R^A$ being

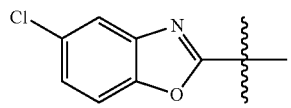 [SMILES: *c1nc2cc(Cl)ccc2o1]

and $R^2$ is $PG^2$.

The compound of formula (Ib) wherein $R^1$ is $R^A$ with $R^A$ being

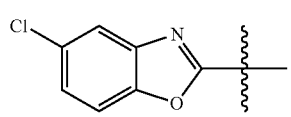 [SMILES: *c1nc2cc(Cl)ccc2o1]

and wherein $R^2$ is $PG^2$ is hereinunder and above referred to as compound (VIIIb)

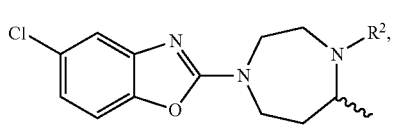
(VIIIb)

the respective single isomer as (VIIIb*)

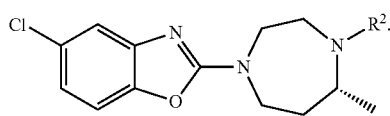
(VIIIb*)

Preferably, compound (VIIIb), more preferably compound (VIIIb*), is used for the preparation of compound (IX). Thus, the present invention also relates to the use of compound (VIIIb), more preferably of compound (VIIIb*), for the preparation of compound (IX).

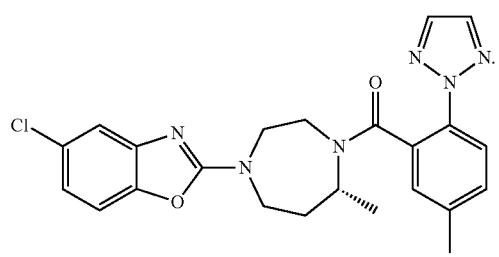 [SMILES: Cc1ccc(-n2nccn2)c(C(=O)N2CCN(c3nc4cc(Cl)ccc4o3)CC[C@H]2C)c1]

Further, the present invention relates to a process for the preparation of the compound of formula (IX) comprising
(A) providing a compound of formula (VIIIb) by a process comprising
  (a) providing a compound of formula (II), preferably (II*),

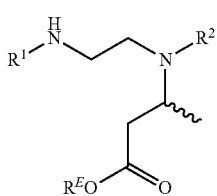
(II)

wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, wherein $R^1$ is $R^A$ with $R^A$ being

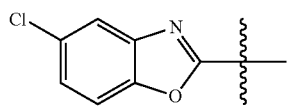 [SMILES: *c1nc2cc(Cl)ccc2o1]

and $R^2$ is $PG^2$, preferably the compound of formula (Ia*), wherein $R^1$ is $R^A$ with $R^A$ being

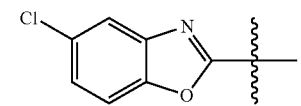

and $R^2$ is $PG^2$,
  (b) reacting the compound of formula (II), preferably (II*), with a base, to give the compound of formula (VIIIa), preferably (VIIIa*), and reducing the compound of formula (VIIIa), preferably (VIIIa*),
  to give the compound of formula (VIIIb), preferably (VIIIb*),
(B) transforming the compound of step (A) into the compound of formula (IX).
Preferably, step (B) further comprises
  (c1) removal of the protecting group $PG^2$,
  (d1b) reacting the compound of formula (VIIIb), preferably the compound of formula (VIIIb*), with a compound of formula

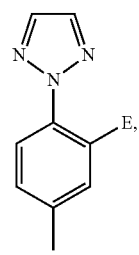
(XI)

wherein E is —COOH or a reactive carboxy group.

The present invention further relates to a compound obtained or obtainable by said process. Further, the present invention relates to a compound of formula (VIIIb), preferably (VIIIb*), as mentioned above. Further the present invention relates to the use of a compound (VIIIb), preferably (VIIIb*), as mentioned above.

According to a further preferred embodiment, compound (A) has the structure (Ia), preferably (Ia*), with $R^1$ being $R^A$ and with $R^2$ being $R^B$

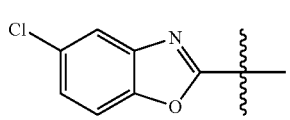 [SMILES: *c1nc2cc(Cl)ccc2o1]
($R^A$)

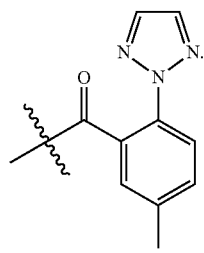
($R^B$)

Thus, the present invention preferably relates to a process for the preparation of a compound, and a compound obtained or obtainable by said process, the compound having the structure

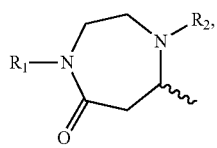
(Ia)

or being a pharmaceutically acceptable salt or solvate thereof, wherein (Ia) is preferably (Ia*)

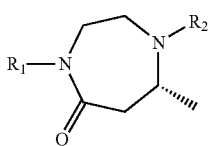
(Ia*)

and wherein $R^1$ is $R^A$ and $R^2$ is $R^B$,

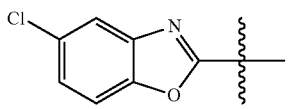
($R^A$)

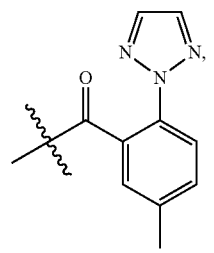
($R^B$)

the process comprising
(a) providing a compound of formula (II)

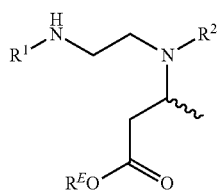
(II)

and wherein $R^1$ is $R^A$ and $R^2$ is $R^B$,

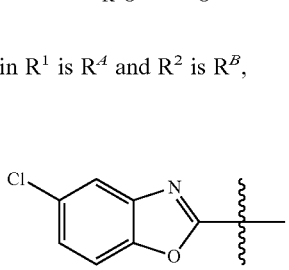
($R^A$)

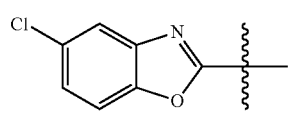
($R^B$)

(b) reacting the compound of formula (II) with a base, to give the compound of formula (Ia), and wherein $R^1$ is $R^A$ and $R^2$ is $R^B$,

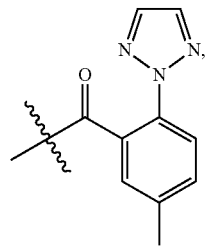
($R^A$)

($R^B$)

The compound of formula (Ia) wherein $R^1$ is $R^A$ and $R^2$ is $R^B$, ($R^A$)

($R^B$)

is hereinunder and above referred to as compound (VIIIa)

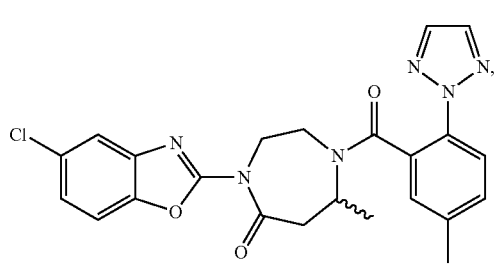
(IXa)

the respective single isomer as (IXa*)

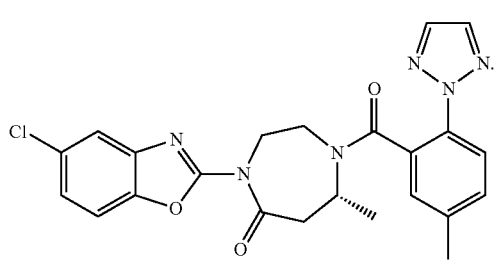
(IXa*)

Preferably, compound (IXa), more preferably compound (IXa*), is used for the preparation of compound (IX). Thus, the present invention also relates to the use of compound (IXa), more preferably compound of (IXa*), for the preparation of compound (IX)

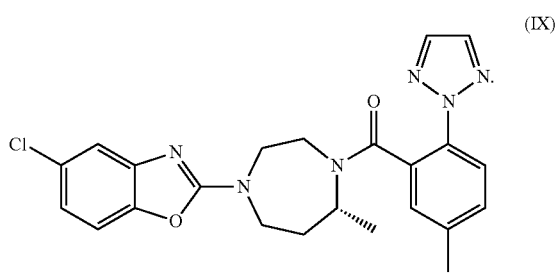 [SMILES: Cc1ccc(-n2nccn2)c(C(=O)N2CCN(c3nc4cc(Cl)ccc4o3)CC[C@H]2C)c1]
(IX)

Further, the present invention relates to a process for the preparation of compound IX comprising (A) providing a compound of formula (IXa*) by a process comprising (a) providing a compound of formula (II), preferably (II*),

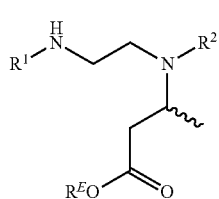
(II)

wherein $R^1$ is $R^A$ and $R^2$ is $R^B$,

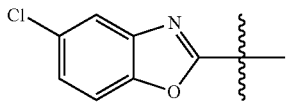
($R^A$)

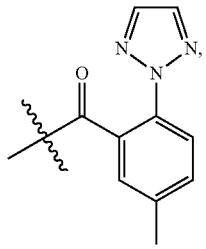
($R^B$)

(b) reacting the compound of formula (II), preferably (II*), with a base,
to give the compound of formula (IXa), preferably (IXa*), (B) transforming the compound of step (A) into the compound of formula (IX).

Preferably, step (B) further comprises
(e1) reducing the compound.

The present invention further relates to a compound obtained or obtainable by said process. Further, the present invention relates to a compound of formula (IXa), preferably (IXa*), as mentioned above. Further the present invention relates to the use of a compound (IXa), preferably (IXa*), as mentioned above.

Step (c1): Removal of the Protecting Group $PG^2$

In step (c1) mentioned above, the protecting group $PG^2$ is removed. The way of removing the protecting group $PG^2$ depends on the protecting group used. Suitable methods are known to those skilled in the art. Preferably, in case the protecting group $R^2$ is a Cbz protecting group, the removal of $PG^2$ is carried out under reductive conditions. More preferably, the removal is carried out with hydrogen and a metal catalyst, preferably a palladium catalyst, more preferably, the protecting group is removed with Pd/C. The removal of group $PG^2$ may be carried out in any suitable solvent known to those skilled in the art. Preferably, the reaction is carried out in an organic solvent, more preferably in a solvent selected from the group consisting of methanol, ethanol, iPrOH, nPrOH, EtOAc, iPrOAc and mixtures of two or more thereof.

Preferably, the removal of group $PG^2$ is carried out at a temperature in the range of from 0° C. to 100° C., more preferably in the range of from 10° C. to 70° C., more preferably at room temperature 20° C. to 50° C. During the reaction, the temperature may be varied or held essentially constant.

In case hydrogen is used, the reaction is preferably carried out at a pressure in the range of from 1 to 4 bar, more preferably, 1.0 to 2.5 bar.

The compound is preferably allowed to react for a time in the range of from 10 min to 180 min, more preferably in the range of from 20 to 120 min, more preferably in the range of from 30 to 60 min.

Step (d1):

In step (d1), the respective compound is reacted, i.e. coupled, with a compound of formula (XI), wherein E is —COOH or a reactive carboxy group, to give a compound of formula (VIIa) in which $R^1$ is H, preferably a compound of formula (VIIa*) in which $R^1$ is H.

The term "reactive carboxy group" as used in this context of the present invention is intended to mean an activated carboxylic acid derivative that reacts readily with electrophilic groups, such as an NH group, optionally in the presence of a suitable base, in contrast to those groups that require a further catalyst, such as a coupling reagent, in order to react. The term "activated carboxylic acid derivative" as used herein preferably refers to acid halides, such as acid chlorides, and also refers to activated ester derivatives including, but not limited to, formic and acetic acid derived anhydrides, anhydrides derived from alkoxycarbonyl halides, such as isobutyloxycarbonylchloride and the like, isothiocyanates or isocyanates, anhydrides derived from reaction of the carboxylic acid with N,N'-carbonyldiimidazole and the like, and esters derived from activation of the corresponding carboxylic acid with a coupling reagent. Such coupling reagents include, but are not limited to, HATU (O-(7-azabenzotriazol-1-yl)-N,N,N',N'-tetramethyluronium hexafluorophosphate); HOAt, HBTU (O-benzotriazol-1-yl)-N,N,N',N'-tetramethyluronium hexafluorophosphate); TBTU (2-(1H-benzotriazol-1-yl)-1,1,3,3-tetramethyluronium hexafluorophosphate); TFFH (N,N',N'',N'''-tetramethyluronium-2-fluoro-hexafluorophosphate); BOP (benzotriazol-1-yloxytris(dimethylamino)phosphonium hexafluorophosphate); PyBOP (benzotriazol-1-yl-oxy-trispyrrolidino-phosphonium hexafluorophosphate; EEDQ (2-ethoxy-1-ethoxycarbonyl-1,2-dihydro-quinoline); DCC (dicyclohexylcarbodiimide); DIPCDI (diisopropylcarbodiimide); HOBt (1-hydroxybenzotriazole); NHS (N-hydroxysuccinimide); MSNT (1-(mesitylene-2-sulfonyl)-3-nitro-1H-1,2,4-triazole); aryl sulfonyl halides, e.g. triisopropylbenzenesulfonyl chloride, EDC (1-ethyl-3-(3-dimethylaminopropyl) carbodiimide hydrochloride, CDC (1-cyclohexyl-3-(2-morpholinoethyl)carbodiimide), Pyclop, T3P, CDI, Mukayama's reagent, HODhbt, HAPyU, TAPipU, TPTU, TSTU, TNTU, TOTU, BroP, PyBroP, BOI, TOO, NEPIS, BBC, BDMP, BOMI, AOP, BDP, PyAOP, TDBTU, BOP-Cl, CIP, DEPBT, Dpp-Cl, EEDQ, FDPP, HOTT, TOTT, PyCloP.

In case E is —COOH, the reaction is preferably carried out in the presence of a catalyst, such as a coupling reagent, or a reagent that forms in situ an acid chlorid with E, such as oxalyl chloride, and preferably further in the presence of a base. Preferably, in this case, the coupling reagent is selected from the group consisting of HATU (O-(7-azabenzotriazol-1-yl)-N,N,N',N'-tetramethyluronium hexafluorophosphate); HOAt, HBTU (O-benzotriazol-1-yl)-N,N,N',N'-tetramethyluronium hexafluorophosphate); TBTU (2-(1H-benzotriazol-1-yl)-1,1,3,3-tetramethyluronium hexafluorophosphate); TFFH (N,N',N'',N'''-tetramethyluronium-2-fluoro-hexafluorophosphate); BOP (benzotriazol-1-yloxytris(dimethylamino)phosphonium hexafluorophosphate); PyBOP (benzotriazol-1-yl-oxy-trispyrrolidino-phosphonium hexafluorophosphate; EEDQ (2-ethoxy-1-ethoxycarbonyl-1,2-dihydro-quinoline); DCC (dicyclohexylcarbodiimide); DIPCDI (diisopropylcarbodiimide); HOBt (1-hydroxybenzotriazole); NHS (N-hydroxysuccinimide); MSNT (1-(mesitylene-2-sulfonyl)-3-nitro-1H-1,2,4-triazole); aryl sulfonyl halides, e.g. triisopropylbenzenesulfonyl chloride, EDC (1-ethyl-3-(3-dimethylaminopropyl) carbodiimide hydrochloride, CDC (1-cyclohexyl-3-(2-morpholinoethyl)carbodiimide), Pyclop, T3P, CDI, Mukayama's reagent, HODhbt, HAPyU, TAPipU, TPTU, TSTU, TNTU, TOTU, BroP, PyBroP, BOI, TOO, NEPIS, BBC, BDMP, BOMI, AOP, BDP, PyAOP, TDBTU, BOP-Cl, CIP, DEPBT, Dpp-Cl, EEDQ, FDPP, HOTT, TOTT, PyCloP.

More preferably, E is a reactive carboxy group, in particular —C(=O)R$^5$, wherein R$^5$ is selected from the group consisting of —O-Alkyl, —OH, —H and X with X being the leaving group of the activated ester group —C(=O)—X, preferably wherein X is selected from the group consisting of

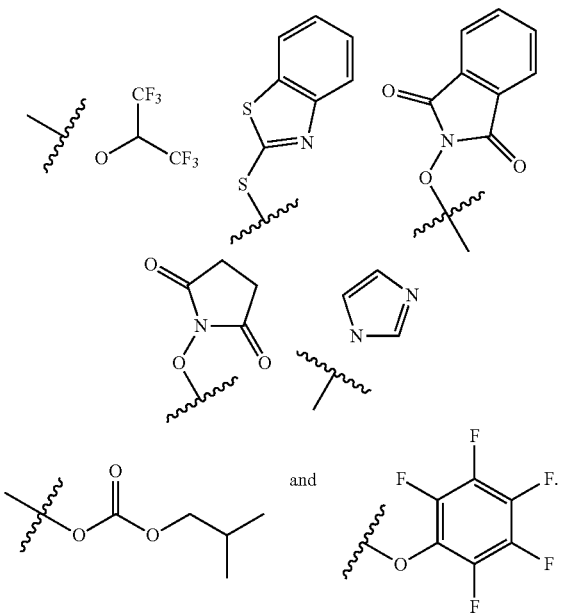

According to an alternative embodiment, E is —COOH, as mentioned above, and the reaction includes the addition of a coupling reagent or a reagent that forms in situ an acid chlorid with E, such as oxalyl chloride.

The coupling with E being —COOH or a reactive carboxy group, is preferably carried out in the presence of a suitable base, preferably an organic base, most preferably an amino group comprising base, most preferably a base selected from the group consisting of diisopropylamine (DIEA), triethylamine (TEA), N-methylmorpholine, N-methylimidazole, 1,4-diazabicyclo[2.2.2]octane (DABCO), N-methylpiperidine, N-methylpyrrolidine, 2,6-lutidine, collidine, pyridine, 4-dimethylaminopyridine, 1,8-diazabicyclo[5.4.0]undec-7-ene (DBU). As regards the reaction conditions used in this coupling step, preferably, the reaction is carried out in an organic solvent, such as N-methyl pyrrolidone (NMP), dimethyl sulfoxide (DMSO), acetonitrile, acetone, dimethyl acetamide (DMA), dimethyl formamide (DMF), formamide, tetrahydrofuran (THF), 1,4-dioxane, diethyl ether, tert.-butyl methyl ether (MTBE), dichloromethane (DCM), chloroform, tetrachloromethane and mixtures of two or more thereof. More preferably, the reaction is carried out in dichloromethane.

The temperature of the coupling reaction is preferably in the range of from 0 to 100° C., more preferably in the range of from 5 to 50° C., and especially preferably in the range of from 15 to 30° C. During the course of the reaction, the temperature may be varied, preferably in the above given ranges, or held essentially constant.

Step (d1a):

In step (d1a), the respective compound is reacted, i.e. coupled, with a compound of formula (XI), wherein E is —COOH or a reactive carboxy group. With respect to details regarding group E and preferred reaction conditions, reference is made to the details presented above and below with respect to step (d1) which equally apply for step (d1a).

Step (e1): Reducing the compound of formula (VIIb):

In step (e1), the compound is reduced. In this case, a reduction of the carbonyl group is thus carried out. The reduction is preferably carried out as described with respect to step (b3) described hereunder and above. Preferably, the reduction is carried out in an organic solvent, more preferably in a solvent selected from the group consisting of methanol, ethanol, nPrOH, i-PrOH, THF, 2-MeTHF, MTBE, DIPET, toluene, acetonitrile, $CH_2Cl_2$ and mixtures of two or more thereof.

Preferably, step (b3) is carried out at a temperature in the range of from −20° C. to 110° C.

Preferably, step (e1) is carried out at a temperature in the range of from −20° C. to 110° C.

Preferably, in step (e1, the compound is reduced by reaction with a reducing agent selected from the group consisting of $NaBH_4$, $NaCNBH_3$, $NaBH(OAc)_3$, $LiAlH_4$, $LiBH_4$ and $H_2$ in the presence of transition metals, wherein the transition metal is preferably selected from the group consisting of IR, Pt, Fe, Rh, Pd, Re, Ru, Ni and Co. More preferably, the reducing agent is selected from the group consisting of $NaBH_4$, $NaCNBH_3$, $NaBH(OAc)_3$, $LiAlH_4$ and $LiBH_4$, more preferably the reducing agent is $NaBH_4$, $NaCNBH_3$ or $NaBH(OAc)_3$, more preferably $NaBH_4$.

Step (f1):

In step (f1), the respective compound is reacted with a compound of formula (XII)

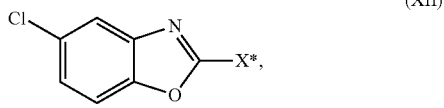

(XII)

wherein X* is a leaving group. The term leaving group is denoted to encompass any group that departs upon reaction of compound (XII) with an amine. Preferred leaving groups are —Cl, —S, —SMe, —SEt or —Br, in particular —Cl or —Br.

Preferably, the reaction is carried out in an organic solvent, more preferably in a solvent selected from the group consisting of dichloromethane, DMF, DMSO, NMP, methanol, ethanol, propanol, isopropanol, butanol, s-butanol, t-butanol, tetrahydrofuran, 2-methyltetrahydrofuran, methyltert-butylether, diethylether, diisopropylether, toluene, acetonitrile and mixtures of two or more thereof.

Preferably, the reaction is carried out at a temperature in the range of from 0 to 80° C., more preferably in the range of from 10 to 50° C., more preferably in the range of from 20 to 35° C., more preferably at room temperature. During the reaction, the temperature may be varied or held essentially constant.

The compounds are preferably allowed to react for a time in the range of from 10 min to 72 h, more preferably in the range of from 30 min to 24 h, more preferably in the range of from 1 h to 12 h.

It is to be understood that after any one of the above-mentioned steps it is conceivable that the reaction mixture obtained is subjected to a suitable work-up, such as an isolation of the respective compound. Such working up may comprise one or more stages wherein preferably at least one stage comprises purification, such as an extraction and/or a precipitation and/or filtration and/or chromatography or the like. Alternatively, some reactions may be carried out with the crude intermediate products or even in situ.

Steps (b1-1), (e1-1)(d1b1)

In steps (b1-1), (e1-1) (d1-b1) a salt of the compound of formula (VIIb) in which $R^1$ is H, preferably (VIIb*) in which $R^1$ is H and preferably wherein the salt is an hydrochloride salt or a sulphate salt is prepared.

Steps (b1-2), (e1-2) (d1b-2)

In steps (b1-2), (e1-2) (d1-b2) the compound obtained in (b), (e1), (d1b), (b1-1), (e1-1), (d1b-1) is purified. Preferably the purifying comprises crystallizing the compound obtained (b), (e1), (d1b), (b1-1), (e1-1), (d1b-1). Any method suitable for purifying and crystallizing is according to the invention.

Preferably, the crystallizing is carried out in a solvent selected from the group consisting of ethyl acetate, methanol, $CH_2Cl_2$, acetonitrile, isopropyl acetate, acetone, ethanol, isopropanol, toluene, butanol, isobutanol, t-butanol, tetrahydrofuran, methyltetrahydrofuran, cyclohexane and mixture thereof, wherein the solvent is preferably selected from the group consisting of ethyl acetate, methanol, $CH_2Cl_2$ and a mixture thereof.

Regarding the temperature of the crystallization process there is no specific limitation provided that the crystalline form is obtained. Preferably the temperature is in the range of from −30 to 70° C., more preferably in the range of from 10 to 50° C., even more in the range of from 10 to 30° C.

Steps (b1-3), (e1-3) (d1b-3)

In steps (b1-3), (e1-3) (d1-b3) the salt of (b1-2), (e1-2) (d1b-2) or the crystalline salt of (b1-2), (e1-2) (d1b-2) is transformed in the free base of formula (VIIb), preferably (VIIb*) according to methods known in the art.

Step (a)

The compound of formula (II) may be provided by any suitable method known to those skilled in the art.

Preferably, compound (II) provided in step (a) according to the invention comprises (a1) reacting a compound of formula (III)

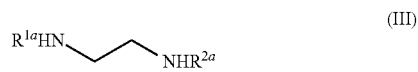

(III)

with a compound of formula (IV)

(IV)

to give a compound of formula (V)

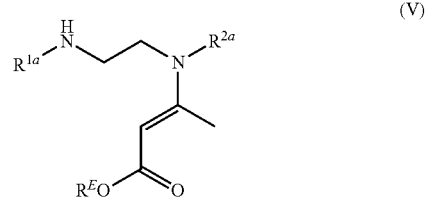

(V)

wherein at each occurrence $R^{1a}$ is H, $PG^1$, $R^4$ or $PG^{1a}$ and wherein $R^{2a}$ is H, $PG^2$, $R^B$ or $PG^{2a}$ and wherein $PG^{1a}$ and $PG^{2a}$ are, independently of each other, suitable protecting groups and $R^E$ is as defined above, (a2) optionally purifying the compound of formula (V),
(a3) reducing the compound of formula (V),
(a4) optionally replacing $R^{2a}$ and/or $R^{1a}$ with $R^1$ and/or $R^2$, to give the compound of formula (II).

Compound (II) and Compound (II*)

The compound of formula (II) provided in step (a) has the structure

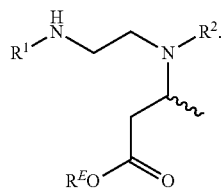

Residue $R^E$

As described above, $R^E$ is selected from the group consisting of H, alkyl, aryl, alkylaryl, heteroaryl cycloalkyl and heterocycloalkyl, more preferably $R^E$ is selected from the group consisting of alkyl, aryl, alkylaryl, heteroaryl cycloalkyl and heterocycloalkyl, more preferably $R^E$ is alkyl, more preferably $R^E$ is methyl, ethyl or propyl, more preferably $R^E$ methyl.

The structure

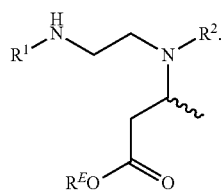

means that compound (II) has either the structure (II*)

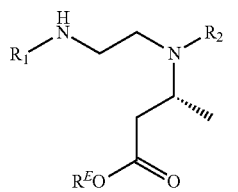

or consists of a mixture of

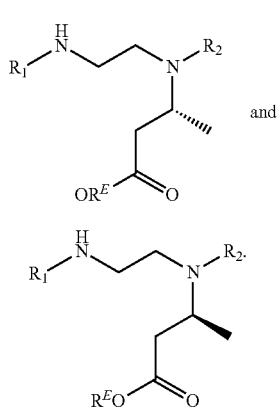

Alternatively, in step (a), the compound of formula (II*) is provided, thus the "single (isolated) isomer" with R configuration. The term "single isomer" in this context is denoted to mean that the compound of formula (II*) comprises less than 1% by weight of compound (II), preferably less than 0.5% by weight, more preferably less than 0.1% by weight, more preferably less than 0.05% by weight, more preferably less than 0.01% by weight, more preferably essentially no, more preferably no compound of formula (II) based on the total weight of (II*) and (II**).

In case the compound of formula (II*) is provided in step (a), the provision preferably either comprises a chiral resolution step or an enantioselective reaction step, such as enantioselective reduction of the double bond present in compound (V).

The chiral resolution may be carried out by any suitable method known to those skilled in the art, such as resolution by crystallization or by chiral chromatography, such as chiral HPLC. Preferably, the chiral resolution during step (a) is carried out by crystallization employing an optical pure resolving agent, preferably an optical pure chiral acid. Preferably, the chiral resolution of compound (II), if carried out, is carried out with a tartaric acid as chiral acid, preferably with tartaric acid.

Preferably, the provision in step (a) comprises the steps (a1) to (a4), as mentioned above.

Step (a3)

In step (a3), the compound of formula (V) is reduced to give a compound having the structure

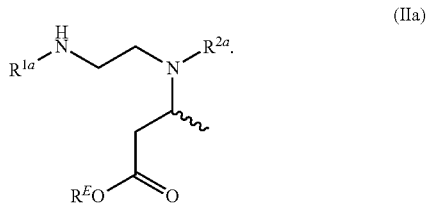

Thus, compound of formula (IIa), is prepared by a process, the process comprising steps (a1) to (a3) as disclosed above.

In case the reduction is carried out in a non-stereoselective manner, compound (IIa) consists of a mixture of (IIa*) and (IIa**) as shown below

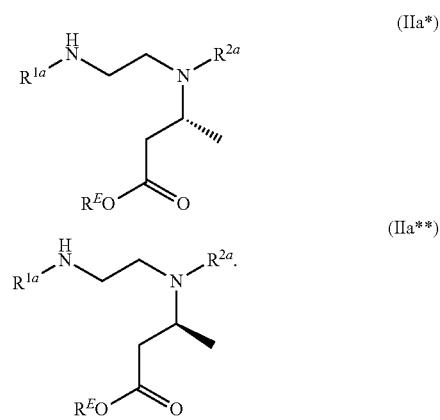

The reduction may be carried out by any suitable manner known to those skilled in the art. Preferably, a metal catalyst and hydrogen is used. The metal catalyst is preferably selected from the group consisting of a catalyst comprising Pd, Fe, Ir, Rh or a mixture of two or more thereof. Preferably, the catalyst comprises Pd and/or Fe and/or Rh, wherein the Fe, if present, is preferably present as part of a catalyst ligand.

The reaction is preferably carried out at a hydrogen pressure in the range of from 1 to 25 bar, more preferably, 2.5 to 10 bar. During the reaction, the pressure may be varied or held essentially constant.

Preferably, the reaction is carried out at a temperature in the range of from 10 to 100° C., more preferably in the range of from 20 to 60° C., more preferably at 40 to 60 C. During the reaction, the temperature may be varied or held essentially constant.

The reaction may be carried out in any suitable solvent known to those skilled in the art. Preferably, the cyclization reaction is carried out in an organic solvent, more preferably in a solvent selected from the group consisting of methanol, ethanol, trifluoroethanol (TFE), dichloromethane, DMF, DMSO, NMP, methanol, ethanol, propanol, isopropanol, butanol, s-butanol, t-butanol, tetrahydrofuran, 2-methyltetrahydrofuran, methyltertbutylether, diethylether, diisopropylether, toluene, acetonitrile and mixtures of two or more thereof. Preferably, the solvent is methanol or TFE.

According to one preferred embodiment, the catalyst is a palladium catalyst, more preferably Pd/C. In case of Pd/C, the reaction is preferably carried out in a non-stereoselective manner. The term "non-stereoselective manner" is denoted to mean that a racemic mixture of compounds (IIa*) and (IIa**) is obtained. Thus, the present invention also relates to a process, as described above, wherein step (a) comprises the steps (a1) to (a4), as described above, and wherein in step (a3), the compound is reduced with Pd/C.

It is to be understood that in case in step (a) a mixture of (II*) and (II**) is provided, compound (IIa) also consists of a racemic mixture, i.e. a mixture of the compounds (IIa*) and (IIa**)

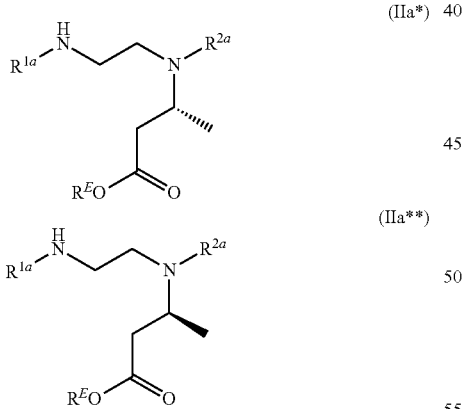

$R^{1a}$ and $R^1$

As mentioned above, $R^{1a}$ is H, $PG^1$, $R^A$ or $PG^{1a}$, and wherein $PG^{1a}$ and $PG^{2a}$ are, independently of each other, suitable protecting groups. Preferred protecting groups for $PG^{1a}$ include, but are not limited to, carbamates, such as Boc (t-butyloxycarbonyl, Cbz (carboxybenzyl), Fmoc (fluorenylmethyloxycarbonyl), Alloc (allyloxycarbonyl), methyl and ethyl carbamates; trityl, benzyl, benzylidene, tosyl and the like; cyclic imide derivatives, such as succinimide and phthalimide; amides, such as formyl, (un)substituted acetyl, and benzoyl; and trialkyl silyl groups, such as t-butyldimethylsilyl and triisopropylsilyl. Particularly preferred amino-protecting groups include Boc, Cbz, Fmoc, benzyl, acetyl, benzoyl, trityl and the like. Most preferably, $PG^{1a}$ is a Boc group or a Cbz group, more preferably Boc.

Preferred protecting groups for $PG^{2a}$ include, but are not limited to, carbamates, such as Boc (t-butyloxycarbonyl, Cbz (carboxybenzyl), Fmoc (fluorenylmethyloxycarbonyl), Alloc (allyloxycarbonyl), methyl and ethyl carbamates; trityl, benzyl, benzylidene, tosyl and the like; cyclic imide derivatives, such as succinimide and phthalimide; amides, such as formyl, (un)substituted acetyl, and benzoyl; and trialkyl silyl groups, such as t-butyldimethylsilyl and triisopropylsilyl. Particularly preferred amino-protecting groups include Boc, Cbz (CBZ), Fmoc, benzyl, acetyl, benzoyl, trityl and the like. Most preferably, $PG^{2a}$ is a Boc group or a Cbz group, more preferably Cbz.

It is to be understood that $R^{1a}$ may be different from $R^1$ or may be the same. Similarly, $R^{2a}$ may be different from $R^2$ or may be the same. In case $R^1$ differs from $R^{1a}$ or in case $R^2$ differs from $R^{2a}$ or in case both $R^{1a}$ and $R^{2a}$ differ from $R^{1a}$ and $R^{2a}$, respectively, step (a4) is carried out. In case $R^1$ is equal to $R^{1a}$ and $R^2$ is equal to $R^{2a}$, step (a4) is omitted.

It is thus to be understood that compound (IIa) may correspond to compound (II), compound (IIa*) may correspond to (II*) and compound (IIa) may correspond to (II) in case $R^{1a}$ is equal to $R^1$ and in case $R^2$ is equal to $R^{2a}$.

In case $R^{1a}$ is different from $R^1$ and/or $R^{2a}$ is different from $R^2$, $R^{1a}$ and/or $R^{2a}$ is transformed in step (a4) to $R^1$ and $R^2$, wherein this transformation may be carried out in one or in multiple steps, to give compound (II) or (II*), respectively. It is to be understood that in case (II) corresponds to (IIa) or (II*) corresponds to (IIa**), step (a4) is omitted.

In case in step (a) a compound having the structure (II*) is provided as single (isolated) isomer, as mentioned above, step (a) preferably comprises
 a chiral resolution of the compound of formula (IIa) to give the compound of formula (IIa*),
 a chiral resolution of the compound of formula (II) to give the compound of formula (II*), and/or
 an enantioselective reduction in step (a3) to give the compound of formula (IIa*) or (II*, respectively.

Chiral Resolution of the Compound of Formula (II)

As mentioned above, compound (II) may comprise a mixture of compounds (II*) and (II")

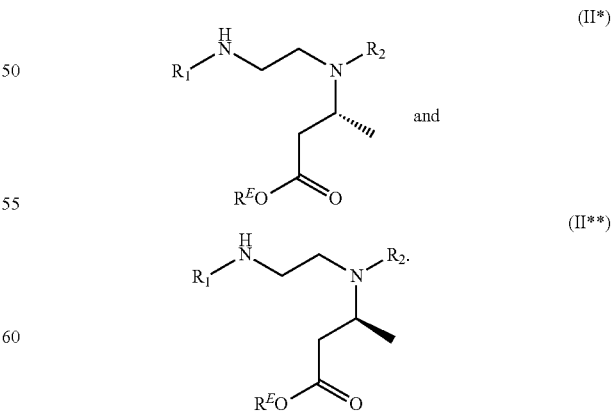

In this case, a chiral resolution of (II) may be carried out. More preferably, in case a chiral resolution is carried out at this stage, $R^2$ is H, and $R^1$ is Boc. $R^E$ is preferably methyl.

Preferably, the compound (II) contains of from 20 to 75% by weight of the compound of formula (II*) based on the total weight of the sum of (II*) and (II**). This mixture is then resolved by chiral resolution to finally give, optionally after further steps, the compound (II*).

Preferably, this is carried out by (i) adding a single stereoisomer of a chiral acid and precipitating, preferably crystallizing, a chiral acid salt (S) of compound (II), thereby obtaining a mixture comprising the precipitated, preferably crystallized, tartaric acid salt (S) and the solvent, (ii) preferably separating the precipitated, preferably crystallized, chiral acid salt (S) of the compound of formula (II) from the mixture obtained in (i), wherein the chiral acid salt (S) contains at least 80% by weight of the chiral acid salt of the compound of formula (II*) based on the total weight of the chiral acid salt of the compound of formula (II), (iii) converting the chiral acid salt (S) to the free base.

Preferably, in step (i), upon addition of the chiral acid in a suitable solvent, a chiral acid salt (S*) of at least part of the compound of formula (II) is formed and at least part of this chiral acid salt (S*) formed is precipitated, preferably crystallized, thereby obtaining a mixture comprising the precipitated, preferably crystallized, tartaric acid salt (S) and the solvent.

The chiral acid is preferably tartaric acid or a tartaric acid derivative selected from the group consisting of Ditoluoyl tartaric acid, Dibenzoyl tartaric acid, Dianisoyl tartaric acid, Dibenzoyl tartaric acid mono(dimethylamide) and a mixture of two or more thereof, more preferably, the chiral acid is tartaric.

Step (i)

The compound of formula (II) employed in (i) contains of from 20 to 75% by weight, more preferably of from 40 to 60% by weight, of the compound of formula (II*) based on the total weight of the sum of (II*) and (II**).

In step (i), at least part of the compound of formula (II) is transformed into the corresponding chiral acid salt, preferably tartaric acid salt (S*). The chiral acid salt (S*) contains the chiral acid salt of the compound of formula (II*), e.g. in an amount in the range of from 1 to 80% by weight, such as in the range of from 10 to 70% by weight, or in the range of from 30 to 60% by weigh, or in the range of from 45 to 55% by weight, based on the total amount of the chiral acid salt (S*).

Subsequently, at least part of (S*) is precipitated, preferably crystallized. This is preferably achieved by contacting (treating) the compound of formula (II) in a suitable solvent with the chiral acid. Thereby, a mixture comprising the crystallized chiral acid salt (S) of the compound of formula (II*) and the solvent is formed. As mentioned above, the precipitated, preferably crystallized, tartaric acid salt (S) of the compound of formula (II) contains at least 80% by weight of chiral acid salt of the compound of formula (II*) based on the total weight of the chiral acid salt of the compound of formula (II).

It is to be noted that the mixture obtained in step (i) may comprise further compounds, in particular non crystalline forms of the compound of formula (II) and salts thereof. Preferably, the mixture obtained in (i) comprises non-crystalline forms of the compound of formula (II**) and chiral acids salts thereof.

The chiral acid salt (S*) of the compound of formula (II) is denoted to encompass all chiral acid salts of compound (II) formed in step (i) including the chiral acid salt (S) which precipitates as well as all chiral acid salts formed which remain dissolved (S*—S). Thus, the chiral acid salt (S) may comprise a mixture of chiral acid salt of compounds of formula (II*) and (II**).

As to the solvent used in step (i), any suitable organic solvent in which the compound of formula (II) is sufficiently soluble may be used. In particular, the solvent is selected from the group consisting of EtOH, i-PrOH, nPrOH, acetone, toluene, MTBE, $CH_2Cl_2$, ethyl acetate, acetone, isopropanol, methanol, water, formic acid ethyl ester, isopropyl acetate, propyl acetate, butyl acetate, acetonitrile, tetrahydrofuran, dichloromethane, methylisobutylketone, toluene, hexane, cyclohexane, heptane and mixtures of two or more thereof. More preferably, the solvent comprises methylisobutylketone, preferably is methylisobutylketone.

It is to be understood that in step (i) a further solvent may be added in order to precipitate, preferably crystallize, the chiral acid salt (S). In this case, the mixture obtained in (i) preferably additionally comprises the further solvent.

This further solvent may be added prior to, together with or after the addition of the chiral acid to the compound of formula (II). According to a preferred embodiment, the compound of formula (II) is dissolved in the suitable solvent mentioned above and a mixture, preferably a solution of the chiral acid, in a further solvent is added to the solution, wherein the further solvent and the suitable solvent may be the same or may be different.

In particular, the further solvent is selected from the group consisting of EtOH, i-PrOH, nPrOH, acetone, toluene, MTBE, $CH_2Cl_2$, ethyl acetate, acetone, isopropanol, methanol, water, formic acid ethyl ester, isopropyl acetate, propyl acetate, butyl acetate, acetonitrile, tetrahydrofuran, dichloromethane, methylisobutylketone, toluene, hexane, cyclohexane, heptane and mixtures of two or more thereof. More preferably, the suitable solvent and the further solvent are the same, in particular, they both comprise methylisobutylketone, preferably both are methylisobutylketone.

Thus, the present invention also relates to a process for the preparation of a chiral acid salt (S) of a compound of formula (II), as described above, and a chiral acid salt (S) of compound of formula (II), obtained or obtainable by said process, wherein step (i) comprises dissolving the compound of formula (II) in the suitable solvent and adding a solution of the chiral acid dissolved in a further solvent to the solution, wherein the further solvent and the suitable solvent are preferably the same, more preferably methylisobutylketone.

Preferably, the compound of formula (II) is dissolved in the suitable solvent and the mixture is heated to a temperature in the range of from 30 to 80° C., more preferably to a temperature in the range of from 30 to 60° C., more preferably to a temperature in the range of from 30 to 50° C., more preferably to a temperature in the range of from 30 to 40° C., prior to the addition of the tartaric acid. During the heating step, the temperature may be varied, constantly or stepwise, or held essentially constant. Preferably, the mixture is heated until a clear solution of the compound of formula (II) in the suitable solvent is obtained. Optionally, the mixture is afterwards cooled to room temperature.

The precipitation, preferably the crystallizing, in step (i) is preferably carried out at a temperature in the range of from 0 to 60° C., wherein the temperature is preferably continuously or stepwise decreased during step (i). The chiral acid may thus e.g. be added to a solution of the compound of formula (II) in the suitable solvent which has been previously heated or which has been previously heated and afterwards cooled to a specific temperature or which has not been previously heated.

After the addition of the chiral acid, and optionally the further solvent, the mixture may again be heated or alternatively be cooled or the temperature may be held constant. Preferably, the mixture is cooled to a temperature in the range of from 0 to 50° C., more preferably to a temperature in the range of from 0 to 40° C., more preferably to a temperature in the range of from 10 to 30° C.

Preferably, the mixture obtained in step (i) consists of the chiral acid salt (S), optionally the unreacted chiral acid, optionally the unreacted compound of formula (II), precipitated chiral acid salts (salt (S*) minus the amount of precipitated chiral acid salt (S)), the suitable solvent and optionally the further suitable solvent.

Step (ii)

In the optional step (ii) of the process of the invention, the chiral acid salt (S) is separated from the mixture obtained in step (i).

The separation may be carried out by any suitable method known to those skilled in the art. Preferably, the separating in step (ii) is carried out by centrifugation or filtration, preferably filtration.

It is to be understood that the separated salt may be subjected to a further treatment such as an after-treatment such as a purification step and/or lyophilization.

Preferably, the obtained chiral acid salt (S) of the compound formula (II) contains at least 90% by weight, more preferably at least 95% by weight, more preferably at least 96% by weight, more preferably at least 97% by weight, more preferably at least 98% by weight, more preferably at least 99% by weight, of the tartaric salt of the compound of formula (II*), based on the total weight of chiral acid salt of the compound of formula (II), i.e. based on the sum of (II**) and (II*). More preferably, the chiral acid salt (S) of the compound of formula (II) is the isolated chiral acid salt of the compound of formula (II*).

The term "isolated chiral acid salt of the compound of formula (II*)" in this context is denoted to mean that the salt of the compound of formula (II*) comprises less than 1% by weight of the salt of compound (II), preferably less than 0.5% by weight, more preferably less than 0.1% by weight, more preferably less than 0.05% by weight, more preferably less than 0.01% by weight, more preferably essentially no, more preferably no compound of formula (II) based on the total weight of the salts of (II*) and (II**).

Chiral Resolution of the Compound of Formula (IIa*)

Alternatively, in case (II) differs from (IIa), also a chiral resolution of compound (IIa) may be carried out. As mentioned above, compound (II) may comprise a mixture of compounds (IIa*) and (IIa**)

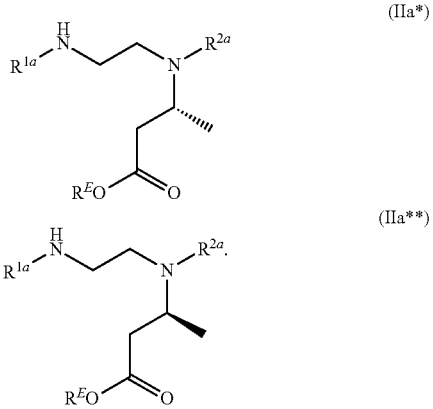

The chiral resolution of compound (IIa) is carried out as discloses above in connection with the chiral resolution of compound of formula (II).

Enantioselective Reduction

According to a further preferred embodiment, in step (a3), the compound is stereoselectively reduced to give a compound of formula (IIa*)

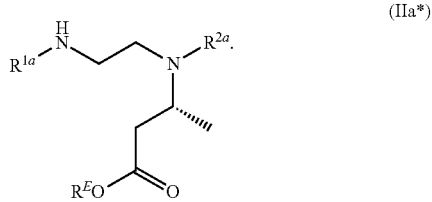

In this case, preferably a chiral catalyst, i.e. a metal catalyst comprising a chiral ligand is employed. As mentioned above, preferably a metal catalyst and hydrogen is used. The metal catalyst is preferably selected from the group consisting of a catalyst comprising Pd, Fe, Ir, Rh and mixtures of two or more thereof. In case of a stereoselective reduction, the metal catalyst is preferably selected from the group consisting of a catalyst comprising Pd, Fe, Ir, Rh, and mixtures of two or more thereof. Preferably, the catalyst comprises Fe and/or Rh.

The reaction is preferably carried out at a hydrogen pressure in the range of from 1 to 25 bar, more preferably, 2.5 to 10 bar. During the reaction, the pressure may be varied or held essentially constant.

Preferably, the reaction is carried out at a temperature in the range of from 10 to 100° C., more preferably in the range of from 20 to 60° C., more preferably at 25 to 40 C. During the reaction, the temperature may be varied or held essentially constant.

The reaction may be carried out in any suitable solvent known to those skilled in the art. Preferably, the cyclization reaction is carried out in an organic solvent, more preferably in a solvent selected from the group consisting of methanol, ethanol, trifluoroethanol (TFE), dichloromethane, DMF, DMSO, NMP, methanol, ethanol, propanol, isopropanol, butanol, s-butanol, t-butanol, tetrahydrofuran, 2-methyltetrahydrofuran, methyltertbutylether, diethylether, diisopropylether, toluene, acetonitrile and mixtures of two or more thereof. Preferably, the solvent is methanol or TFE.

Preferably in compound (IIa), $R^1$ is Boc and $R^2$ is H.

Step (a1)

In step (a1), a compound of formula (III) is reacted with a compound of formula (IV) to give the compound of formula (V).

Preferably, step (a1) is carried out at a temperature in the range of from 0 to 80° C., more preferably in the range of from 10 to 50° C., more preferably in the range of from 20 to 35° C. During the reaction, the temperature may be varied or held essentially constant.

Preferably, an organic solvent is used in step (a1), more preferably in a solvent selected from the group consisting of methanol, ethanol, trifluoroethanol (TFE), dichloromethane, DMF, DMSO, NMP, methanol, ethanol, propanol, isopropanol, butanol, s-butanol, t-butanol, tetrahydrofuran, 2-methyltetrahydrofuran, methyltertbutylether, diethylether, diisopropylether, toluene, acetonitrile and mixtures of two or more thereof. Most preferably, the reaction is carried out in dichloromethane.

Preferably, (a1) is carried out in the presence of a catalysing agent, such as a dehydrating reagent or an acidic catalyst. The term "dehydrating agent" is denoted to mean an agent which removes water from the reagents such as by absorption. Such dehydrating agents are known to those skilled in the art. Preferably, the catalysing agent is $SiO_2$ or a molecular sieve or a mixture thereof. More preferably, the catalysing agent $SiO_2$.

mixture is filtered to remove the $SiO_2$ and the solvent is removed, such as under reduced pressure.

More preferably, compound (V) is further purified, e.g. by distillation.

Step (a4)

As mentioned above, $R^{1a}$ may be different from $R^1$ and/or $R^{2a}$ may be different from $R^2$. In particular, the following embodiments are mentioned by way of example:

| Entry | (IIa) $R^{1a}$ | $R^{2a}$ | (II) $R^1$ | $R^2$ |
|---|---|---|---|---|
| 1 | $PG^1$ | $PG^2$ | H | $PG^2$ |
| 2 | $PG^1$ | H | H | $PG^2$ |
| 3 | $PG^1$ | H | H | [2-(2H-1,2,3-triazol-2-yl)-4-methylbenzoyl] |
| 4 | [5-chlorobenzoxazol-2-yl] | H | [5-chlorobenzoxazol-2-yl] | $PG^2$ |
| 5 | [5-chlorobenzoxazol-2-yl] | H | [5-chlorobenzoxazol-2-yl] | [2-(2H-1,2,3-triazol-2-yl)-4-methylbenzoyl] |
| 6 | H | [2-(2H-1,2,3-triazol-2-yl)-4-methylbenzoyl] | [5-chlorobenzoxazol-2-yl] | [2-(2H-1,2,3-triazol-2-yl)-4-methylbenzoyl] |

In the above mentioned table $PG^1$ is preferably Boc and $PG^2$ is preferably Cbz.

In case $R^1$ differs from $R^{1a}$ or in case $R^2$ differs from $R^{2a}$ or in case both $R^{1a}$ and $R^{2a}$ differ from $R^{1a}$ and $R^{2a}$, respectively, step (a4) is carried out. Depending on the respective groups to be replaced, step (a4) comprises one or multiple step, such a deprotection step and/or a protection step and/or a coupling step with a compound of formula Step (a2)

Preferably, the reaction mixture obtained in step (a1) is subjected to a suitable work-up in step (a2), such as an isolation of the respective compound of formula (V). Such working up may comprise one or more stages wherein preferably at least one stage comprises a purification step, such as an extraction and/or a precipitation and/or filtration and/or chromatography or the like. Preferably, the reaction

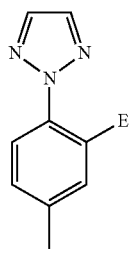

(XI)

and/or a coupling step with a compound of formula

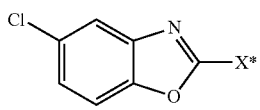

(XII)

to give the compound of formula (II).

According to a preferred embodiment, step (a) according to the invention e.g. comprises (a1) reacting a compound of formula (III)

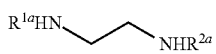

(III)

with a compound of formula (IV)

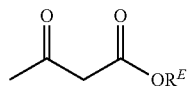

(IV)

to give a compound of formula (V)

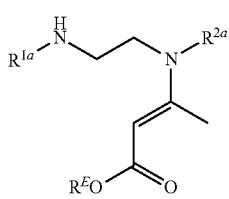

(V)

wherein $R^{1a}$ is $PG^1$ and wherein $R^{2a}$ is H, and $PG^{1a}$ is a suitable protecting group, preferably a Boc group, (a2) optionally purifying the compound of formula (V), (a3) reducing the compound of formula (V) to give a compound of formula (IIa), wherein $R^{1a}$ is $PG^1$ and wherein $R^{2a}$ is H (a4) replacing $R^{2a}$ with

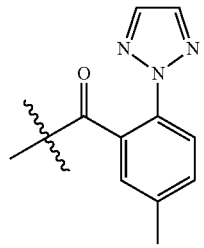 [SMILES: *C(=O)c1cc(C)ccc1-n1nccn1]

by reacting a compound of formula (IIa) with a compound of formula (XI)

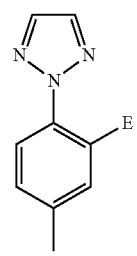

(XI)

wherein E is —COOH or a reactive carboxy group, and replacing $R^{1a}$ with H by removing the protecting group $PG^1$.

Further, the present invention also relates to the preparation of a compound of formula (IIa) and to a compound (IIa) obtained or obtainable by said method, the method comprising (a1) reacting a compound of formula (III)

(III)

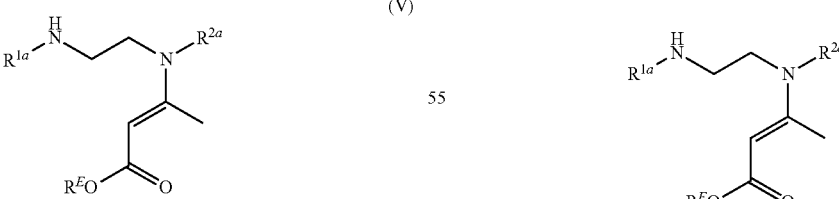

with a compound of formula (IV)

(IV)

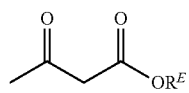

to give a compound of formula (V)

(V)

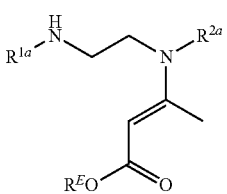

wherein $R^{1a}$ is $PG^1$ and wherein $R^{2a}$ is H, and $PG^{1a}$ is a suitable protecting group, preferably a Boc group, (a2) optionally purifying the compound of formula (V), (a3) reducing the compound of formula (V) to give a compound of formula (IIa), wherein $R^{1a}$ is $PG^1$ and wherein $R^{2a}$ is H.

Methods for attaching and removing of a protecting group are known to those skilled in the art and depend on the respective protecting group employed.

Representative protecting groups for amino groups are well known to those skilled in the art and methods for attaching them to amino groups as well as removing them are described, for example, in T. W. Greene and G. M. Wuts, *Protecting Groups in Organic Synthesis*, Third Edition, Wiley, N.Y., 1999, and references cited therein.

In case, the protecting group is a Boc group, the removal is preferably carried out under acidic conditions. More preferably, the removal is carried out with HCl or TFA. The removal of such protecting groups may be carried out in any suitable solvent known to those skilled in the art. Preferably, the reaction is carried out in an organic solvent, more preferably in a solvent selected from the group consisting of methanol, ethanol, trifluoroethanol (TFE), dichloromethane, DMF, DMSO, NMP, methanol, ethanol, propanol, isopropanol, butanol, s-butanol, t-butanol, tetrahydrofuran, 2-methyltetrahydrofuran, methyltertbutylether, diethylether, diisopropylether, toluene, acetonitrile and mixtures of two or more thereof. Preferably, the removal is carried out at a temperature in the range of from 0 to 40° C., more preferably in the range of from 10 to 30° C., more preferably at room temperature. During the reaction, the temperature may be varied or held essentially constant.

In case, the protecting group is a Cbz group, the removal is preferably carried out under reductive conditions. More preferably, the removal is carried out with hydrogen and a metal catalyst, preferably a palladium catalyst, more preferably the protecting group is removed with Pd/C. The removal of such a protecting group may be carried out in any suitable solvent known to those skilled in the art. Preferably, the reaction is carried out in an organic solvent, more preferably in a solvent selected from the group consisting of methanol, ethanol, trifluoroethanol (TFE), dichloromethane, DMF, DMSO, NMP, methanol, ethanol, propanol, isopropanol, butanol, s-butanol, t-butanol, tetrahydrofuran, 2-methyltetrahydrofuran, methyltertbutylether, diethylether, diisopropylether, toluene, acetonitrile and mixtures of two or more thereof and mixtures of two or more thereof. Preferably, the removal is carried out at a temperature in the range of from 0 to 60° C., more preferably in the range of from 10 to 50° C., more preferably at room temperature. During the reaction, the temperature may be varied or held essentially constant. In case hydrogen is used, the reaction is preferably carried out at a pressure in the range of from 1 to 3 bar, more preferably, 1.5 to 2.5 bar.

In case in step (a4) the respective compound is reacted, i.e. coupled, with a compound of formula (XI), wherein E is —COOH or a reactive carboxy group, the coupling is preferably carried out in the presence of a suitable base, preferably an organic base, most preferably an amino group comprising base, most preferably a base selected from the group consisting of diisopropylamine (DIEA), triethylamine (TEA), N-methylmorpholine, N-methyl-imidazole, 1,4-diazabicyclo[2.2.2]octane (DABCO), N-methylpiperidine, N-methylpyrrolidine, 2,6-lutidine, collidine, pyridine, 4-dimethylaminopyridine, 1,8-diazabicyclo[5.4.0]undec-7-ene (DBU). As regards the reaction conditions used in this coupling step, preferably, the reaction is carried out in an organic solvent, such as N-methyl pyrrolidone (NMP), dimethyl sulfoxide (DMSO), acetonitrile, acetone, dimethyl acetamide (DMA), dimethyl formamide (DMF), formamide, tetrahydrofuran (THF), 1,4-dioxane, diethyl ether, tert.-butyl methyl ether (MTBE), dichloromethane (DCM), chloroform, tetrachloromethane and mixtures of two or more thereof. More preferably, the reaction is carried out in dichloromethane.

The temperature of the coupling reaction is preferably in the range of from 0 to 100 C, more preferably in the range of from 5 to 50° C., and especially preferably in the range of from 15 to 30° C. During the course of the reaction, the temperature may be varied, preferably in the above given ranges, or held essentially constant.

With respect to preferred groups E, reference is made to the respective details given above with respect to step (d1) which equally apply.

Compound A

The present invention is further directed to a compound of formula (A) of structure

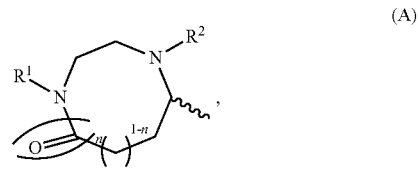

(A)

wherein n is 1 or 0.

Thus the compound (A) has, e.g., the structure (Ia) or (Ib)

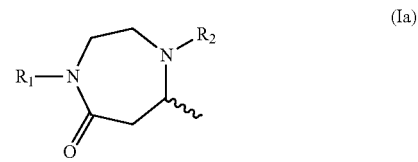

(Ia)

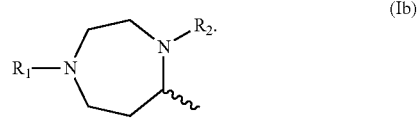

(Ib)

Residue R¹:

Regarding R¹, R¹ is selected from the group consisting of H, PG¹ and R^A with R^A being

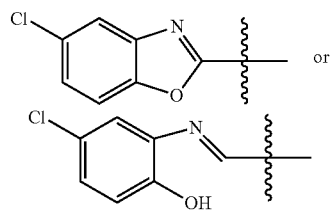

wherein PG¹ is a suitable protecting group.

Thus, the compound of formula (A) has, e.g., a structure selected from the group consisting of

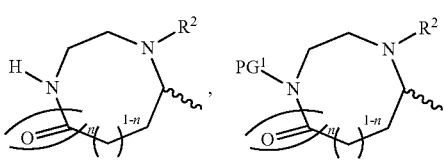

-continued

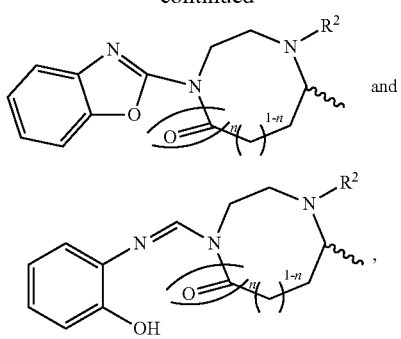

i.e. a structure selected from the group consisting of

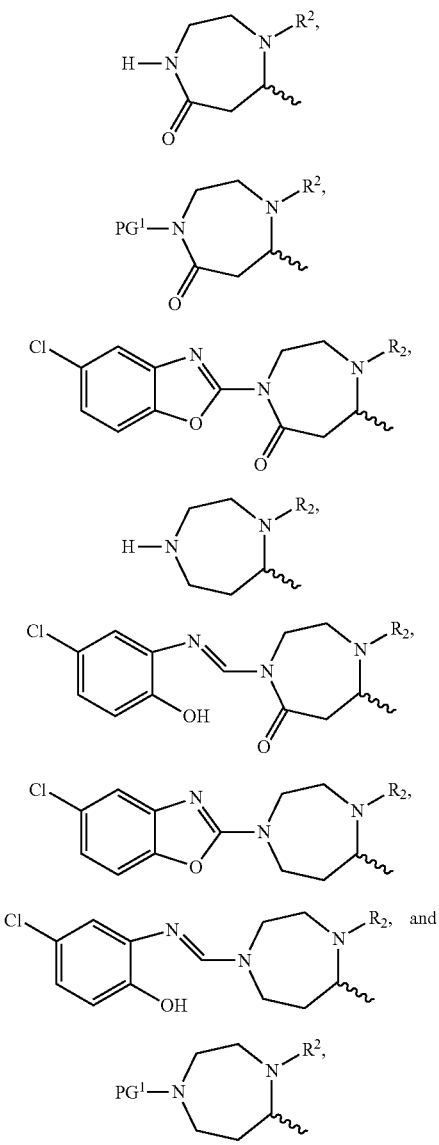

wherein at each occurrence R² is as defined above and wherein preferably in formula (Ia-1), (Ia-4), (Ia-6) R² is not H and wherein preferably in (Ia-6) R² is not

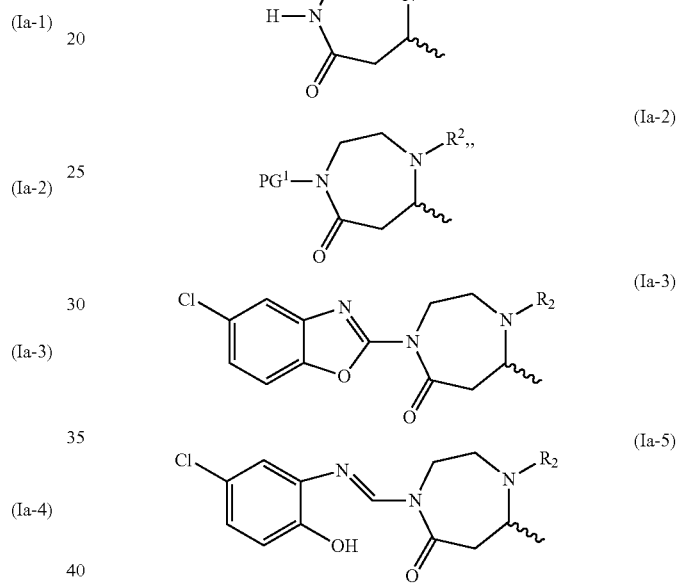

Preferably, the structures are selected from the group consisting of (Ia-1)

(Ia-2)

(Ia-3)

(Ia-5)

wherein in formula (Ia-1) R² is not H.

The term "suitable protecting group" as used herein is denoted to encompass any amino protecting group. The term "protecting group" as such refers to a chemical moiety that can be selectively attached to and removed from a particular chemically reactive functional group in a molecule to prevent it from participating in undesired chemical reactions. The protecting group will vary depending on reaction conditions to be employed and the presence of additional reactive or protecting groups in the molecule. It is understood that the term "amino protecting group" is a chemical moiety being attached to a former amino group. After removal of the protecting group, the free amine is regained. Representative protecting groups for amino groups are well known to those skilled in the art and are described, for example, in T. W. Greene and G. M. Wuts, *Protecting Groups in Organic Synthesis*, Third Edition, Wiley, N.Y., 1999, and references cited therein.

An "amino-protecting group" preferably includes both acyclic as well as cyclic protecting groups. A "cyclic protecting group" is a group which, together with the N to which it is bound, forms a cyclic group. Preferred protecting groups for PG¹ include, but are not limited to, carbamates, such as Boc (t-butyloxycarbonyl, Cbz (carboxybenzyl), Fmoc (fluorenylmethyloxycarbonyl), Alloc (allyloxycarbonyl), methyl and ethyl carbamates; trityl, benzyl, benzylidene, tosyl, PNZ, trifluoroacetate, phtalimide and the like; cyclic imide derivatives, such as succinimide and phthalimide; amides, such as formyl, (un)substituted acetyl, and benzoyl; and trialkyl silyl groups, such as t-butyldimethylsilyl and triisopropylsilyl. Particularly preferred amino-protecting groups include Boc, Cbz, Fmoc, benzyl, acetyl, benzoyl, trityl, Cbz, PNZ, Alloc, Trifluoroacetate, Phthalimide and the like. Most preferably, PG$^1$ is wherein PG$^2$ is selected from the group consisting of Benzyl, t-butyloxycarbonyl (Boc), Cbz, PNZ, Alloc, Trifluoroacetate and Phthalimide, more preferably PG$^1$ is a Boc group or a Cbz group, more preferably Boc.

Thus, compound A is preferably selected from the group consisting of

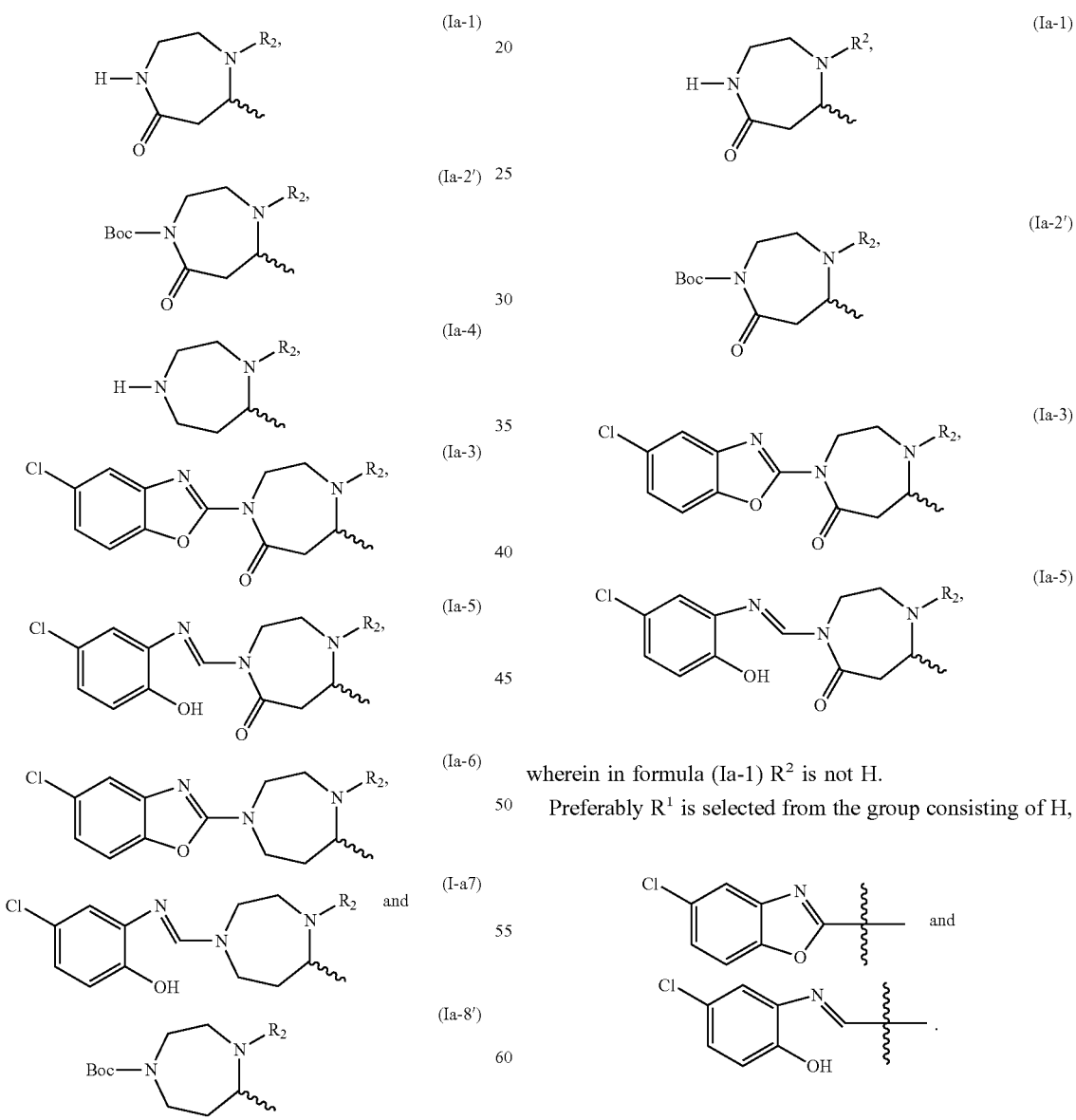

wherein at each occurrence R$^2$ is as defined above and wherein preferably in formula (Ia-1), (Ia-4), (Ia-6) R$^2$ is not H and wherein preferably in (Ia-6) R$^2$ is not

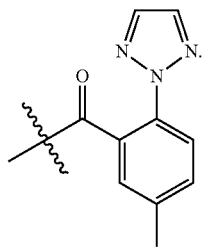 [SMILES: *C(=O)c1cc(C)ccc1-n1nccn1]

More preferably, compound A is selected from the group consisting of wherein in formula (Ia-1) R$^2$ is not H.

Preferably R$^1$ is selected from the group consisting of H,

Most preferably R$^1$ is H.

Residue R$^2$:

Regarding R$^2$, R$^2$ is selected from the group consisting of H, PG$^2$ and R$^B$ with R$^B$ being

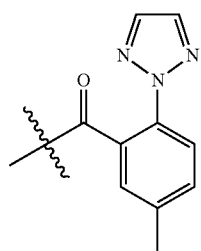

and wherein PG² is a suitable protecting group, and wherein n is 0 or 1.

Thus, the compound of formula (A) has, e.g., a structure selected from the group consisting of

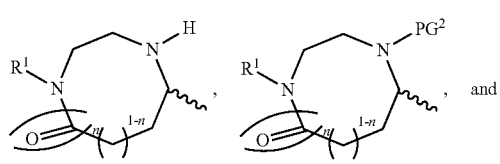

i.e. a structure selected from the group consisting of (Ia-a)

(Ia-b)

(Ia-c)

(Ia-d)

(Ia-e)
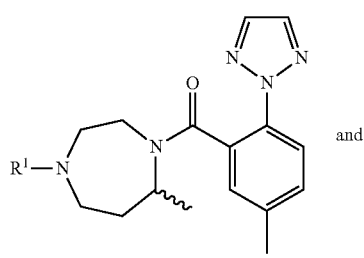 and (Ia-f)
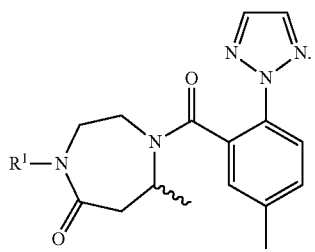

wherein in (Ia-a), in (Ia-b), in (Ia-e) R¹ is not H, wherein in (Ia-e) R¹ is not

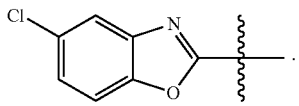 [SMILES: *c1nc2cc(Cl)ccc2o1]

PG² is a suitable protecting group as defined above in connection with PG¹. Preferred protecting groups for PG² include, but are not limited to, carbamates, such as Boc (t-butyloxycarbonyl, Cbz (carboxybenzyl), Fmoc (fluorenylmethyloxycarbonyl), Alloc (allyloxycarbonyl), methyl and ethyl carbamates; trityl, benzyl, benzylidene, tosyl, PNZ, trifluoroacetate, phtalimideand the like; cyclic imide derivatives, such as succinimide and phthalimide; amides, such as formyl, (un)substituted acetyl, and benzoyl; and trialkyl silyl groups, such as t-butyldimethylsilyl and triisopropylsilyl. Particularly preferred amino-protecting groups include Boc, Cbz, Fmoc, benzyl, acetyl, benzoyl, trityl, Cbz, PNZ, Alloc, Trifluoroacetate, Phthalimide and the like. Most preferably, PG¹ is wherein PG² is selected from the group consisting of Benzyl, t-butyloxycarbonyl (Boc), Cbz, PNZ, Alloc, Trifluoroacetate and Phthalimide, more preferably PG² is a Boc group or a Cbz group, more preferably Cbz.

Thus, compound A is preferably selected from the group consisting of (Ia-a)
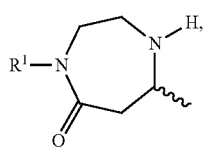

(Ia-b)
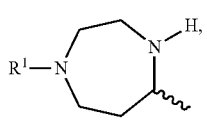

-continued

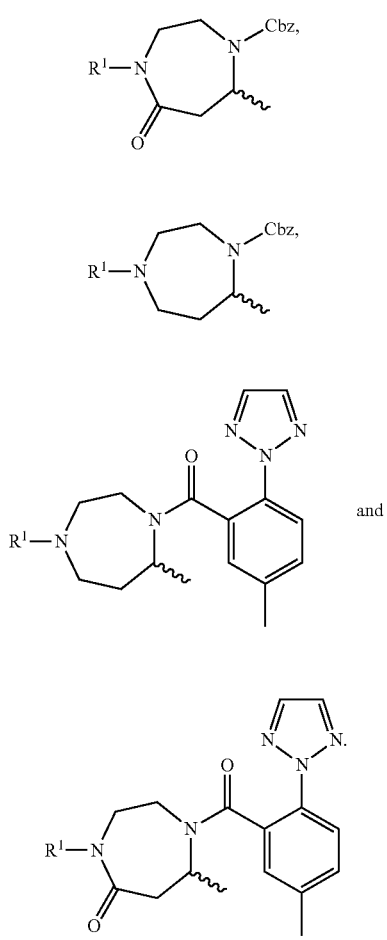

wherein in (Ia-a), in (Ia-b), in (Ia-e) $R^1$ is not H, wherein in (Ia-e) $R^1$ is not

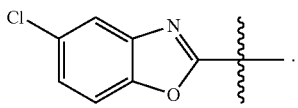 [SMILES: *c1nc2cc(Cl)ccc2o1]

More preferably, compound A is selected from the group consisting of

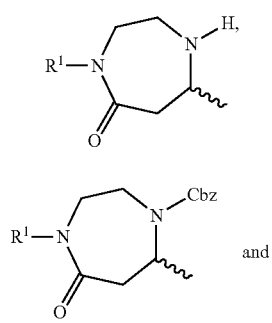

-continued

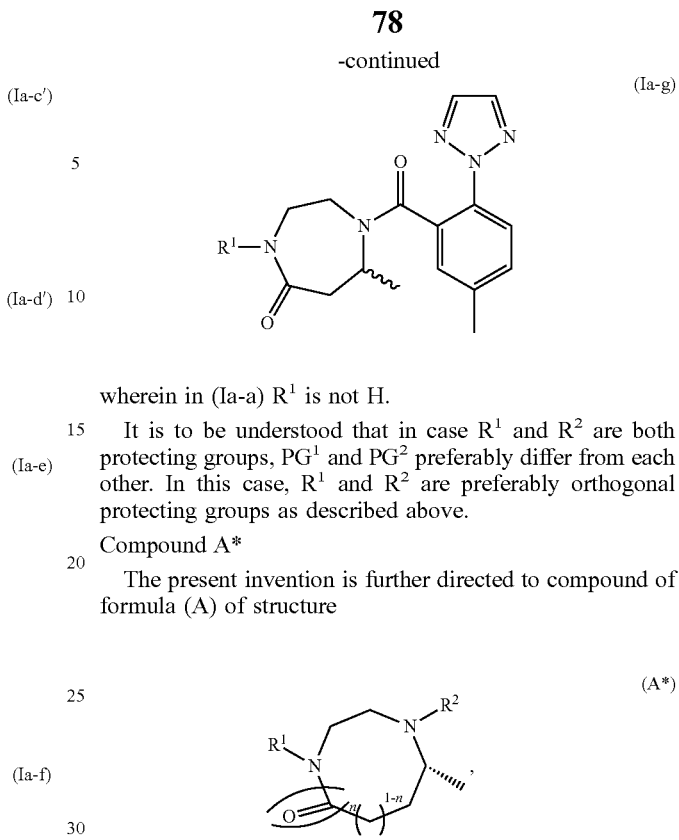

wherein in (Ia-a) $R^1$ is not H.

It is to be understood that in case $R^1$ and $R^2$ are both protecting groups, $PG^1$ and $PG^2$ preferably differ from each other. In this case, $R^1$ and $R^2$ are preferably orthogonal protecting groups as described above.

Compound A*

The present invention is further directed to compound of formula (A) of structure (A*)

wherein n is 1 or 0.

Thus the compound (A) has, e.g., the structure (Ia) or (Ib)

(Ia*)

(Ib*)

Residue $R^1$:

Regarding $R^1$, $R^1$ is selected from the group consisting of H, $PG^1$ and $R^4$ with $R^4$ being

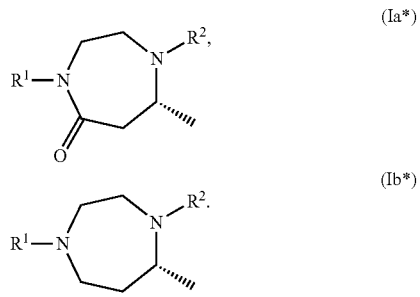

wherein $PG^1$ is a suitable protecting group.

Thus, the compound of formula (A) has, e.g., a structure selected from the group consisting of

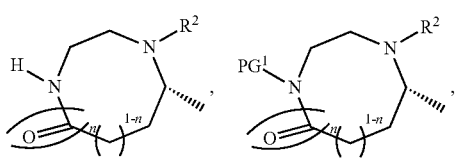

i.e. a structure selected from the group consisting of

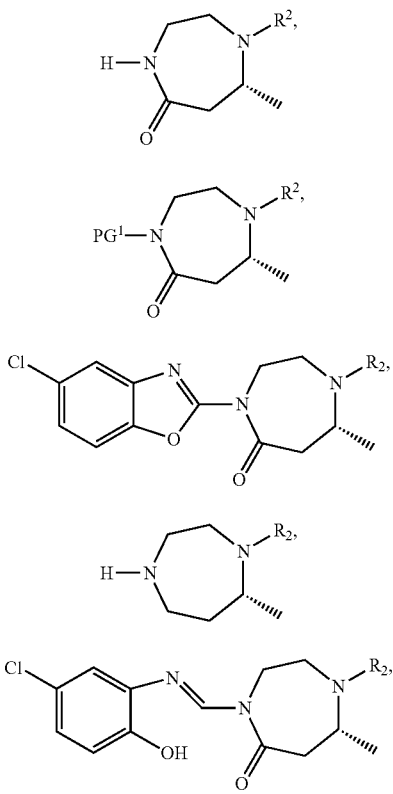

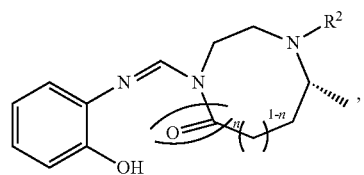

wherein at each occurrence $R^2$ is as defined above and wherein preferably in formula (Ia*-1), (Ia*-4), (Ia*-6) $R^2$ is not H and wherein preferably in (Ia*-6) $R^2$ is not

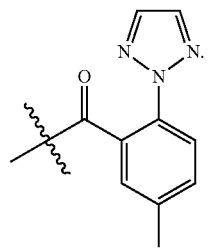 [SMILES: *C(=O)c1cc(C)ccc1-n1nccn1]

Preferably, the structures are selected from the group consisting of

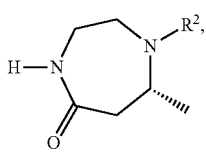
(Ia*-1)

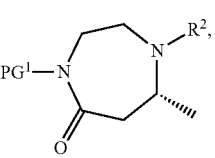
(Ia*-2)

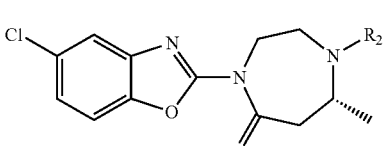
(Ia*-3)

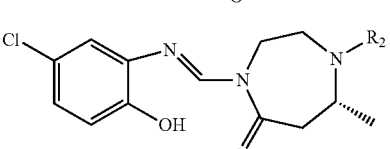
(Ia*-5)

wherein in formula (Ia*-1) $R^2$ is not H.

Compound (A) is preferably selected from the group consisting of

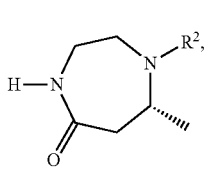
(Ia*-1)

-continued

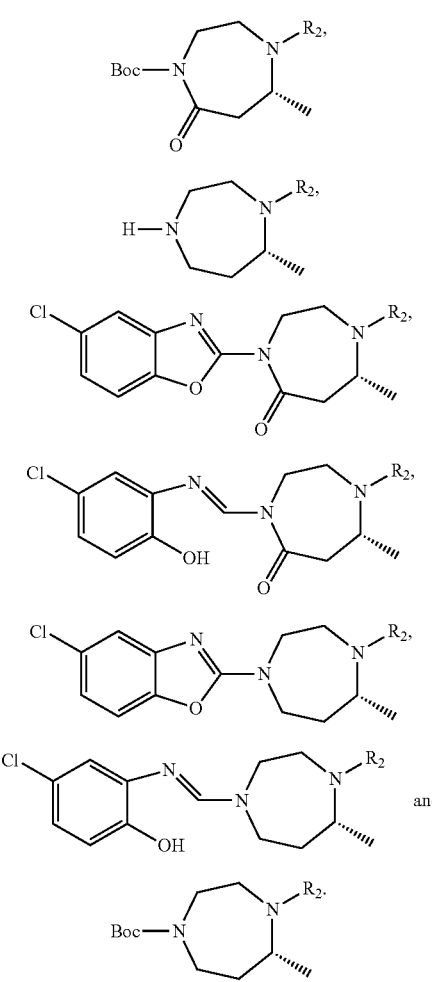

wherein at each occurrence R² is as defined above and wherein preferably in formula (Ia*-1), (Ia*-4), (Ia*-6) R² is not H and wherein preferably in (Ia*-6) R² is not

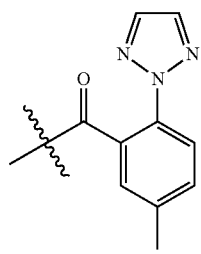 [SMILES: *C(=O)c1cc(C)ccc1-n1nccn1]

More preferably compound A is selected from the group consisting of

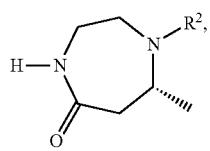
(Ia*-1)

-continued

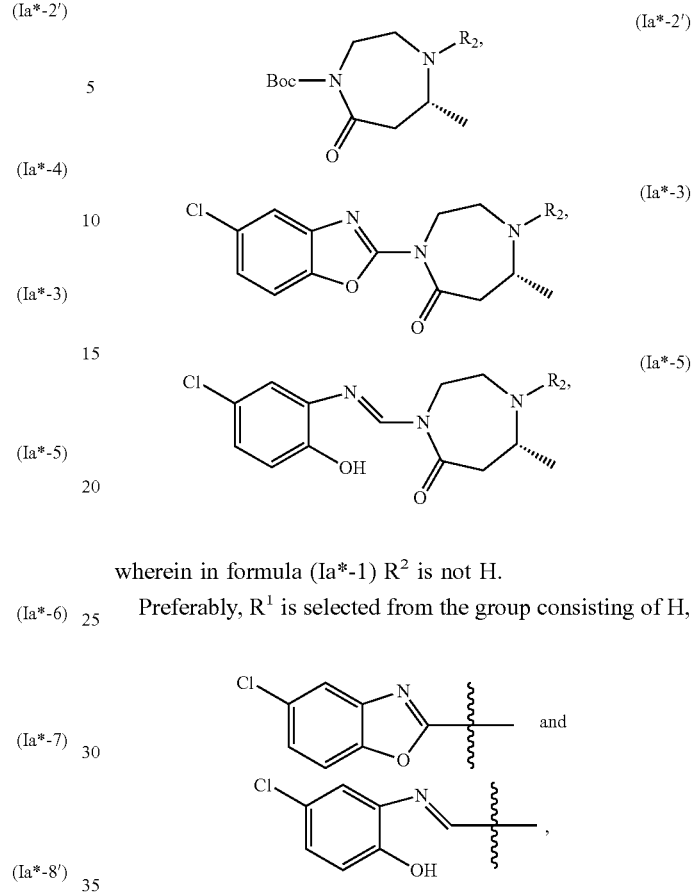

wherein in formula (Ia*-1) R² is not H.

Preferably, R¹ is selected from the group consisting of H,

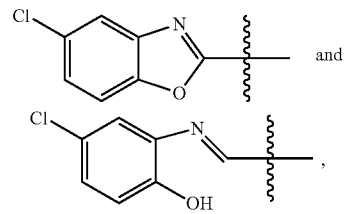

most preferably R¹ is H.

Residue R²:

Regarding R², R² is selected from the group consisting of H, PG² and $R^B$ with $R^B$ being

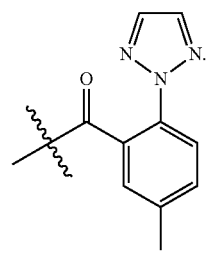 [SMILES: *C(=O)c1cc(C)ccc1-n1nccn1]

and wherein PG² is a suitable protecting group, and wherein n is 0 or 1.

Thus, the compound of formula (A) has, e.g., a structure selected from the group consisting of

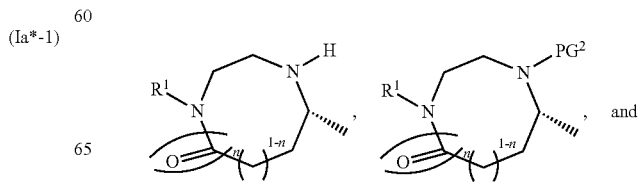

-continued

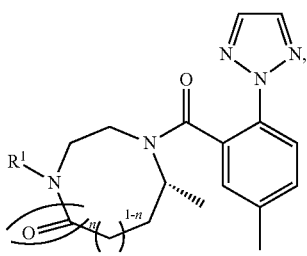

i.e. a structure selected from the group consisting of

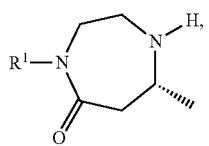
(Ia*-a)

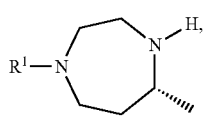
(Ia*-b)

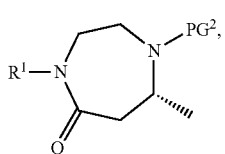
(Ia*-c)

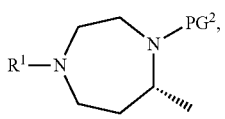
(Ia*-d)

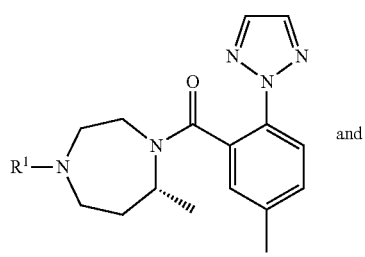
(Ia*-e)

and

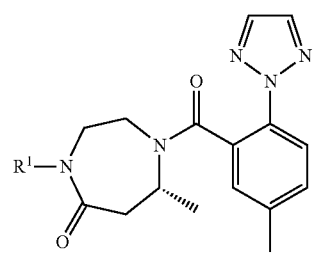
(Ia*-f)

wherein in (Ia*-a), in (Ia*-b), in (Ia*-e) R¹ is not H, wherein in (Ia*-e) R¹ is not

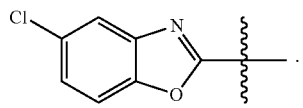 [SMILES: *c1nc2cc(Cl)ccc2o1]

PG² is a suitable protecting group as defined above in connection with PG¹. Preferred protecting groups for PG² include, but are not limited to, carbamates, such as Boc (t-butyloxycarbonyl, Cbz (carboxybenzyl), Fmoc (fluorenylmethyloxycarbonyl), Alloc (allyloxycarbonyl), methyl and ethyl carbamates; trityl, benzyl, benzylidene, tosyl, PNZ, trifluoroacetate, phtalimideand the like; cyclic imide derivatives, such as succinimide and phthalimide; amides, such as formyl, (un)substituted acetyl, and benzoyl; and trialkyl silyl groups, such as t-butyldimethylsilyl and triisopropylsilyl. Particularly preferred amino-protecting groups include Boc, Cbz, Fmoc, benzyl, acetyl, benzoyl, trityl, Cbz, PNZ, Alloc, Trifluoroacetate, Phthalimide and the like. Most preferably, PG¹ is wherein PG² is selected from the group consisting of Benzyl, t-butyloxycarbonyl (Boc), Cbz, PNZ, Alloc, Trifluoroacetate and Phthalimide, more preferably PG² is a Boc group or a Cbz group, more preferably Cbz.

Thus, compound A is preferably selected from the group consisting of

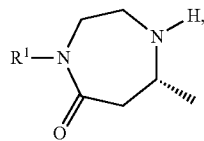
(Ia*-a)

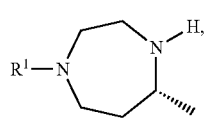
(Ia*-b)

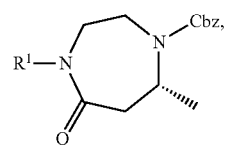
(Ia*-c')

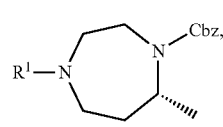
(Ia*-d')

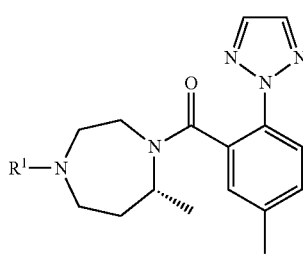
(Ia*-e)

and

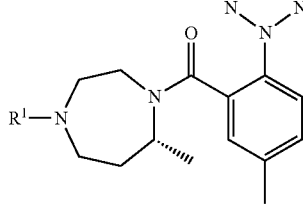

-continued (Ia*-f)
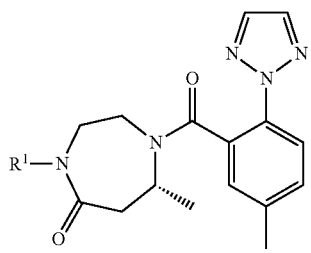

wherein in (Ia*-a), in (Ia*-b), in (Ia*-e) R¹ is not H, wherein in (Ia*-e) R¹ is not

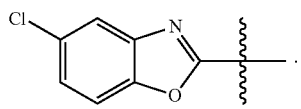 [SMILES: *c1nc2cc(Cl)ccc2o1]

More preferably, compound A is selected from the group consisting of (Ia*-a)
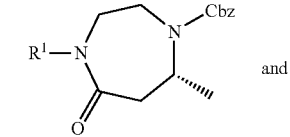

(Ia*-c')
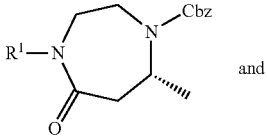 and (Ia*-f)
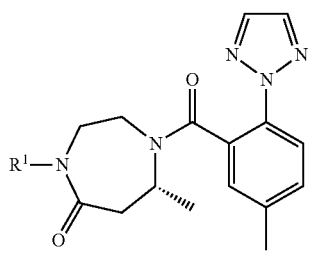

wherein in (Ia*-a) R¹ is not H.

It is to be understood that in case R¹ and R² are both protecting groups, PG¹ and PG² preferably differ from each other. In this case, R¹ and R² are preferably orthogonal protecting groups as described above.

Preferably, compound (A) and compound (A*) e.g. have as structure selected from the structure shown in the table below:

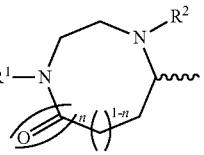 , preferably 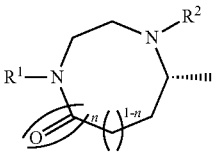

| Structure Number | n | R¹ | R² |
|---|---|---|---|
| 2 | 1 | H | Cbz |
| 3 | 1 | H | 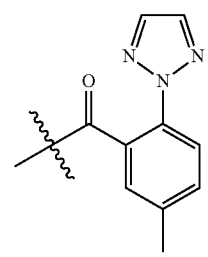 [SMILES: *C(=O)c1cc(C)ccc1-n1nccn1] |
| 4 | 1 | Boc | H |
| 5 | 1 | Boc | Cbz |
| 6 | 1 | Boc | 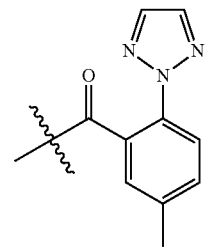 [SMILES: *C(=O)c1cc(C)ccc1-n1nccn1] |
| 7 | 1 | 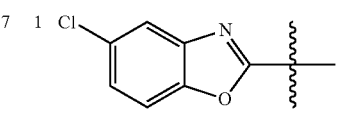 | H |
| 8 | 1 | 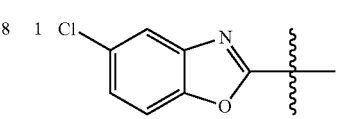 | Cbz |
| 9 | 1 | 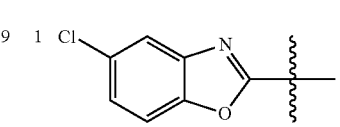 | 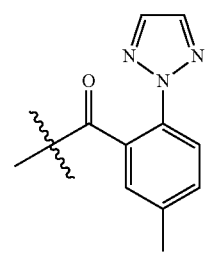 [SMILES: *C(=O)c1cc(C)ccc1-n1nccn1] |
| 10 | 1 | 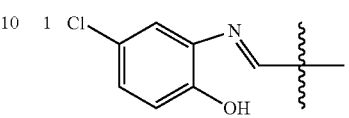 | H |
| 11 | 1 | 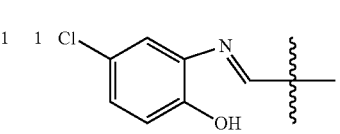 | Cbz |

-continued

| Structure Number | n | R¹ | R² |
|---|---|---|---|
| 12 | 1 | 5-chloro-2-hydroxyphenyl-CH=N- | triazolyl-benzoyl-methyl(Cbz-like) |
| 14 | 0 | H | Cbz |
| 16 | 0 | Boc | H |
| 17 | 0 | Boc | Cbz |
| 19 | 0 | Boc | triazolyl-methylbenzoyl |
| 20 | 0 | 5-chloro-benzoxazol-2-yl | Cbz |
| 22 | 0 | 5-chloro-2-hydroxyphenyl-CH=N- | H |
| 23 | 0 | 5-chloro-2-hydroxyphenyl-CH=N- | Cbz |
| 24 | 0 | 5-chloro-2-hydroxyphenyl-CH=N- | triazolyl-methylbenzoyl |

Further, the present invention is directed to a crystalline form (A) of compound of formula

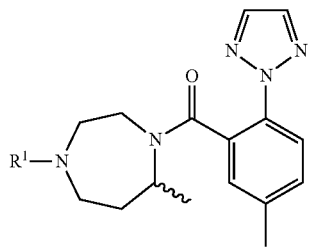

(VIIb)

wherein $R^1$ is H, i.e. to a crystalline compound of formula

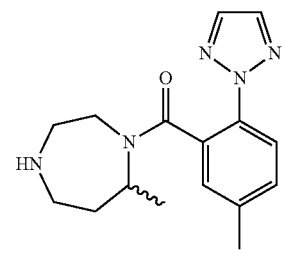

(VIIb-H)

Crystalline form (A) has an X-ray powder diffraction pattern comprising a peak at 2-theta angle of approximately 12.4°±0.2°, more preferably has an X-ray powder diffraction pattern comprising peaks at 2-theta angles of approximately 4.8±0.2°, 12.4°±0.2°, 14.2°±0.2°, 19.9°±0.2° and 20.8°±0.2° and/or at approximately 7.7±0.2°, 11.4°±0.2°, 12.4°±0.2°, 16.2°±0.2° and 18.1°±0.2°, more preferably, at approximately 4.8±0.2°, 12.4°±0.2°, 14.2°±0.2°, 19.9°±0.2° and 20.8°±0.2°, wherein the X-ray powder diffraction pattern is measured at a temperature in the range of from 15 to 25° C. with Cu-K$\alpha_{1,2}$ radiation having a wavelength of 0.15419 nm.

Alternatively crystalline form (A) has an X-ray powder diffraction pattern comprising a peak at 2-theta angle of approximately 12.4°±0.2°, more preferably has an X-ray powder diffraction pattern comprising peaks at 2-theta angles of approximately 4.8±0.2°, 12.4°±0.2°, 14.2°±0.2°, 19.9°±0.2° and 20.8°±0.2. The X-ray preferably further comprises peaks at one or more than one or all of 2-theta angles of 21.6°±0.2°, 22.6°±0.2° 22.9°±0.2 and 27.8°±0.2°. The X-ray powder diffraction pattern is measured at a temperature in the range of from 15 to 25° C. with Cu-K$\alpha_{1,2}$ radiation having a wavelength of 0.15419 nm.

An XRPD of crystalline form (A) of compound (VIIb-H) is depicted in FIG. 3.

A peak listing of the XRPD of crystalline form (A) of compound (VIIb-H) is presented in Table 1

TABLE 1

| No. | Pos. [°2Th. | Rel. Int. [%] |
|---|---|---|
| 1 | 2.3 | 4 |
| 2 | 4.8 | 44 |
| 3 | 9.6 | 3 |
| 4 | 12.4 | 88 |
| 5 | 14.2 | 43 |
| 6 | 14.4 | 19 |
| 7 | 17.1 | 5 |
| 8 | 17.9 | 6 |
| 9 | 18.1 | 6 |

TABLE 1-continued

| No. | Pos. [°2Th.] | Rel. Int. [%] |
|---|---|---|
| 10 | 19.2 | 7 |
| 11 | 19.6 | 16 |
| 12 | 19.9 | 27 |
| 13 | 20.8 | 100 |
| 14 | 21.6 | 24 |
| 15 | 22.6 | 25 |
| 16 | 22.9 | 19 |
| 17 | 24.2 | 1 |
| 18 | 25.0 | 7 |
| 19 | 25.9 | 6 |
| 20 | 26.5 | 8 |
| 21 | 26.7 | 9 |
| 22 | 27.5 | 5 |
| 23 | 27.8 | 20 |
| 24 | 28.4 | 6 |
| 25 | 28.7 | 7 |
| 26 | 29.3 | 2 |
| 27 | 30.1 | 6 |
| 28 | 31.5 | 2 |
| 29 | 32.1 | 2 |
| 30 | 33.1 | 2 |
| 31 | 33.9 | 2 |
| 32 | 35.0 | 5 |
| 33 | 35.5 | 2 |
| 34 | 36.4 | 1 |
| 35 | 37.3 | 2 |
| 36 | 38.4 | 4 |
| 37 | 39.3 | 2 |

The present invention is further directed to compound of formula (VIIb*), wherein $R^1$ is H

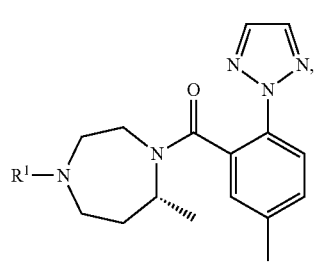

(VIIb*)

i.e. to a compound of formula (VIIb*-H)

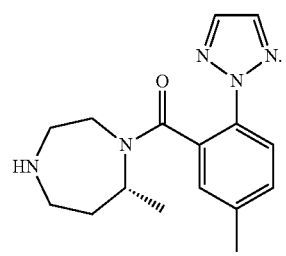

(VIIb*-H)

Preferably the compound of formula (VIIb*-H) is crystalline. More preferably, the crystalline compound of formula (VIIb*-H) is the crystalline form (I). Crystalline form (I) has an X-ray powder diffraction pattern comprising a peak at 2-theta angle of approximately 11.3°±0.2°, more preferably has an X-ray powder diffraction pattern comprising peaks at 2-theta angles of 11.3°±0.2°, 12.3°±0.2°, 13.3°±0.2°, 16.0°±0.2° 20.00±0.2°. The X-ray powder diffraction pattern of crystalline form (I) preferably further comprises peaks at 2-theta angles of 16.5±0.2°, 18.3°±0.2°, 20.1°±0.2°, 22.7°±0.2°, wherein the X-ray powder diffraction pattern is measured at a temperature in the range of from 15 to 25° C. with Cu-K$\alpha_{1,2}$ radiation having a wavelength of 0.15419 nm.

An XRPD of crystalline form (I) of compound (VIIb*-H) is depicted in FIG. 4.

A peak listing of the XRPD of form (I) is presented in Table 2.

TABLE 2

| No. | Pos. [°2Th.] | Rel. Int. [%] |
|---|---|---|
| 1 | 11.3 | 100 |
| 2 | 12.3 | 93 |
| 3 | 13.3 | 59 |
| 4 | 16.0 | 39 |
| 5 | 16.5 | 18 |
| 6 | 16.9 | 9 |
| 7 | 17.1 | 7 |
| 8 | 18.3 | 32 |
| 9 | 19.1 | 10 |
| 10 | 20.0 | 83 |
| 11 | 20.1 | 45 |
| 12 | 22.0 | 17 |
| 13 | 22.1 | 15 |
| 14 | 22.4 | 16 |
| 15 | 22.7 | 46 |
| 16 | 24.1 | 11 |
| 17 | 24.8 | 7 |
| 18 | 25.7 | 16 |
| 19 | 26.4 | 3 |
| 20 | 26.7 | 9 |
| 21 | 27.0 | 11 |
| 22 | 27.7 | 6 |
| 23 | 27.8 | 10 |
| 24 | 28.1 | 21 |
| 25 | 28.5 | 4 |
| 26 | 30.3 | 1 |
| 27 | 30.8 | 1 |
| 28 | 31.4 | 1 |
| 29 | 32.5 | 3 |
| 30 | 32.8 | 10 |
| 31 | 34.0 | 3 |
| 32 | 35.3 | 3 |
| 33 | 36.2 | 1 |
| 34 | 37.1 | 2 |
| 35 | 37.9 | 3 |
| 36 | 39.1 | 1 |

Regarding form (I), it is prepared by crystallization of compound of formula (VIIb*-H) in a solvent, wherein the solvent is preferably selected from the group consisting of ethyl acetate, methanol, $CH_2Cl_2$, acetonitrile, isopropyl acetate, acetone, ethanol, isopropanol, toluene, butanol, isobutanol, t-butanol, tetrahydrofuran, methyltetrahydrofuran, cyclohexane and mixture thereof. More preferably the solvent is ethyl acetate.

Regarding the temperature of the crystallization process there is no specific limitation provided that the crystalline form (I) is obtained. Preferably, the temperature is in the range of from −30 to 70° C., more preferably 10 to 50° C., even more preferably 10 to 30° C.

The present invention is further directed to the sulphate salt of the compound of formula (VIIb-H) and (VIIb*-H), more preferably of formula (VIIb*-H), the sulphate salt having formulae

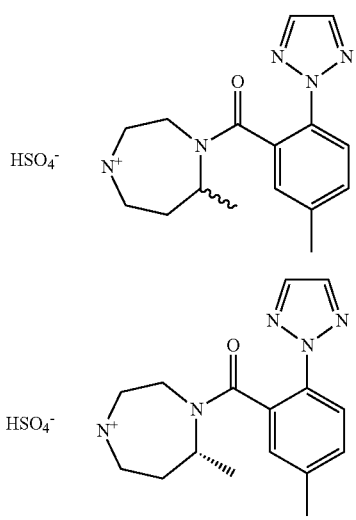

Regarding the sulphate salt of formula (VIIb-S) or formula (VIIb*-S), it is prepared by any suitable method for preparing sulphate salt. In an embodiment, the sulphate salt of formula (VIIb-S) or of formula (VIIb*-S), it is prepared by adding $H_2SO_4$ to a solution comprising the compound of formula (VIIb-H) or of formula (VIIb*-H). Preferably the solvent of the solution is selected from the group consisting of ethyl acetate, methanol, $CH_2Cl_2$, acetonitrile, isopropyl acetate, acetone, ethanol, isopropanol, toluene, butanol, isobutanol, t-butanol, tetrahydrofuran, methyltetrahydrofuran, cyclohexane and mixture thereof, wherein the solvent is preferably selected from the group consisting of ethyl acetate, methanol, $CH_2Cl_2$ and mixture thereof.

Preferably the sulphate salt of formula (VIIb-S) and of formula (VIIb*-S) is crystalline.

In an embodiment, the crystalline sulphate of formula (VIIb*-S) is in the crystalline form (I-S). Crystalline form (I-S) has an X-ray powder diffraction pattern comprising a peak at 2-theta angle of approximately 14.3°±0.2°, more preferably has an X-ray powder diffraction pattern comprising peaks at 2-theta angles of 7.8°±0.2°, 8.6°±0.2°, 9.1°±0.2°, 14.3°±0.2, 17.4°±0.2°, 19.7°±0.2°, wherein the X-ray powder diffraction pattern is measured at a temperature in the range of from 15 to 25° C. with Cu-K$\alpha_{1,2}$ radiation having a wavelength of 0.15419 nm.

Preferably the X-ray powder diffraction pattern of crystalline form (I-S) further comprises peaks at 2-theta angles of 14.7±0.2°, 21.7°±0.2°, 24.0°±0.2°.

A peak listing of the XRPD of form (I-S) is presented in Table 3.

TABLE 3

| No. | Pos. [°2Th. | Rel. Int. [%] |
| --- | --- | --- |
| 1 | 7.8 | 17 |
| 2 | 8.6 | 72 |
| 3 | 9.1 | 24 |
| 4 | 13.8 | 9 |
| 5 | 14.3 | 79 |
| 6 | 14.7 | 30 |
| 7 | 15.0 | 12 |
| 8 | 15.9 | 23 |
| 9 | 17.4 | 77 |
| 10 | 18.2 | 3 |
| 11 | 18.9 | 1 |
| 12 | 19.7 | 100 |
| 13 | 19.9 | 27 |
| 14 | 20.7 | 4 |
| 15 | 21.1 | 17 |
| 16 | 21.7 | 30 |
| 17 | 23.1 | 5 |
| 18 | 24.0 | 57 |
| 19 | 24.5 | 12 |
| 20 | 24.9 | 19 |
| 21 | 25.3 | 26 |
| 22 | 25.5 | 10 |
| 23 | 25.7 | 8 |
| 24 | 26.2 | 8 |
| 25 | 26.5 | 5 |
| 26 | 26.9 | 2 |
| 27 | 27.4 | 2 |
| 28 | 27.8 | 13 |
| 29 | 28.2 | 4 |
| 30 | 28.8 | 22 |
| 31 | 29.8 | 6 |
| 32 | 30.2 | 12 |
| 33 | 30.7 | 2 |
| 34 | 31.6 | 1 |
| 35 | 32.2 | 5 |
| 36 | 32.6 | 4 |
| 37 | 33.7 | 3 |
| 38 | 34.7 | 2 |
| 39 | 34.9 | 2 |
| 40 | 35.8 | 2 |
| 41 | 36.8 | 1 |
| 42 | 37.3 | 2 |
| 43 | 38.1 | 2 |
| 44 | 39.0 | 2 |

An XRPD of crystalline form (I-S) is disclosed in FIG. 5.

Regarding the crystalline form (I-S) of the compound of formula (VIIb*-S) it is prepared by adding $H_2SO_4$ to a solution comprising the compound of formula (VIIb*). Preferably the solvent of the solution is selected from the group consisting of ethyl acetate, methanol, $CH_2Cl_2$, acetonitrile, isopropyl acetate, acetone, ethanol, isopropanol, toluene, butanol, isobutanol, t-butanol, tetrahydrofuran, methyltetrahydrofuran, cyclohexane and mixture thereof, wherein the solvent is preferably selected from the group consisting of ethyl acetate, methanol, $CH_2Cl_2$ and a mixture thereof.

Regarding form (I-S), it is prepared by crystallization in a solvent of the sulphate salt of formula (VIIb*-S), wherein the solvent is preferably selected from the group consisting of ethyl acetate, methanol, $CH_2Cl_2$ and a mixture thereof.

Regarding the temperature of the crystallization process there is no specific limitation provided that the crystalline form (I-S) is obtained. Preferably the temperature is in the range of from −30 to 70° C., more preferably in the range of from 10 to 50° C., even more in the range of from 10 to 30° C.

The present invention is further directed to the hydrochloride salt of the compound of formula (VIIb) or of formula (VIIb*) having formulae (VIIb-Cl) and (VIIb*-Cl)

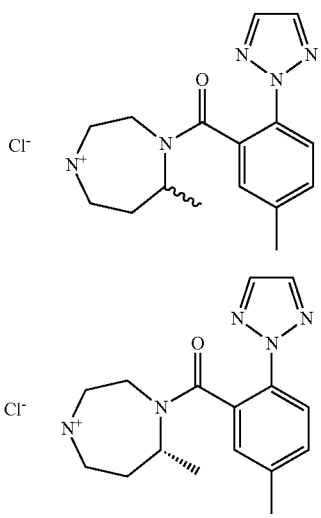

(VIIb-Cl)

(VIIb*-Cl)

Regarding the hydrochloride salt of formula (VIIb-Cl) or formula (VIIb*-Cl), it is prepared by any suitable method for preparing hydrochloride salt.

Preferably, the hydrochloride salt of formula (VIIb-Cl) or of formula (VIIb*-Cl) is crystalline.

In an embodiment, the crystalline hydrochloride salt of formula (VIIb*-Cl) is the crystalline form (I-Cl). Crystalline form (I-Cl) has an X-ray powder diffraction pattern comprising a peak at 2-theta angle of approximately 15.2°±0.2°, more preferably has an X-ray powder diffraction pattern comprising peaks at 2-theta angles of 10.5±0.2°, 11.5°±0.2°, 15.2°±0.2°, 16.6°±0.2, 22.4°±0.2°, the X-ray powder diffraction pattern is measured at a temperature in the range of from 15 to 25° C. with Cu-K$\alpha_{1,2}$ radiation having a wavelength of 0.15419 nm.

The X-ray powder diffraction pattern of form (I-Cl) preferably further comprises peaks at 2-theta angles of 18.5.±0.2°, 23.9°±0.2°.

A peak listing of the XRPD of form (I-Cl) is presented in Table 4.

TABLE 4

| No. | Pos. [°2Th.] | Rel. Int. [%] |
|---|---|---|
| 1 | 9.6 | 7 |
| 2 | 10.5 | 68 |
| 3 | 11.5 | 15 |
| 4 | 12.0 | 11 |
| 5 | 12.9 | 15 |
| 6 | 14.8 | 12 |
| 7 | 15.2 | 100 |
| 8 | 16.3 | 15 |
| 9 | 16.6 | 36 |
| 10 | 17.3 | 2 |
| 11 | 17.5 | 9 |
| 12 | 18.3 | 4 |
| 13 | 18.5 | 18 |
| 14 | 18.9 | 7 |
| 15 | 19.4 | 12 |
| 16 | 19.5 | 10 |
| 17 | 19.8 | 4 |
| 18 | 21.1 | 10 |
| 19 | 21.2 | 15 |
| 20 | 21.4 | 8 |
| 21 | 22.4 | 76 |
| 22 | 23.6 | 25 |
| 23 | 23.9 | 28 |

TABLE 4-continued

| No. | Pos. [°2Th.] | Rel. Int. [%] |
|---|---|---|
| 24 | 24.4 | 2 |
| 25 | 25.2 | 20 |
| 26 | 25.9 | 7 |
| 27 | 26.1 | 10 |
| 28 | 26.7 | 4 |
| 29 | 27.3 | 6 |
| 30 | 27.8 | 5 |
| 31 | 28.7 | 4 |
| 32 | 29.2 | 5 |
| 33 | 29.9 | 5 |
| 34 | 30.5 | 6 |
| 35 | 31.3 | 3 |
| 36 | 31.5 | 5 |
| 37 | 31.8 | 2 |
| 38 | 32.4 | 4 |
| 39 | 32.7 | 5 |
| 40 | 33.6 | 1 |
| 41 | 34.1 | 2 |
| 42 | 35.1 | 4 |
| 43 | 35.9 | 3 |
| 44 | 36.3 | 4 |
| 45 | 37.0 | 1 |
| 46 | 37.9 | 1 |
| 47 | 38.3 | 4 |
| 48 | 39.0 | 2 |
| 49 | 39.6 | 3 |

An XRPD of crystalline form (I-Cl) is disclosed in FIG. 6.

Regarding the hydrochloride salt of formula (VIIb-Cl) or formula (VIIb*-Cl) it is prepared by adding HCl, preferably methanolic HCl to a solution comprising the compound of formula (VIIb) or of formula (VIIb*).

Regarding crystalline form (I-Cl), it is prepared by crystallization in a solvent of the hydrochloride salt of formula (VIIb*-Cl), wherein the solvent is preferably selected from the group consisting of ethyl acetate, methanol, $CH_2Cl_2$, acetonitrile, isopropyl acetate, acetone, ethanol, isopropanol, toluene, butanol, isobutanol, t-butanol, tetrahydrofuran, methyltetrahydrofuran, cyclohexane and a mixture thereof, the solvent is more preferably selected from the group consisting of ethyl acetate, methanol, $CH_2Cl_2$ and a mixture thereof.

Regarding the temperature of the crystallization process there is no specific limitation provided that the crystalline form (I-Cl) is obtained. Preferably the temperature is in the range of from −30 to 70° C., more preferably in the range of from 10 to 50° C., even more preferably in the range of from 10 to 30° C.

Use as Antagonists of Orexin Receptor Activity

The compound of formula (IX) obtained or obtainable by the above-described process or a pharmaceutical composition comprising this compound is useful in a method of antagonizing orexin receptor activity. Thus, the present invention also describes the compound of formula (IX) obtained or obtainable by the above-described process or a pharmaceutical composition comprising this compound for use as antagonists of orexin receptor activity, in particular for use in treating, preventing, ameliorating, controlling or reducing the risk of a variety of neurological and psychiatric disorders associated with orexin receptors, in particular for enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; treating, controlling, ameliorating or reducing the risk of epilepsy, including absence epilepsy; treating or controlling pain, including neuropathic pain; treating or controlling Parkinson's disease; treating or controlling psychosis; or treating, controlling, ameliorating or reducing the risk of schizophrenia, in a mammalian patient in need thereof.

In particular, the compound of formula (IX) obtained or obtainable by the above described process or a pharmaceutical composition comprising this compound is used for treating or preventing a sleep disorder, in particular for enhancing the quality of sleep or for treating insomnia in a mammalian patient, in particular, for treating or controlling obesity in a mammalian patient.

As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such a disease or disorder.

By way of example, the following particularly preferred embodiments of the invention are mentioned:

1. A process for the preparation of a compound of formula (A)

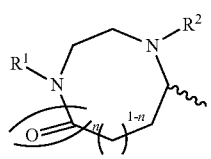

or a pharmaceutically acceptable salt or solvate thereof, wherein (A) is preferably

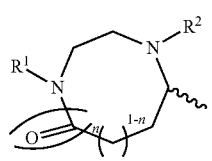

wherein $R^1$ is selected from the group consisting of H, $PG^1$ and $R^A$ with $R^A$ being

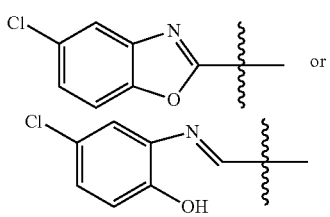

and wherein $R^2$ is selected from the group consisting of H, $PG^2$ and $R^B$ with $R^B$ being

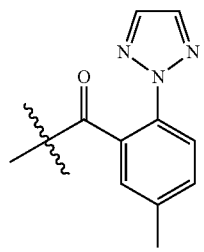 [SMILES: *C(=O)c1cc(C)ccc1-n1nccn1]

and wherein $PG^1$ and $PG^2$ are, independently of each other, suitable protecting groups, and wherein n is 0 or 1, the process comprising (a) providing a compound of formula (II)

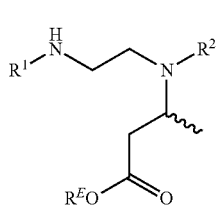

wherein $R^E$ is selected from the group consisting of H, alkyl, aryl, alkylaryl, heteroaryl cycloalkyl and heterocycloalkyl, more preferably wherein $R^E$ is alkyl, more preferably wherein $R^E$ is methyl, ethyl or propyl, more preferably wherein $R^E$ is methyl, (b) reacting the compound of formula (II) with a base and optionally reducing the compound
to give the compound of formula (A), (c) optionally crystallizing the compound of formula (A).

2. The process according to embodiment 1, wherein the compound of formula (A) has the structure of formula (Ia)

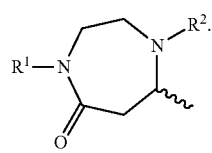

3. The process according to embodiment 1 or 2, wherein the compound of formula (A) has the structure of formula (Ia*)

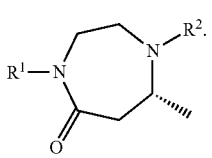

4. The process according to embodiment 1, wherein the compound of formula (A) has the structure of formula (Ib)

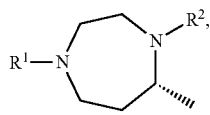
(Ib)

and wherein in step (b) upon reaction with the base a compound of formula (Ia) is formed,

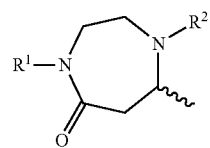
(Ia)

and wherein step (b) further comprises reducing the compound of formula (Ia).

5. The process according to embodiment 4, wherein the compound of formula (A) has the structure of formula (Ib*)

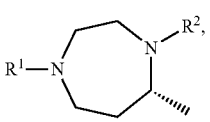
(Ib*)

and wherein in step (b) upon reaction with the base a compound of formula (Ia*) is formed,

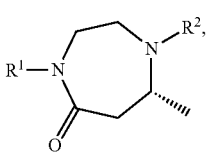
(Ia*)

and wherein step (b) further comprises reducing the compound of formula (Ia*).

6. The process according to any of embodiments 1 to 5, wherein PG$^1$ is selected from the group consisting of Benzyl (Bn), t-butyloxycarbonyl (Boc), Cbz (carboxybenzyl), PNZ (p-Nitrobenzylcarbamoyl)), allyloxycarbonyl (Alloc), Trifluoroacetate and Phthalimide.

7. The process according to any of embodiments 1 to 6, wherein PG$^2$ is selected from the group consisting of Benzyl, t-butyloxycarbonyl (Boc), Cbz (carboxybenzyl), PNZ, allyloxycarbonyl (Alloc), Trifluoroacetate and Phthalimide.

8. The process according to any of embodiments 1 to 7, wherein R1 is selected from the group consisting of H,

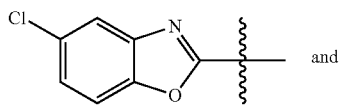
and

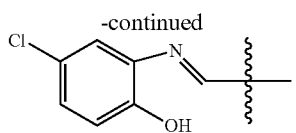

more preferably, wherein R1 is H.

9. The process according to any of embodiments 1 to 8, wherein step (b) comprises
(b1) reacting the compound of formula (II) with a base to give a composition comprising a compound of formula (Ia)

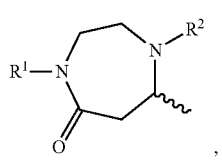
(Ia)

preferably a compound of formula (Ia*)

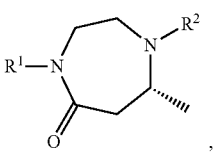
(Ia*)

(b2) optionally purifying the composition obtained in (b1),
(b3) optionally reducing the compound of formula (Ia), preferably of formula (Ia*), to give a compound of formula (Ib)

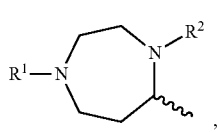
(Ib)

preferably (Ib*)

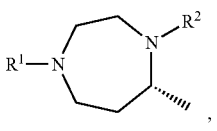
(Ib*)

(b4) optionally purifying the compound obtained in (b3), wherein preferably the purifying comprises crystallizing the compound obtained in (b3).

10. The process according to embodiment 9, wherein (b1) is carried out in an organic solvent, more preferably in a solvent selected from the group consisting of methanol, ethanol, propanol, isopropanol, butanol, s-butanol, t-butanol, tetrahydrofuran, 2-methyltetrahydrofuran, methyl-tertbutylether, diethylether, diisopropylether, toluene, acetonitrile and mixtures of two or more thereof 11. The process according to embodiment 9 or 10, wherein step (b1) is carried out at a temperature in the range of from −20° C. to 80° C., more preferably in the range of from 0 to 50, more preferably in the range of from 20 to 30° C. During the reaction, the temperature may be varied or held essentially constant.

12. The process according to any of embodiments 9 to 11, wherein (b3) is carried out in an organic solvent, more preferably in a solvent selected from the group consisting of methanol, ethanol, nPrOH, i-PrOH, THF, 2-MeTHF, MTBE, DIPET, toluene, acetonitrile, $CH_2Cl_2$ and mixtures of two or more thereof.

13. The process according to any of embodiments 9 to 12, wherein in step (b3), the compound is reduced by reaction with a reducing agent selected from the group consisting of $NaBH_4$, $NaCNBH_3$, $NaBH(OAc))_3$, $LiAlH_4$, $LiBH_4$ and $H_2$ in the presence of at least one transition metal.

14. The process according to any of embodiments 1 to 13, wherein compound (II) consists of a mixture of

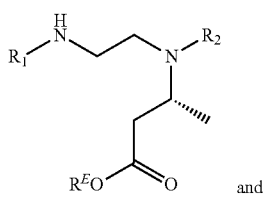
(II*)

and

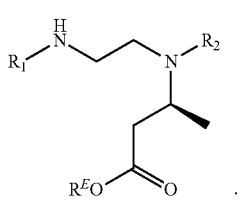
(II**)

15. The process of embodiment 14, wherein compound (II) contains of from 20 to 75% by weight % of the compound of formula (II*) based on the total weight of the sum of (II*) and (II**) and wherein mixture is resolved by chiral resolution to give the compound (II*).

16. The process of embodiment 15, wherein the resolution is carried out by a process comprising
   (i) adding a single stereoisomer of a chiral acid and precipitating, preferably crystallizing, a chiral acid salt (S) of compound (II), thereby obtaining a mixture comprising the precipitated, preferably crystallized, tartaric acid salt (S) and the solvent,
   (ii) preferably separating the precipitated, preferably crystallized, chiral acid salt (S) of the compound of formula (II) from the mixture obtained in (i), wherein the chiral acid salt (S) contains at least 80% by weight of the chiral acid salt of the compound of formula (II*) based on the total weight of the chiral acid salt of the compound of formula (II),
   (iii) converting the chiral acid salt (S) to the free base.

17. A process of any of embodiments 1 to 17, wherein the compound has the structure

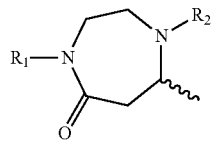
(Ia)

or is a pharmaceutically acceptable salt or solvate thereof, wherein (Ia) is preferably (Ia*)

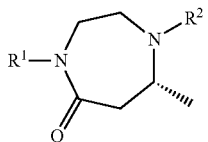
(Ia*)

and wherein $R^1$ is H and $R^2$ is $PG^2$.

18. The process according to any of embodiments 1 to 13, wherein step (a) comprises
   (a1) reacting a compound of formula (III)

(III)

with a compound of formula (IV)

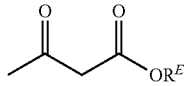
(IV)

to give a compound of formula (V)

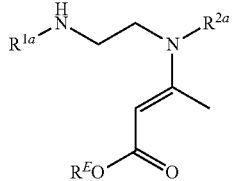
(V)

wherein $R^{1a}$ is H, $R^1$, $PG^1$, $R^A$, or $PG^{1a}$
and wherein $R^{2a}$ is H, $R^2$, $PG^2$, $R^B$ or $PG^{2a}$ and wherein $PG^{1a}$ and $PG^{2a}$ are, independently of each other, suitable protecting groups,
   (a2) optionally purifying the compound of formula (V),
   (a3) reducing the compound of formula (V),
   (a4) optionally replacing $R^{2a}$ and/or $R^{1a}$ with $R^1$ and/or $R^2$,
to give the compound of formula (II).

19. The process of embodiment 18, wherein in step (a3), a compound having the structure

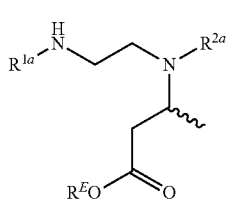
(IIa)

is obtained.

20. The process of embodiment 19, wherein compound (IIa) contains of from 20 to 75% by weight % of the compound of formula (IIa*) based on the total weight of the sum of (IIa*) and (IIa**)

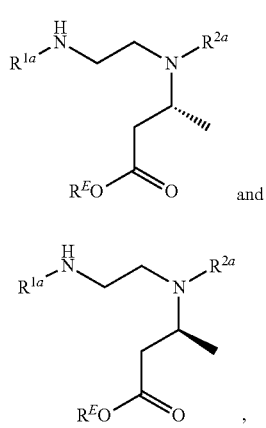

and wherein the mixture is resolved by chiral resolution to give the compound (IIa*).

21. The process of embodiment 20, wherein the resolution is carried out by a process comprising
   (ia) adding a single stereoisomer of a chiral acid and precipitating, preferably crystallizing, a chiral acid salt (Sa) of compound (IIa), thereby obtaining a mixture comprising the precipitated, preferably crystallized, tartaric acid salt (Sa) and the solvent,
   (iia) preferably separating the precipitated, preferably crystallized, chiral acid salt (Sa) of the compound of formula (IIa) from the mixture obtained in (ia), wherein the chiral acid salt (S) contains at least 80% by weight of the chiral acid salt of the compound of formula (IIa*) based on the total weight of the chiral acid salt of the compound of formula (IIa),
   (iiia) converting the chiral acid salt (Sa) to the free base.

22. The process of any of embodiments 1 to 21, wherein step (a) comprises
   (a1) reacting a compound of formula (III)

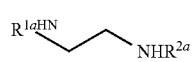
(III)

with a compound of formula (IV)

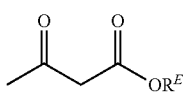
(IV)

to give a compound of formula (V)

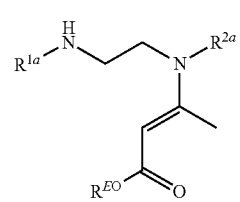
(V)

wherein $R^{1a}$ is $PG^1$ and wherein $R^{2a}$ is H, and $PG^{1a}$ is a suitable protecting group, preferably a Boc group, (a2) optionally purifying the compound of formula (V),
(a3) reducing the compound of formula (V) to give a compound of formula (IIa), wherein $R^{1a}$ is $PG^1$ and wherein $R^{2a}$ is H
(a4) replacing $R^{2a}$ with

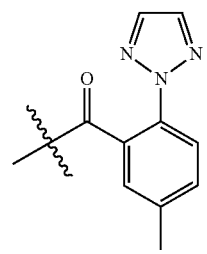 [SMILES: *C(=O)c1cc(C)ccc1-n1nccn1]

by reacting a compound of formula (IIa) with a compound of formula (XI)

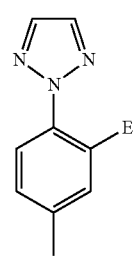
(XI)

wherein E is —COOH or a reactive carboxy group, and replacing $R^{1a}$ with H by removing the protecting group $PG^1$.
to give the compound of formula (II) in which $R^1$ is H and $R^2$ is

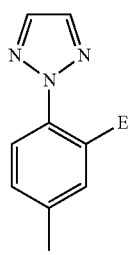

23. The process according to any of embodiments 18 to 22, wherein step (a1) is carried out at a temperature in the range of 0 to 80 C, more preferably in the range of from 10 to 50° C., more preferably in the range of from 20 to 35° C.
24. The process according to any of embodiments 18 to 23, wherein (a1) is carried out in an organic solvent, more preferably in a solvent methanol, ethanol, trifluoroethanol (TFE), dichloromethane, DMF, DMSO, NMP, methanol, ethanol, propanol, isopropanol, butanol, s-butanol, t-butanol, tetrahydrofuran, 2-methyltetrahydrofuran, methyltertbutylether, diethylether, diisopropylether, toluene, acetonitrile and mixtures of two or more thereof.
25. The process according to any of embodiments 18 to 24, wherein (a1) is carried in the presence of a catalysing agent, such as a dehydrating reagent or an acidic catalyst, preferably in the presence of $SiO_2$ or a molecular sieve or a mixture thereof.
26. The process according to any of embodiments 28 to 25, wherein (a3) is carried out in an organic solvent, more preferably in a solvent selected from the group consisting of methanol, ethanol, trifluoroethanol (TFE), dichloromethane, DMF, DMSO, NMP, methanol, ethanol, propanol, isopropanol, butanol, s-butanol, t-butanol, tetrahydrofuran, 2-methyltetrahydrofuran, methyltertbutylether, diethylether, diisopropylether, toluene, acetonitrile and mixtures of two or more thereof. Preferably, the solvent is methanol or TFE.
27. The process according to any of embodiments 18 to 26, wherein (a3) is carried out at a temperature in the range of from 10 to 100° C., more preferably in the range of from 20 to 60° C., more preferably at 25 to 40° C.
28. The process according to any of embodiments 18 to 27, wherein in step (a3), the compound is reduced with Pd/C.
29. The process according to any of embodiments 18 to 28, wherein in step (a3), the compound is stereoselectively reduced to give a compound of formula (IIa*)

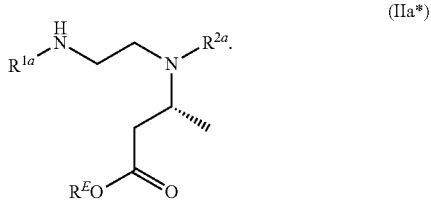

(IIa*)

30. The process according to embodiment 29, wherein the metal catalyst is selected from the group consisting of a catalyst comprising Pd, Fe, Ir, Rh or a mixture of two or more thereof.
31. The process according to any of embodiments 1 to 25, wherein the base in step (b) is selected from the group consisting of $NaOR^E$, Na-tert.butoxid, K-tert.butoxid, NaNH2, DBU, Tetramethylguanidin, Na—$CH_2S(O)CH_3$ and mixtures of two or more thereof, with $R^E$ being selected from the group consisting of alkyl, aryl, alkylaryl, heteroaryl cycloalkyl and heterocycloalkyl, more preferably wherein $R^E$ is alkyl, more preferably wherein $R^E$ methyl, ethyl or propyl, more preferably wherein $R^E$ is methyl, most preferably wherein the base is sodium methanolate.
32. The process of any of embodiments 1 to 31, wherein compound (A) has the structure (Ia)

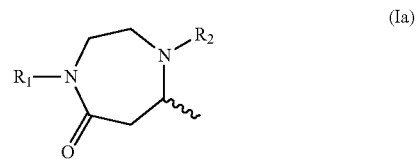

(Ia)

or is a pharmaceutically acceptable salt or solvate thereof, wherein (Ia) is preferably (Ia*)

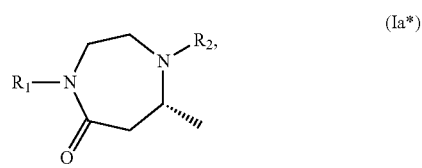

(Ia*)

and wherein $R^1$ is H and $R^2$ is $PG^2$, the process comprising
(a) providing a compound of formula (II)

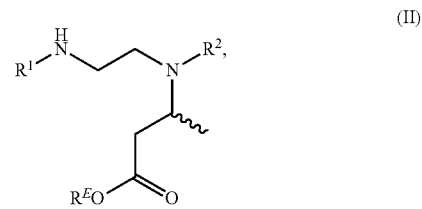

(II)

preferably of formula (II*),
wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl,
(b) reacting the compound of formula (II), preferably of formula (II*), with a base,
to give the compound of formula (Ia), with $R^1$ being H and with $R^2$ being $PG^2$, preferably (Ia*) with $R^1$ being H and with $R^2$ being $PG^2$.
33. The process of any of embodiments 1 to 31, wherein compound (A) has the structure (Ib)

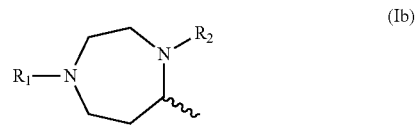

(Ib)

or is a pharmaceutically acceptable salt or solvate thereof, wherein (Ib) is preferably (Ib*),

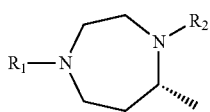
(Ib*)

and wherein R¹ is H and R² is PG², the process comprising (a) providing a compound of formula (II),

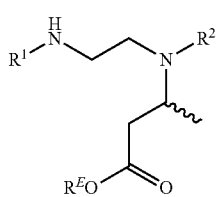
(II)

preferably (II*),
wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, (b) reacting the compound of formula (II) with a base, and reducing the resulting compound of formula (Ia), to give the compound of formula (Ib), with R¹ being H and with R² being PG² preferably (Ib*) with R¹ being H and with R² being PG²

(c) optionally preparing a salt of the compound of formula (Ib), wherein preferably the slat is an hydrochloride salt or a sulphate salt, (d) optionally crystallizing the compound obtained in (b) or obtained in (c).

34. The process of any of embodiments 1 to 33, wherein compound (A) has the structure (VIIa) with R¹ being H

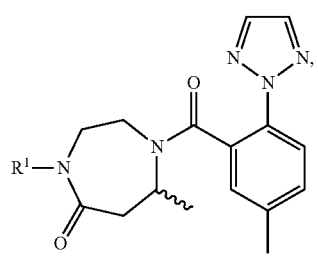
(VIIa)

preferably (VIIa*)

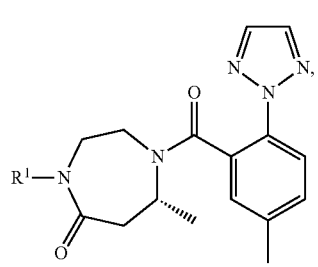
(VII*a)

the process comprising (a) providing a compound of formula (II),

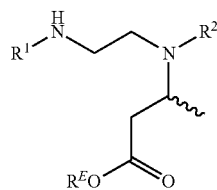
(II)

preferably (II*)

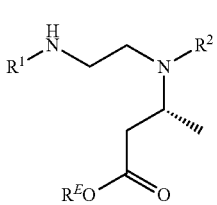
(II*)

wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, and wherein R² is

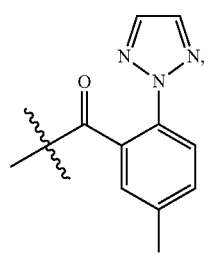

(b) reacting the compound of formula (II), preferably (II*), with a base to give the compound of formula (VIIa), preferably (VIIa*).

35. The process of any of embodiments 1 to 33, wherein compound (A) has the structure (VIIb) with R¹ being H

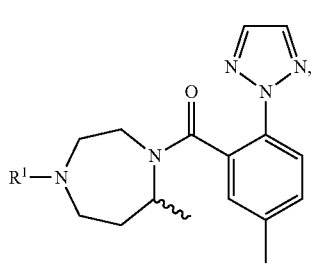
(VIIb)

preferably (VIIb*)

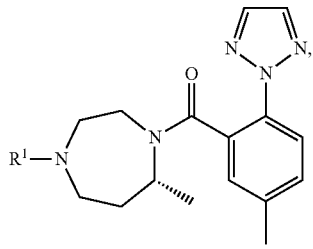
(VIIb*)

the process comprising
(a) providing a compound of formula (II),

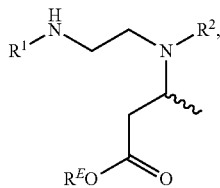
(II)

preferably (II*), wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, and wherein $R^2$ is

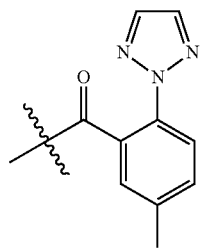 [SMILES: *C(=O)c1cc(C)ccc1-n1nccn1]

(b) reacting the compound of formula (II), preferably (II*), with a base, and reducing the resulting compound to give a compound of formula (VIIb), preferably (VIIb*)

wherein (b) comprises
(b1-1) optionally preparing a salt of the compound of formula (VIIb) in which $R^1$ is H, preferably (VIIb*) in which $R^1$ is H and preferably wherein the salt is an hydrochloride salt or a sulphate salt,
(b1-2) optionally purifying the compound obtained in (b) or (b1-1), wherein preferably purifying comprises crystallizing the compound obtained in (b) or (b1-1),
(b1-3) optionally transforming the crystalline salt of (b1-2) in the free base of formula (VIIb), preferably (VIIb*).

36. The process of any of embodiments 1 to 33, wherein compound (A) has the structure

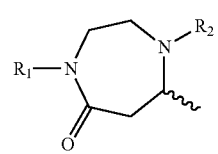
(Ia)

or is a pharmaceutically acceptable salt or solvate thereof, wherein (Ia) is preferably (Ia*)

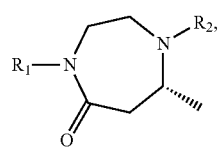
(Ia*)

and wherein $R^1$ is $R^A$ with $R^A$ being

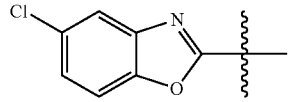 [SMILES: *c1nc2cc(Cl)ccc2o1]

and $R^2$ is $PG^2$, the process comprising
(a) providing a compound of formula (II)

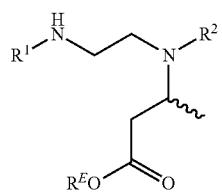
(II)

wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, wherein $R^1$ is $R^A$ with $R^A$ being

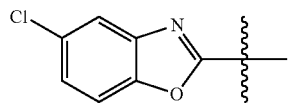 [SMILES: *c1nc2cc(Cl)ccc2o1]

and $R^2$ is $PG^2$, preferably the compound of formula (Ia*), wherein $R^1$ is $R^A$ with $R^A$ being

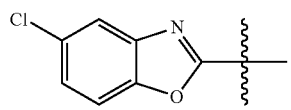 [SMILES: *c1nc2cc(Cl)ccc2o1]

and $R^2$ is $PG^2$,
(b) reacting the compound of formula (II) with a base, to give the compound of formula (Ia), wherein $R^1$ is $R^A$ with $R^A$ being

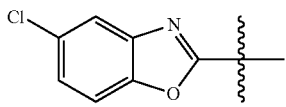 [SMILES: *c1nc2cc(Cl)ccc2o1]

and $R^2$ is $PG^2$, preferably the compound of formula (Ia*), wherein $R^1$ is $R^A$ with $R^A$ being

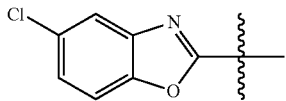 [SMILES: *c1nc2cc(Cl)ccc2o1]

and $R^2$ is $PG^2$, or
compound (A) has the structure

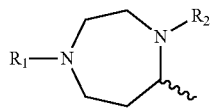
(Ib)

or is a pharmaceutically acceptable salt or solvate thereof, wherein (Ia) is preferably (Ia*)

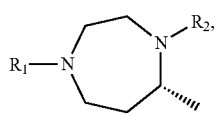
(Ib*)

and wherein $R^1$ is $R^A$ with $R^A$ being

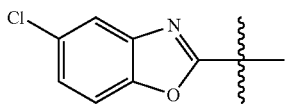 [SMILES: *c1nc2cc(Cl)ccc2o1]

and $R^2$ is $PG^2$, the process comprising
(a) providing a compound of formula (II)

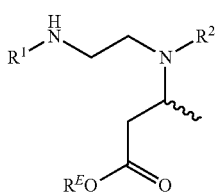
(II)

wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, wherein $R^1$ is $R^A$ with $R^A$ being

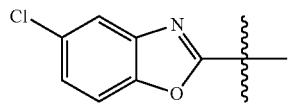 [SMILES: *c1nc2cc(Cl)ccc2o1]

and $R^2$ is $PG^2$, preferably the compound of formula (Ia*), wherein $R^1$ is $R^A$ with $R^A$ being

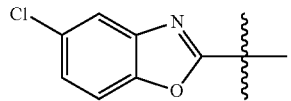 [SMILES: *c1nc2cc(Cl)ccc2o1]

and $R^2$ is $PG^2$,
(b) reacting the compound of formula (II) with a base, and reducing the resulting compound
to give the compound of formula (Ib),
wherein $R^1$ is $R^A$ with $R^A$ being

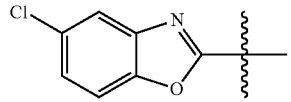

and $R^2$ is $PG^2$, preferably the compound of formula (Ia*), wherein $R^1$ is $R^A$ with $R^A$ being

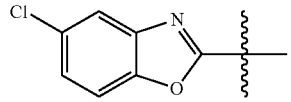 [SMILES: *c1nc2cc(Cl)ccc2o1]

and $R^2$ is $PG^2$.

37. The process according to any of embodiments 1 to 33, wherein the compound of formula (A) has the structure of formula (IX)

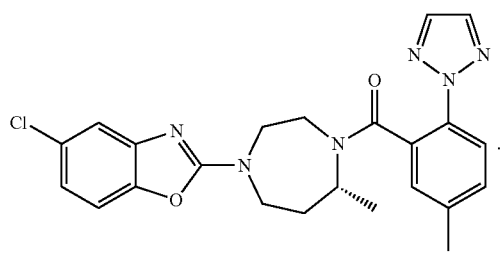
(IX)

38. The process according to any of embodiments 1 to 37, wherein $R^2$ in the compound of formula (A) is H, and wherein in (b) a compound of formula (A1) consisting of an enantiomeric mixture of the compounds (A1*) and (A1**) is obtained

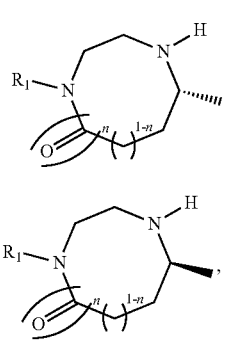

(A1*)

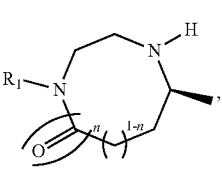

(A1**)

wherein the compound of formula (A1) contains of from 20 to 75% by weight, of the compound of formula (A1*) based on the total weight of the sum of (A1*) and (A1**), step (b) further comprising (I) forming a chiral acid salt, preferably a tartaric acid salt, (T*) of at least part of the compound of formula (A1) by treating the compound of formula (A1) with a single stereoisomer of a chiral acid salt, preferably of a tartaric acid derivative selected from the group consisting of Ditoluoyl tartaric acid, Dibenzoyl tartaric acid, Dianisoyl tartaric acid, Dibenzoyl tartaric acid mono(dimethylamide) and a mixture of two or more thereof, in a suitable solvent, and precipitating, preferably crystallizing, at least part of the tartaric acid salt (T*) formed, thereby obtaining a mixture comprising the precipitated, preferably crystallized, tartaric acid salt (T) and the solvent;

(II) preferably separating the precipitated, preferably crystallized, chiral acid salt (T) of the compound of formula (A1) from the mixture obtained in (I), wherein the chiral acid salt (T) of the compound of formula (A1) contains at least 80% by weight of the chiral acid salt of the compound of formula (A1*) based on the total weight of the chiral acid salt of the compound of formula (A1), (III) converting the chiral acid salt (T) of (A1) to the free base (A1*), wherein (A) is preferably (A1*) or wherein (A1*) is converted in further steps to give (A).

39. The process according to embodiment 38, wherein the chiral acid salt (T) of the compound formula (A1) contains at least 90% by weight, more preferably at least 95% by weight, more preferably at least 96% by weight, more preferably at least 97% by weight, more preferably at least 98% by weight, more preferably at least 99% by weight, more preferably at least 99.5% by weight, more preferably at least 99.9% by weight, of the tartaric salt of the compound of formula (A1*), based on the total weight of chiral acid salt of the compound of formula (A1).

40. The process according to embodiment 38 or 39, wherein the compound of formula (A1) employed in step (I) contains of from 40 to 60% by weight of the compound of formula (A1*) based on the total weight of the sum of (A1*) and (A1**).

41. The process of any of embodiments 38 to 40, wherein
n is 1 and the chiral acid is di-toluoyl-L-tartaric acid (LTTA), or
n is 0, and the chiral acid is di-benzoyl-D-tartaric acid (DBTA).

42. The process of embodiment 35 to 39, wherein the suitable solvent in step (I) is selected from the group consisting of selected from the group consisting of consisting of EtOH, i-PrOH, nPrOH, acetone, toluene, MTBE, $CH_2Cl_2$, ethyl acetate, acetone, isopropanol, methanol, water, formic acid ethyl ester, isopropyl acetate, propyl acetate, butyl acetate, acetonitrile, tetrahydrofuran, dichloromethane, methylisobutylketone, toluene, hexane, cyclohexane, heptane and mixtures of two or more thereof.

43. Process for the preparation of a compound of formula (IX), comprising
(A) preparing a compound of formula (A) according to the method of any of embodiments 1 to 42, wherein in case n=0, at least one of $R^A$ or $R^B$ is H or a protecting group,
(B) transforming the compound of step (A) into the compound of formula (IX).

44. The process of embodiment 43, wherein (A) comprises providing a compound of formula (Ia) by a process comprising
(a) providing a compound of formula (II)

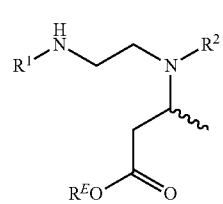

(II)

wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, wherein $R^1$ is H and $R^2$ is $PG^2$, (b) reacting the compound of formula (II) with a base, to give the compound of formula (Ia), with $R^1$ being H and with $R^2$ being $PG^2$, preferably (Ia*) with $R^1$ being H and with $R^2$ being $PG^2$.

45. The process of embodiment 44, wherein step (B) comprises
(c1) removal of the protecting group $PG^2$,
(d1) reacting the compound of formula (Ia) with $R^1$ and $R^2$ being H with a compound of formula

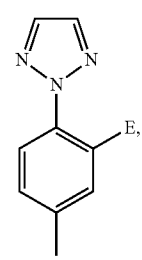

(XI)

wherein E is —COOH or a reactive carboxy group, to give a compound of formula (VIIa), in which $R^1$ is H,

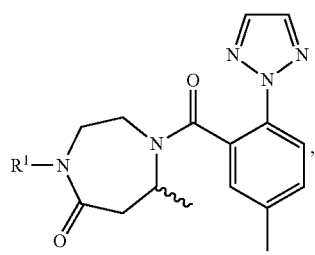
(VIIa)

preferably

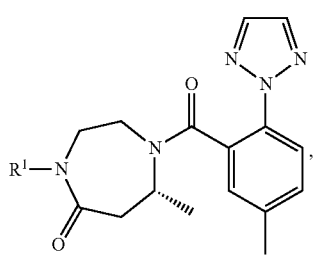
(VIIa*)

(e1) reducing the compound, to give a compound of formula (VIIb), in which $R^1$ is H

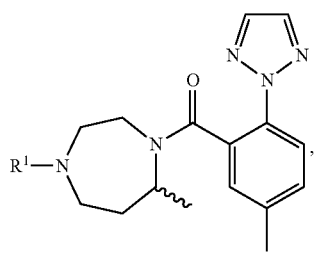
(VIIb)

preferably

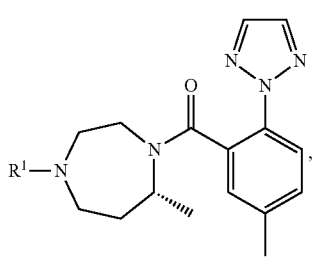
(VIIb*)

(f1) reacting the compound of formula (VIIb), preferably (VIIb*), with a compound of formula (XII)

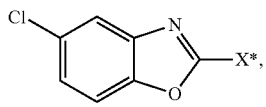
(XII)

wherein X* is a leaving group, preferably Cl, S, SMe, SEt, Br, more preferably —Br or —Cl, more preferably —Cl wherein (e1) optionally comprises (e1-1) preparing a salt of the compound of formula (VIIb) in which $R^1$ is H, preferably (VIIb*) in which $R^1$ is H and preferably wherein the salt is an hydrochloride salt or a sulphate salt, (e1-2) optionally purifying the compound obtained in (e1) or (e1-1), wherein preferably purifying comprises crystallizing the compound obtained in (e1) or (e1-1), (e1-3) optionally transforming the crystalline salt of (e1-2) in the free base of formula (VIIb), preferably (VIIb*).

46. The process of embodiment 43, comprising (A) providing a compound of formula (Ib) by a process comprising (a) providing a compound of formula (II), preferably (II*),

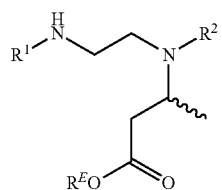
(II)

wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, wherein $R^1$ is H and $R^2$ is $PG^2$.

(b) reacting the compound of formula (II) with a base, to give the compound of formula (Ia)

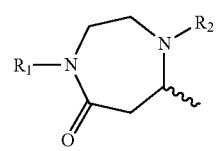
(Ia)

with $R^1$ being H and with $R^2$ being $PG^2$, preferably (Ia*) with $R^1$ being H and with $R^2$ being $PG^2$, and reducing the resulting compound of formula (Ia), preferably (Ia*), (B) transforming the compound of step (A) into the compound of formula (IX).

47. The process of embodiment 46, wherein step (B) comprises (c1) removal of the protecting group $PG^2$, (d1b) reacting the compound of formula (Ib) with $R^1$ and $R^2$ being H with a compound of formula (XI)

wherein E is —COOH or a reactive carboxy group, to give a compound of formula (VIIb), in which R¹ is H, (VIIb)

preferably (VIIb*)

(f1) reacting the with a compound of formula (VIIb), preferably (VIIb*), with a compound of formula (XII)

(XII)

wherein X* is a leaving group, preferably Cl and wherein
wherein (d1b) optionally comprises
(d1b-1) preparing a salt of the compound of formula (VIIb) in which R¹ is H, preferably (VIIb*) in which R¹ is H and preferably wherein the salt is an hydrochloride salt or a sulphate salt,
(d1b-2) optionally purifying the compound obtained in (d1b) or (d1b-1), wherein preferably purifying comprises crystallizing the compound obtained in (d1b) or (d1b-1),
(d1b-3) optionally transforming the crystalline salt of (d1b-2) in the free base of formula (VIIb), preferably (VIIb*).

48. The process of embodiment 43 comprising
(A) providing a compound of formula (VIIb) by a process comprising
(a) providing a compound of formula (II), preferably (IP), (II)

wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, and wherein $R^2$ is (b) reacting the compound of formula (II), preferably (II*), with a base to give the compound of formula (VIIa), preferably (VIIa*), and reducing the resulting compound to give a compound of formula (VIIb), preferably (VIIb*),
(B) transforming the compound of step (A) into the compound of formula (IX) wherein (b) optionally comprises
(b1-1) preparing a salt of the compound of formula (VIIb) in which R¹ is H, preferably (VIIb*) in which R¹ is H and preferably wherein the salt is an hydrochloride salt or a sulphate salt,
(b1-2) optionally purifying the compound obtained in (b) or (b1-1), wherein preferably purifying comprises crystallizing the compound obtained in (b) or (b1-1),
(b1-3) optionally transforming the crystalline salt of (b1-2) in the free base of formula (VIIb), preferably (VIIb*).

49. The process of embodiment 48, wherein step (B) comprises
(f1) reacting the compound of formula (VIIb), preferably (VIIb*), with a compound of formula (XII)

(XII)

wherein X* is a leaving group, preferably Cl.

50. The process of embodiment 43 comprising
   (A) providing a compound of formula (VIIa) by a process comprising
      (a) providing a compound of formula (II)

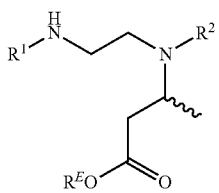

(II)

wherein $R^E$ is selected from the group consisting of H, alkyl, aryl, alkylaryl, heteroaryl, cycloalkyl and heterocycloalkyl, more preferably wherein $R^E$ is alkyl, more preferably wherein $R^E$ is methyl, ethyl or propyl, more preferably wherein $R^E$ is methyl, and wherein $R^2$ is

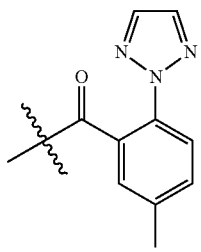

(b) reacting the compound of formula (II) with a base, to give the compound (VIIa), preferably (VIIa*), with $R^1$=H,
   (B) transforming the compound of step (A) into the compound of formula (IX).
51. The process of embodiment 50, wherein step (B) further comprises
   (e1) reducing the compound, to give a compound of formula (VIIb), in which $R^1$ is H, preferably (VIIb*) in which $R^1$ is H,
   (f1) reacting the compound of formula (VIIb), preferably (VIIb*), with a compound of formula (XII)

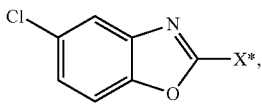

(XII)

wherein X* is a leaving group, preferably Cl and wherein (e1) optionally comprises
      (e1-1) preparing a salt of the compound of formula (VIIb), preferably (VIIb*) wherein preferably the salt is an hydrochloride salt or a sulphate salt,
      (e1-2) optionally purifying the compound obtained in (e1) or (e1-1), wherein preferably purifying comprises crystallizing the compound obtained in (e1) or (e1-1),
      (e1-3) optionally transforming the crystalline salt of (e1-2) in the free base of formula (VIIb), preferably (VIIb*).
52. A compound of formula (A) or a salt thereof, obtained or obtainable by a method of any of embodiments 1 to 42.

53. The compound of embodiment 52, wherein $R^1$ is H and $R^2$ is

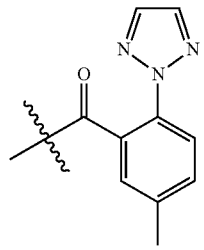

54. The compound of embodiment 53 or the salt thereof in crystalline form, wherein the compound preferably has the structure

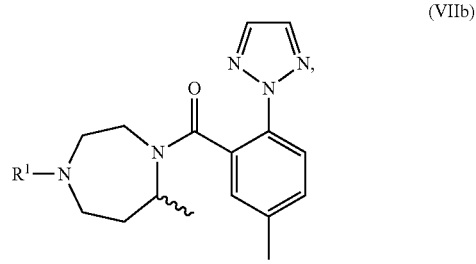

(VIIb)

more preferably the structure

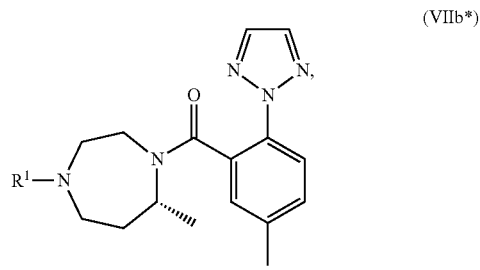

(VIIb*)

and wherein compound of formula (VIIb) wherein $R^1$ is H1) has an X-ray powder diffraction pattern comprising a peak at 2-theta angle of approximately 12.4°±0.2°, preferably has an X-ray powder diffraction pattern comprising peaks at 2-theta angles of approximately 4.8±0.2°, 12.4°±0.2°, 14.2°±0.2°, 19.9°±0.2° and 20.8°±0.2° or at approximately 7.7±0.2°, 11.4°±0.2°, 12.4°±0.2°, 16.2°±0.2° and 18.1°±0.2°, more preferably, at approximately 4.8±0.2°, 12.4°±0.2°, 14.2°±0.2°, 19.9°±0.2° and 20.8°±0.2°, wherein the X-ray powder diffraction pattern is measured at a temperature in the range of from 15 to 25° C. with Cu-K$\alpha_{1,2}$ radiation having a wavelength of 0.15419 nm or
   2) has an X-ray powder diffraction pattern comprising a peak at 2-theta angle of approximately 12.4°±0.2°, more preferably has an X-ray powder diffraction pattern comprising peaks at 2-theta angles of approximately 4.8±0.2°, 12.4°±0.2°, 14.2°±0.2°, 19.9°±0.2° and 20.8°±0.2 and wherein preferably the X-ray powder diffraction pattern further comprises peaks at one or more than one or all of 2-theta angles of 21.6°±0.2°, 22.6°±0.2° 22.9°±0.2 and 27.8°±0.2° wherein the X-ray powder diffraction pattern is measured at a temperature in the range of from 15 to 25° C. with Cu-Kα$_{1,2}$ radiation having a wavelength of 0.15419 nm.

55. A compound of formula (IX)

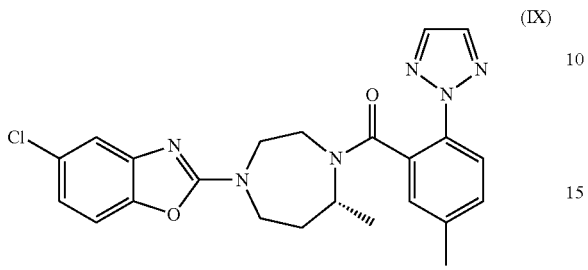

(IX)

obtained or obtainable according to any of embodiments 43 to 51.

56. The compound of embodiment 55, wherein the compound contains less than 5% by weight, more preferably less than 2% by weight, more preferably less than 1% by weight, more preferably less than 100 ppm, of the regio-isomeric side product (IX-S) as impurity

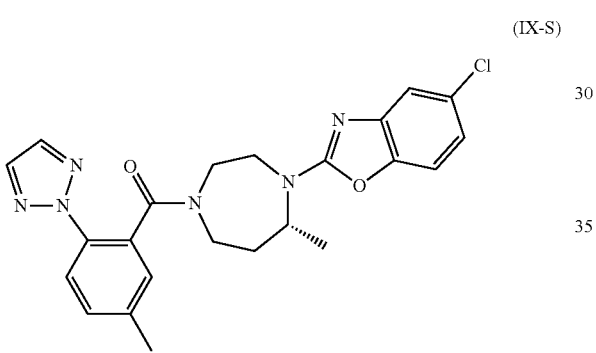

(IX-S)

based on the total weight of the compound (IX), which includes the compound (IX-S).

57. A compound of formula (A)

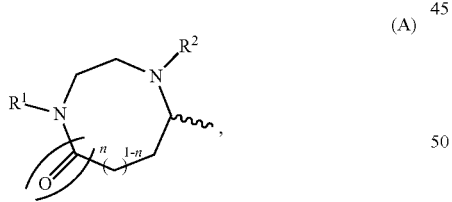

(A)

or a pharmaceutically acceptable salt or solvate thereof, wherein (A) is preferably

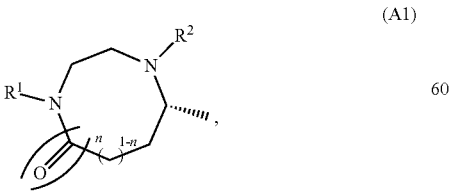

(A1)

wherein $R^1$ is selected from the group consisting of H, $PG^1$ and $R^A$ with $R^A$ being

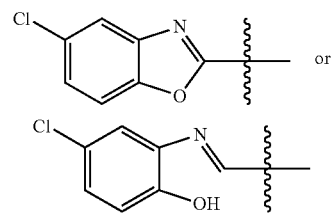

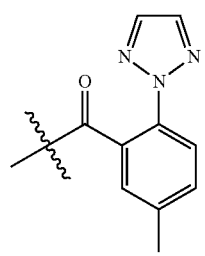 [SMILES: *C(=O)c1cc(C)ccc1-n1nccn1]

and wherein $R^2$ is selected from the group consisting of H, $PG^2$ and $R^B$ with $R^B$ being and wherein $PG^1$ and $PG^2$ are, independently of each other, suitable protecting groups, and wherein n is 0 or 1, and wherein in case n=0 and $R^1$ is $R^A$, $R^2$ is not $R^B$ or H or, wherein in case n=0 and $R^1$ is $R^A$ $R^B$ is $PG^1$ and wherein in case n=0 and $R^1$ is H, $R^2$ is not $R^B$ or, wherein in case n=0 and $R^1$ is H, $R^2$ is H or $PG^2$ and wherein in case n=0 and $R^1$ is Cbz $R^2$ is not H or Boc or $R^B$ and wherein when n=1 $R^1$ and $R^2$ are not both H.

58. A compound of formula (A)

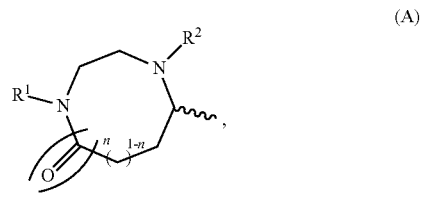

(A)

or a pharmaceutically acceptable salt or solvate thereof, wherein (A) is preferably

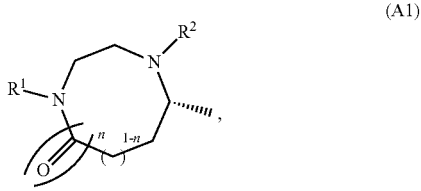

(A1)

wherein n is 1

$R^1$ is selected from the group consisting of H, $PG^1$ and $R^A$ with $R^A$ being

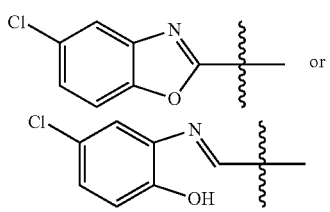

and
R² is selected from the group consisting of H, PG² and R^B with R^B being

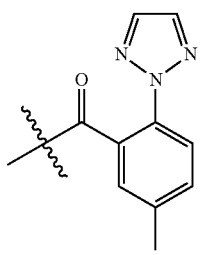 [SMILES: *C(=O)c1cc(C)ccc1-n1nccn1]

and PG¹ and PG² are, independently of each other, suitable protecting groups, and wherein when n=1 R¹ and R² are not both H.
59. The compound of embodiment 58, wherein R¹ is H.
60. The compound of embodiment 59, wherein R² is H.
61. The compound of embodiment 58 or 59, wherein R² is R^B
62. The compound according to any of embodiments 57, 58 or 59 having the structure of formula (VI)

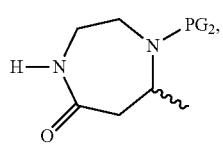

(VI)

wherein PG² is a suitable protecting group, preferably Cbz.
63. The compound of embodiment 58 or 60 wherein R¹ is R^A, wherein R^A is preferably

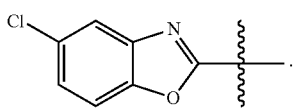

64. The compound according to embodiment 57 or 58, having the structure of formula (VIII)

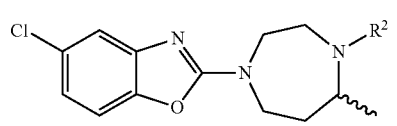

(VIII)

wherein R²H or PG² and PG² is a suitable protecting group.

65. The compound of any of embodiment 58 to 62 having the structure of formula (VI)

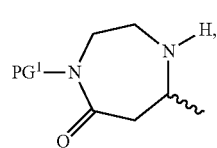

(VI)

wherein PG¹ is a suitable protecting group, preferably Boc.
66. The compound of embodiment 57 or 58 having the structure

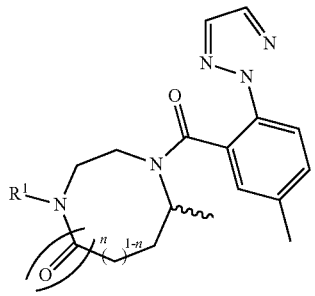

preferably

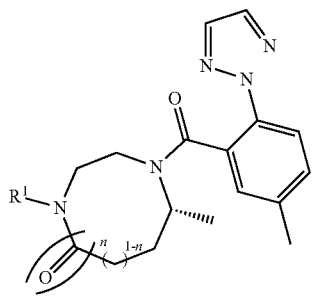

wherein when n=1 R¹ is H or PG¹ and PG¹ is a suitable protecting group, preferably wherein PG¹ is Boc, more preferably wherein R¹ is H and
wherein when n=0 R¹ is PG¹ and PG¹ is a suitable protecting group, preferably wherein PG¹ is Boc.
67. A crystalline form of the compound according to any of embodiments 57 to 66 or a crystalline form of the salt of the compound according to any of embodiments 57 to 66.
68. A crystalline form of the compound of formula (VIIb) or of formula (VIIb*)

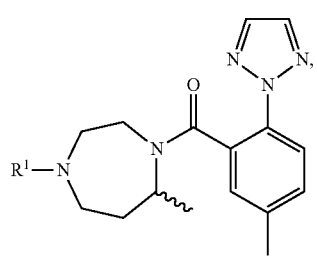

(VIIb)

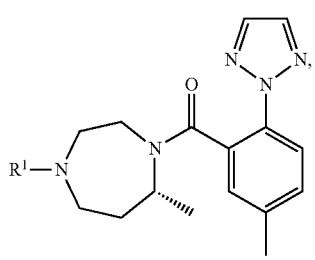

(VIIb*)

or of a salt thereof, wherein R¹ is as defined above, preferably R¹ is H.

69. The crystalline form of embodiment 67 or 68, wherein the salt is selected from the group consisting of hydrochloride salt or (hydrogen) sulphate salt.

70. Crystalline form (A) of the compound of formula

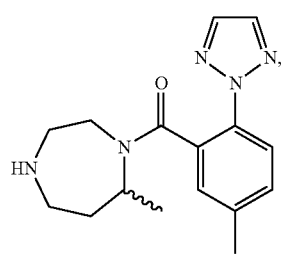

(VIIb-H)

1) which has an X-ray powder diffraction pattern comprising a peak at 2-theta angle of approximately 12.4°±0.2°, preferably has an X-ray powder diffraction pattern comprising peaks at 2-theta angles of approximately 4.8±0.2°, 12.4°±0.2°, 14.2°±0.2°, 19.9°±0.2° and 20.8°±0.2° or at approximately 7.7±0.2°, 11.4°±0.2°, 12.4°±0.2°, 16.2°±0.2° and 18.1°±0.2°, more preferably, at approximately 4.8±0.2°, 12.4°±0.2°, 14.2°±0.2°, 19.9°±0.2° and 20.8°±0.2°, wherein the X-ray powder diffraction pattern is measured at a temperature in the range of from 15 to 25° C. with Cu-Kα$_{1,2}$ radiation having a wavelength of 0.15419 nm or 2) which has an X-ray powder diffraction pattern comprising a peak at 2-theta angle of approximately 12.4°±0.2°, more preferably has an X-ray powder diffraction pattern comprising peaks at 2-theta angles of approximately 4.8±0.2°, 12.4°±0.2°, 14.2°±0.2°, 19.9°±0.2° and 20.8°±0.2 and wherein preferably the X-ray powder diffraction pattern further comprises peaks at one or more than one or all of 2-theta angles of 21.6°±0.2°, 22.6°±0.2° 22.9°±0.2 and 27.8°±0.2° wherein the X-ray powder diffraction pattern is measured at a temperature in the range of from 15 to 25° C. with Cu-Kα$_{1,2}$ radiation having a wavelength of 0.15419 nm.

71. The crystalline form of embodiment 70 2), having an X-ray powder diffraction pattern as disclosed in FIG. 3.

72. Crystalline form (I) of the compound of formula (VIIb*-H)

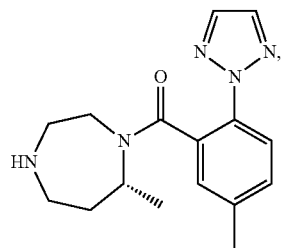

(VIIb*-H)

having an X-ray powder diffraction pattern comprising a peak at 2-theta angle of approximately 11.3°±0.2°, more preferably has an X-ray powder diffraction pattern comprising peaks at 2-theta angles of 11.3±0.2°, 12.3°±0.2°, 13.3°±0.2°, 16.0°±0.2°, 20.00±0.2°, wherein the X-ray powder diffraction pattern is measured at a temperature in the range of from 15 to 25° C. with Cu-Kα$_{1,2}$ radiation having a wavelength of 0.15419 nm.

73. The crystalline form (I) of embodiment 72, wherein an X-ray powder diffraction pattern further comprises peaks at 2-theta angles of 16.5±0.2°, 18.3°±0.2°, 20.1°±0.2°, 22.7°±0.2°.

74. The crystalline form (I) of embodiment 72 or 73, having an X-ray powder diffraction pattern as disclosed in FIG. 4.

75. Sulphate salt of the compound of formula (VIIb) or formula (VIIb*).

76. Crystalline form (I-S) of the sulphate salt of formula (VIIb*-S)

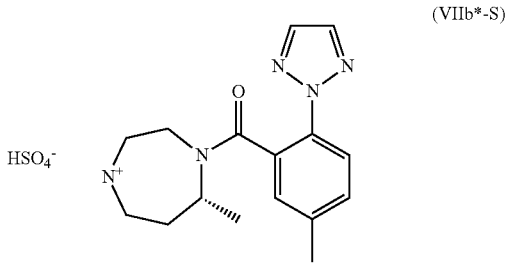 [SMILES: "HSO4-" ; Cc1ccc(-n2nccn2)c(C(=O)N2CC[NH2+]CC[C@H]2C)c1]

(VIIb*-S)

having an X-ray powder diffraction pattern comprising a peak at 2-theta angle of approximately 14.3°±0.2°, more preferably has an X-ray powder diffraction pattern comprising peaks at 2-theta angles of 7.8±0.2°, 8.6°±0.2°, 9.1°±0.2°, 14.3°±0.2, 17.4°±0.2°, 19.7°±0.2°, wherein the X-ray powder diffraction pattern is measured at a temperature in the range of from 15 to 25° C. with Cu-Kα$_{1,2}$ radiation having a wavelength of 0.15419 nm.

77. The crystalline form (I-S) of embodiment 76, wherein the X-ray powder diffraction pattern further comprises peaks at 2-theta angles of 14.7±0.2°, 21.7°±0.2°, 24.0°±0.2°.

78. The crystalline form (I-S) of embodiment 76 or 77, having an X-ray powder diffraction pattern as disclosed in FIG. 5.

79. Hydrochloride salt of the compound of formula (VIIb) or formula (VIIb*).

80. Crystalline form (I-Cl) of the hydrochloride salt of formula (VIIb*-Cl)

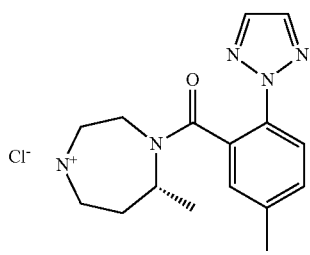

(VIIb*-Cl)

having an X-ray powder diffraction pattern comprising a peak at 2-theta angle of approximately 15.2°±0.2°, more preferably has an X-ray powder diffraction pattern comprising peaks at 2-theta angles of 10.5±0.2°, 11.5°±0.2°, 15.2°±0.2°, 16.6°±0.2, 22.4°±0.2°, wherein the X-ray powder diffraction pattern is measured at a temperature in the range of from 15 to 25° C. with Cu-Kα$_{1,2}$ radiation having a wavelength of 0.15419 nm.

81. The crystalline form (I-Cl) of embodiment 80, wherein an X-ray powder diffraction pattern further comprises peaks at 2-theta angles of 18.5.±0.2°, 23.9°±0.2°.

82. The crystalline form (I-Cl) of embodiment 80 or 81, having an X-ray powder diffraction pattern as disclosed in FIG. 6.

83. A process for preparing crystalline form (A) according to embodiment 70 or 71, or for preparing crystalline form (I) according to any of embodiments 72 to 74 comprising crystallizing the compound of formula (VIIb) or of formula (VIIb*) from a solvent wherein preferably the solvent is selected form the group consisting of ethyl acetate, methanol, CH$_2$Cl$_2$, acetonitrile, isopropyl acetate, acetone, ethanol, isopropanol, toluene, butanol, isobutanol, t-butanol, tetrahydrofuran, methyltetrahydrofuran, cyclohexane and mixture thereof, wherein more preferably the solvent is ethyl acetate.

84. A process for preparing crystalline form (I-S) according to any of embodiments 76 to 78 or for preparing the crystalline form (I-Cl) according to any of embodiments 80 to 82 comprising crystallizing the sulphate salt or the hydrochloride salt of compound of formula (VII*) from a solvent wherein preferably the solvent is selected form the group consisting of ethyl acetate, methanol, CH$_2$Cl$_2$, acetonitrile, isopropyl acetate, acetone, ethanol, isopropanol, toluene, butanol, isobutanol, t-butanol, tetrahydrofuran, methyltetrahydrofuran, cyclohexane and mixture thereof, wherein the solvent is more preferably selected from the group consisting of ethyl acetate, methanol, CH$_2$Cl$_2$ and mixture thereof 85. Use of a compound of formula (A)

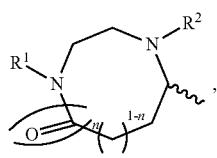

(A)

preferably of formula (A*)

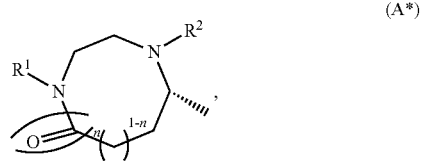

(A*)

or a pharmaceutically acceptable salt or solvate thereof, wherein R$^1$ is selected from the group consisting of H, PG$^1$ and R$^A$ with R$^A$ being

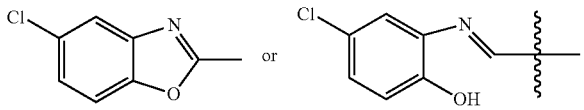

and wherein R$^2$ is selected from the group consisting of H, PG$^2$ and R$^B$ with R$^B$ being

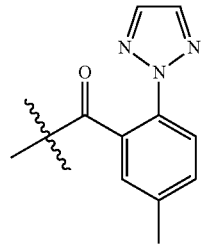 [SMILES: *C(=O)c1cc(C)ccc1-n1nccn1]

and wherein PG$^1$ and PG$^2$ are, independently of each other, suitable protecting groups,
and wherein n in case n=0, at least one of R$^A$ or R$^B$ is H or a protecting group, for the preparation of a compound having the structure of formula (IX)

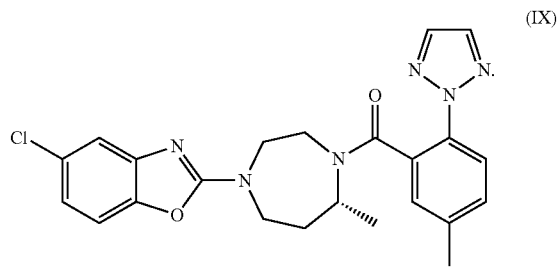 [SMILES: Cc1ccc(-n2nccn2)c(C(=O)N2CCN(c3nc4cc(Cl)ccc4o3)CC[C@H]2C)c1]

(IX)

86. Use of a compound of formula (II)

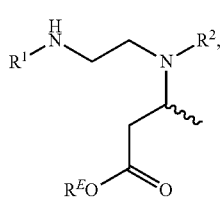

(II)

preferably of formula (II*)

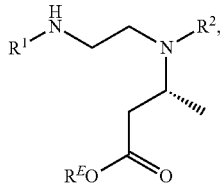

wherein R¹ is selected from the group consisting of H, PG¹ and R^A with R^A being

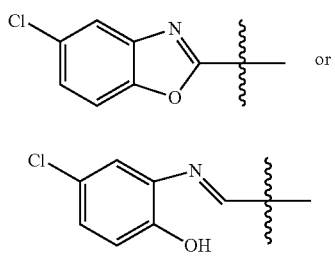

or and wherein R² is selected from the group consisting of H, PG² and R^B with R^B being

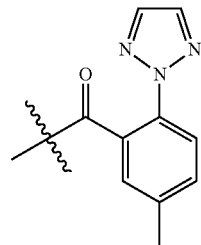

and wherein PG¹ and PG² are, independently of each other, suitable protecting groups
for the preparation of a compound having the structure of formula (IX).

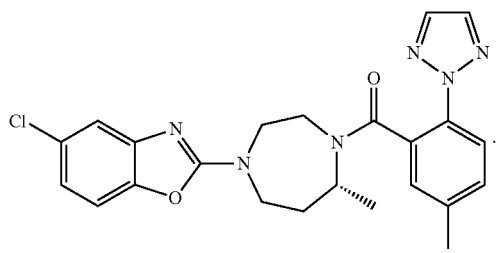

87. Use of the crystalline form (A) according to embodiments 70 or 71 for the preparation of a compound having the structure of formula (IX)

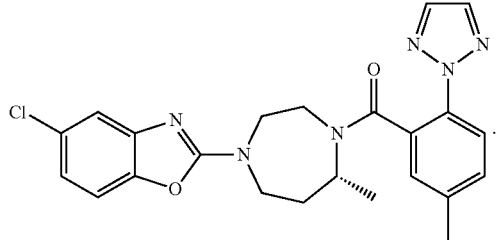

88. Use of the crystalline form (I) according to any of embodiments 72 to 74 for the preparation of a compound having the structure of formula (IX)

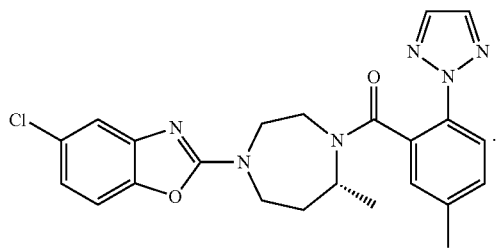

89. Use of the crystalline form (I-S) according to any of embodiments 76 to 78 for the preparation of a compound having the structure of formula (IX)

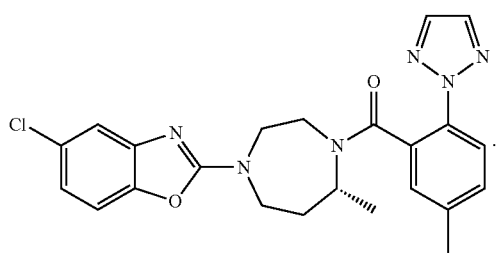

89. Use of the crystalline form (I-Cl) according to any of embodiments 80 to 82 for the preparation of a compound having the structure of formula (IX)

FIGURES

EXAMPLES

Figure 1:
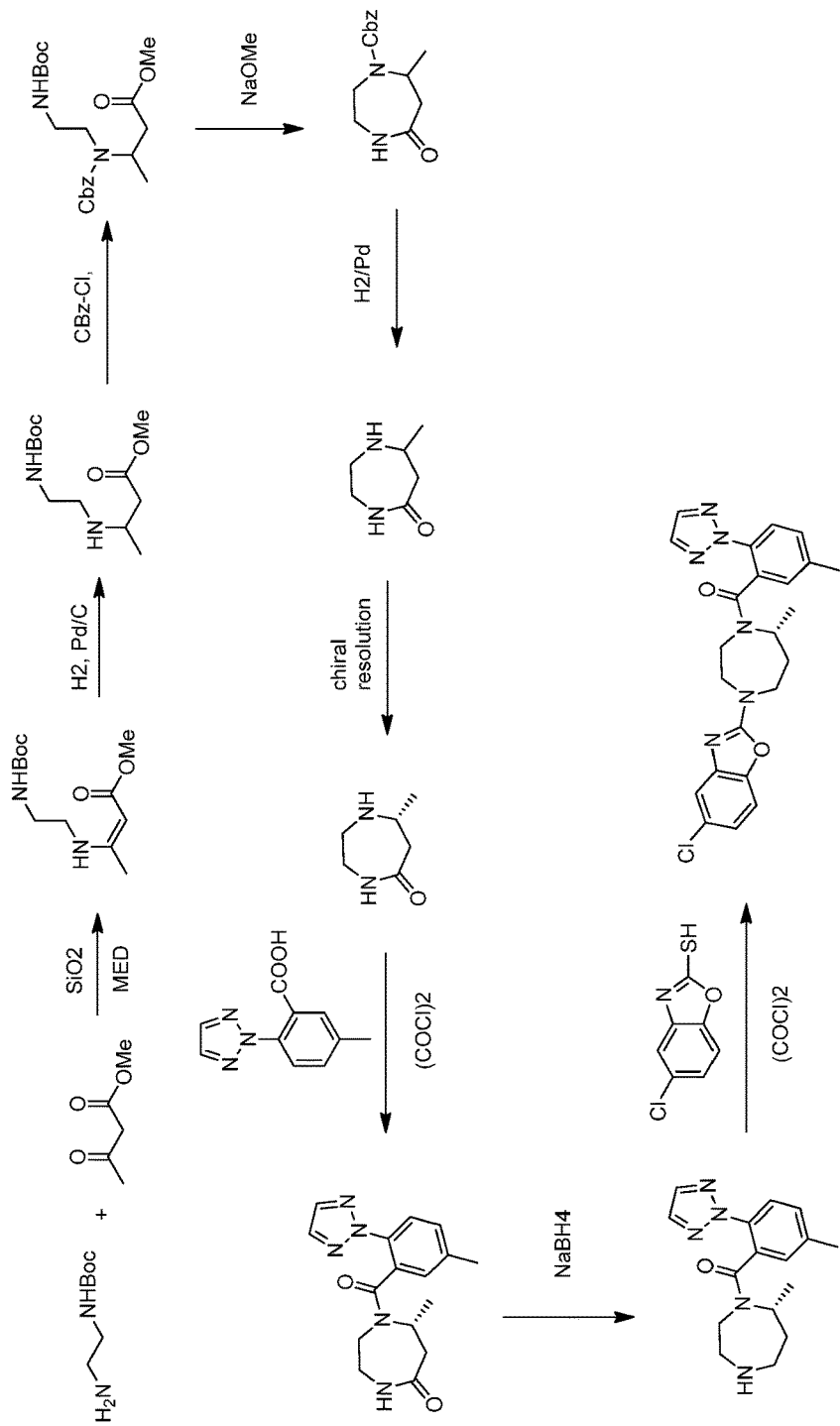
FIGS. 1 and 2 show preferred synthesis schemes according to the invention.
Figure 2:
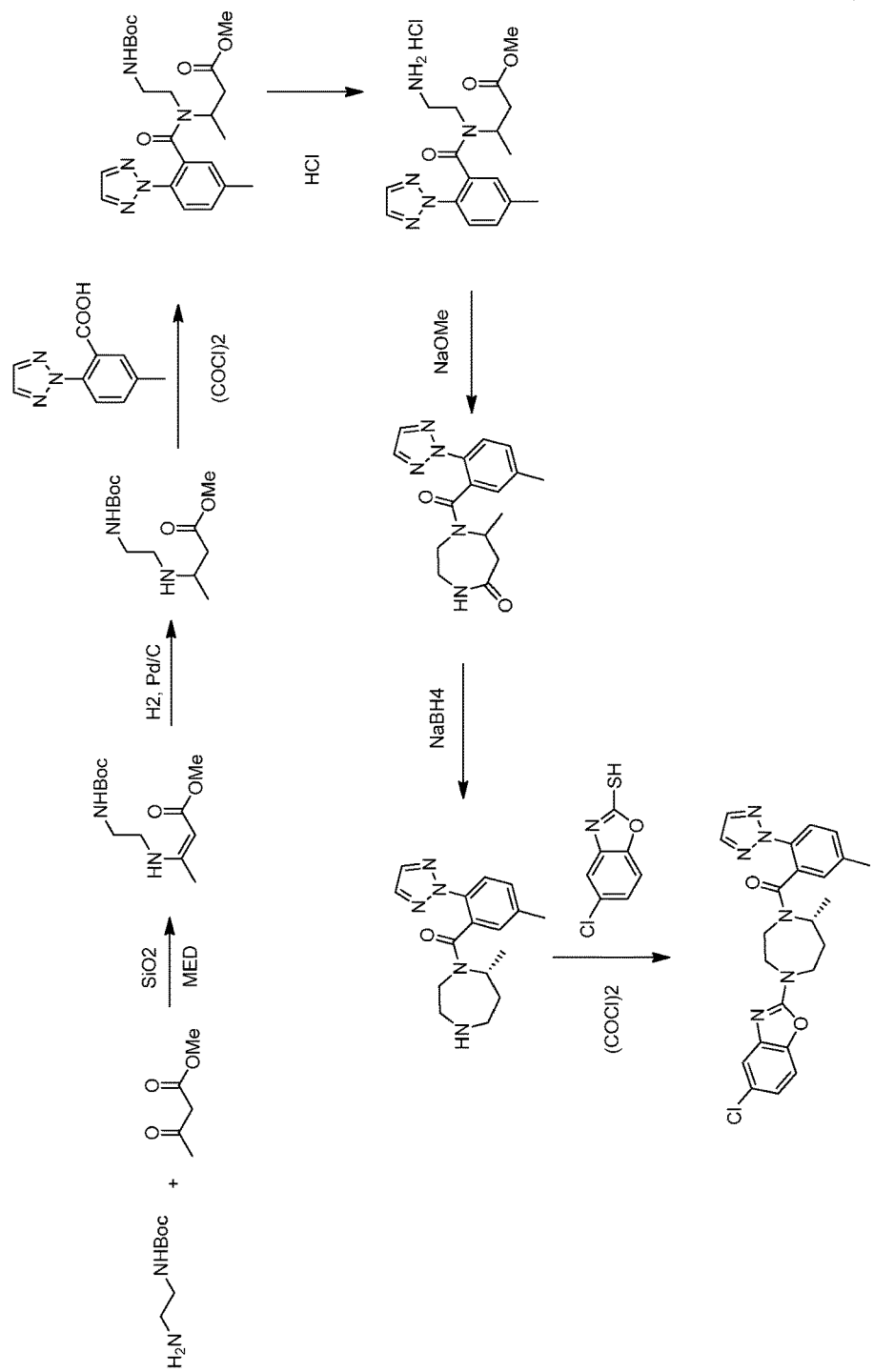

Reference Example 1: X-Ray Powder Diffraction Patterns

X-ray powder diffraction patterns (XRPD) as disclosed herein were obtained with a PANalytical X'Pert PRO diffractometer equipped with a theta/theta coupled goniometer in transmission geometry, Cu-Kα1,2 radiation (wavelength 0.15419 nm) with a focusing mirror and a solid state PIXcel detector. The patterns were recorded at a tube voltage of 45 kV and a tube current of 40 mA, applying a step-size of 0.013° 2-Theta with 40 s per step (255 channels) in the angular range of 2° to 40° 2-Theta at ambient conditions (15 to 25° C.). A typical precision of the 2-theta values is in the range of about ±0.2° 2-Theta. Thus a diffraction peak that appears at 5.0° 2-Theta can appear between 4.8 and 5.2° 2-Theta on most X-ray diffractometers under standard conditions.

Example 1: Preparation of (Z)-Methyl 3-((2-((tert.-Butoxycarbonyl)amino)ethyl)amino)but-2-enoate

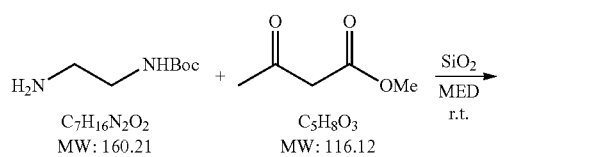

Boc-ethylenediamine (84.3 g, 500 mmol) was dissolved in CH$_2$Cl$_2$ (110 mL), transferred into a 500 mL Schmizo and cooled to 10° C. Silica gel (120 g) was added in portions and the slurry was diluted with CH$_2$Cl$_2$ (50 mL). Methyl acetoacetate (54 mL, 500 mmol) was added, the reaction mixture was stirred at 20° C. and the reaction progress was monitored by GC. The reaction was judged complete after one hour. The silica gel was filtered off and the filter cake was washed with CH$_2$Cl$_2$ (250 mL). The slightly yellow solution was concentrated under reduced pressure to give the enamine as slightly yellow oil (127.9 g).

$^1$H NMR (300 MHz, CDCl$_3$): δ=8.57 (br s, 1H), 4.84 (br s, 1H), 4.47 (s, 1H), 3.61 (s, 3H), 3.33 (m, 2H), 3.23 (m, 2H), 1.91 (s, 3H), 1.43 (s, 9H). $^{13}$C NMR (75 MHz, CDCl$_3$):=170.9, 162.0, 155.9, 82.7, 79.6, 50.0, 42.8, 41.3, 28.3, 19.3. All data are in agreement with the data reported in literature (see *J. Org. Chem.* 2010, 75, 6023).

Example 2

Preparation of Methyl 3-((2-((tert.-butoxycarbonyl)amino)ethyl)amino)butanoate via Hydrogenation

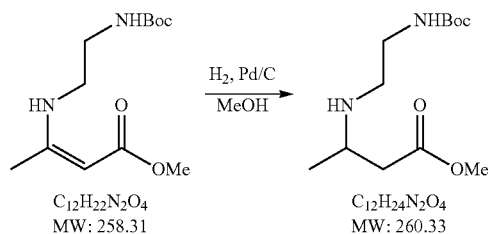 [SMILES: "MeOH" ; COC(=O)/C=C(/C)NCCNC(=O)OC(C)(C)C ; COC(=O)CC(C)NCCNC(=O)OC(C)(C)C]

A solution of the enamine (58.7 g, 227 mmol) in MeOH (650 mL) was hydrogenated in the presence of 73 g Pd/C at 55° C. at a pressure of 3 bar. The reaction was monitored by GC. After complete conversion (approximately 7 hours) the suspension was filtered over a K150 filter and the solid was washed with MeOH. The solution was concentrated under reduced pressure, taken up in MeOH (300 mL) and distilled under reduced pressure to give the β-aminoester (51.6 g, 87%) as oil.

$^1$H NMR (300 MHz, CDCl$_3$): δ=5.28 (br s, 1H, NH), 3.99 (br s, 1H, NH) 3.66 (s, 3H, OCH$_3$), 3.13-3.25 (overlapping m, 3H, CH$_2$+CH), 2.78 (m, 2H, CH$_2$), 2.48 (m, 2H, CH$_2$), 1.41 (s, 9H, C(CH$_3$)$_3$), 1.15 (d, J=6.3 Hz, 3H, CH$_3$). $^{13}$C NMR (75 MHz, CDCl$_3$): δ=172.2, 156.1, 79.2, 51.6, 50.1, 45.9, 40.6, 39.8, 28.3, 19.7.

Example 3

Preparation of Methyl 3-((2-((tert.-butoxycarbonyl)amino)ethyl)amino)butanoate with an Enantiomeric Excess of ee=93% via Asymmetric Hydrogenation

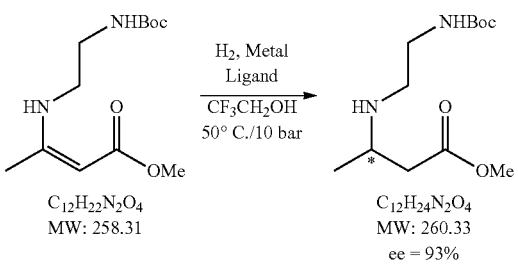

-continued

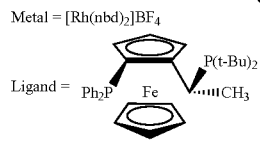

46.2 mg (0.085 mmol) ferrocenyl ligand and 29.0 mg (0.077 mmol) [Rh(nbd)2]BF4 were placed in a 10 mL Schlenk flask that was previously set under an atmosphere of argon. Then 6 mL degassed 2,2,2-trifluoroethanol (TFE) was added and the resulting red solution stirred for 30 min. at 50° C. In a second Schlenk flask, 0.5 g (1.94 mmol) of enamine ((Z)-methyl 3-((2-((tert-butoxycarbonyl)amino)ethyl)amino)but-2-enoate) was placed, followed by 14 mL degassed TFE. The clear solution was stirred for 10 min. Then, both the substrate and the catalyst solution were transferred via syringe into a 50 mL stainless steel reactor that was previously set under an atmosphere of argon. The reactor was sealed, purged with argon in three cycles (1 bar/20 bar) and finally, the argon replaced by hydrogen (4 cycles 1 bar/20 bar). The reactor pressure was set to 10 bar hydrogen, heating to 50° C. and stirring started. After 21 hrs. reaction time, the autoclave was cooled to ambient temperature and the pressure released.

The crude product was analyzed by GC with respect to conversion and chemoselectivity and upon derivatization with 4-chlorobenzoylchloride by chiral HPLC method. The conversion after 21 hrs. was >99.5%, and product 2 (methyl 3-((2-((tert-butoxycarbonyl)amino)ethyl)amino)butanoate) was formed with approx. 60% chemoselectivity and 93% ee (first-eluting enantiomer).

Example 4

Preparation of Methyl 3-((2-((tert.-butoxycarbonyl)amino)ethyl)amino)butanoate via Reduction

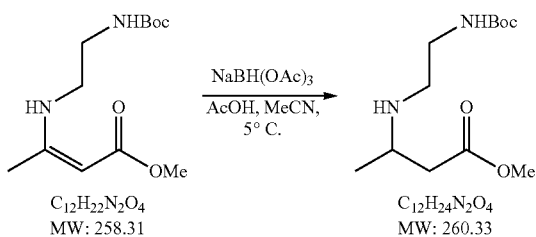 [SMILES: COC(=O)/C=C(/C)NCCNC(=O)OC(C)(C)C ; "AcOH, MeCN,5° C." ; COC(=O)CC(C)NCCNC(=O)OC(C)(C)C ; "NaBH(OAc)3"]

NaBH$_4$ (33.0 g, 872 mmol) was added in small portions over a period of 90 minutes into vigorously stirred acetic acid (500 mL) and the internal temperature was kept between 15-20° C. Vigorous gas formation was observed as well as the formation of a thick suspension halfway through the addition. MeCN (250 mL) was added, the suspension was stirred for 30 minutes and the internal temperature was adjusted to 0-5° C. A solution of the enamine (113.0 g, 437 mmol) in MeCN (150 mL) was added over a period of 45 minutes at 0-5° C. followed by a MeCN-rinse (100 mL). The reaction mixture was stirred for 2.5 hours at 5° C. before being cautiously quenched with H$_2$O (100 mL, gas formation). (At that stage the pH was adjusted to pH=7.0 with NaOH (50%) and CH$_2$Cl$_2$ (100 mL) was added which resulted in the formation of two phases. The two phases were stirred over night: holding point). The pH-value was adjusted to pH=11.5 with NaOH (50%). In order to avoid the formation of solids in the aqueous layer H$_2$O (~800 mL) was added. The organic phase was separated and washed with H$_2$O. The combined aqueous phases were extracted twice with ethyl acetate (250 mL each).

The combined organic phases were dried over Na$_2$SO$_4$, filtered and concentrated to give the filtered and concentrated to give the The analytical data were in full agreement with the data obtained by hydrogenation.

Example 5

Preparation of Methyl 3-((2-((tert.-butoxycarbonyl)amino)ethyl)amino)butanoate with an Enantiomeric Excess of ee=33% Via Chiral Resolution Racemic β-aminoester was resolved with tartaric acid to give enantiomerically enriched β-aminoester.

Example 6

Preparation of 7-Methyl-1,4-diazepan-5-one

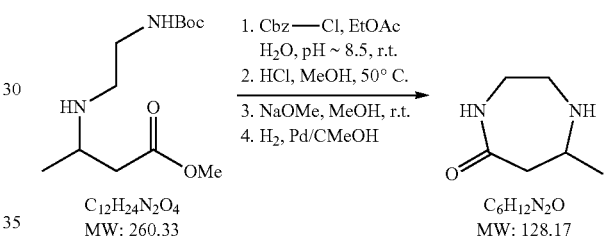

Procedure "Cbz-Protection":

H$_2$O (500 mL) was added to a solution of the β-aminoester (78.0 g, 300 mmol) in EtOAc (1000 mL) at room temperature. Benyzl chloroformate (Cbz-Cl, 51.4 mL, 360 mmol) was added slowly and the pH-value was kept between pH=8-9 by the addition of NaOH (10 M). The reaction was slightly exotherm and GC indicated complete conversion of the starting material after 30 minutes. The two phases were separated and the organic phase was washed with a saturated NaHCO$_3$ solution (300 mL). The solution was concentrated under reduced pressure to give the Cbz-protected amine quantitatively (128.4 g) as oil. The crude product was used in the next step without any further purification.

$^1$H NMR (300 MHz, CDCl$_3$): δ=7.33-7.39 (m, 6H, H$_{arom}$+NH), 5.13 (s, 2H, OCH$_2$), 4.32 (br s, 1H, CH), 3.61 (s, 3H, OCH$_3$), 3.21-3.35 (br m, 4H, CH$_2$, CH$_2$), 2.42-2.80 (series of br m, 2H, CH$_2$), 1.43 (s, 9H, C(CH$_3$)$_3$), 1.26 (br s, 3H, CH$_3$).

Procedure "Boc-Deprotection":

HCl (37 w %, 45 mL, 540 mmol) was added to a stirred solution of the Boc-protected amine (128.4 g, calcd. as 270 mmol) in MeOH (1200 mL) and the reaction mixture was stirred at 50° C. for two hours and at 80° C. for one hour. The reaction progress was monitored by HPLC and the reaction was judged complete after 4 hours. The reaction mixture was concentrated to a volume of approximately 250 mL. A solid precipitated during the MeOH-destillation. Acetone (1000 mL) was added dropwise and the solvent was removed completely. CH$_2$Cl$_2$ (300 mL) was added and then removed by distillation. The product (amine in form of HCl salt, 116.7 g) was obtained as foam and used in the next step without any further purification.

Procedure "Cyclization":

NaOMe (51.2 g, 972 mmol) was added to a stirred solution of the amine. HCl salt (116.2 g, calculated as 243 mmol) im MeOH (1000 mL) at room temperature. An exotherm reaction was observed. The reaction mixture was stirred over night at room temperature. The solids were filtered off over a K150 filter and washed with MeOH (100 mL). The solution of the crude product was used directly in the next step without further purification.

A small aliquot was used for characterization. $^1$H NMR (300 MHz, CDCl$_3$): δ=7.36 (m, 5H, H$_{arom.}$), 5.15 (s, 2H, OCH$_2$), 4.74 (br m, 2H, NH, CH), 4.25 (br s, 1H, CH$_A$), 3.34 (m, 1H, CH$_X$), 3.15 (m, 2H, CH$_B$, CH$_Y$), 2.81 (d, J=14.5 Hz, 1H, CH$_P$), 2.50 (dd, J=14.5, 5.9 Hz, 1H, CH$_Q$), 1.26 (d, J=7.0 Hz, 3H, CH$_3$).

Procedure "Cbz-Deprotection":

The above mentioned solution of the Cbz-protected amine (calcd. as 219 mmol) in MeOH (1100 mL) was concentrated to a volume of approximately 700 mL. This solution was hydrogenated in the presence of Pd/C (46 g, 10% Pd) at room temperature at a H$_2$-pressure of 2 bar. The hydrogenation was monitored by HPLC and judged complete after two hours. The suspension was filtered over a K150 filter and the filter cake was washed with MeOH. The solution of the crude product was concentrated under reduced pressure and the residue (71.4 g) was taken up in CH$_2$Cl$_2$ (200 mL). The solution was stirred for 30 minutes and the remaining solids were filtered off. The solution was concentrated and the residue (30 g) started crystallizing upon standing at room temperature. MTBE (200 mL) was added and the suspension was stirred for one hour. The solid was filtered off, washed with MTBE and dried over night at 40° C./2 mbar to give 7-methyl-1,4-diazepan-5-one (17.4 g, 62%) as colorless crystals.

$^1$H NMR (300 MHz, CDCl$_3$): δ=7.31 (br s, 1H, C(O)NH), 3.28 (m, 1H, CH$_A$), 2.90-3.14 (series of overlapping m, 3H, CH, CH$_B$, CH$_X$), 2.77 (m, 1H, CH$_Y$), 2.51 (dd, J=14.1, 9.6 Hz, 1H, CH$_P$), 2.35 (apparent d, J=14.3 Hz, 1H, CH$_Q$), 2.03 (br s, 1H, NH), 1.09 (d, J=6.5 Hz, 3H, CH$_3$). $^{13}$C NMR (75 MHz, CDCl$_3$): δ=177.3, 49.4, 47.2, 44.4, 23.6.

Example 7

Chiral Resolution of 7-Methyl-1,4-diazepan-5-one

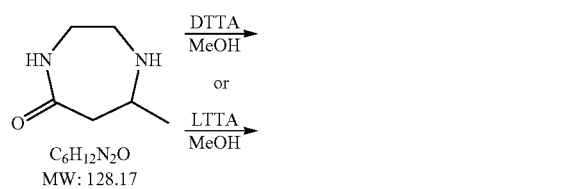

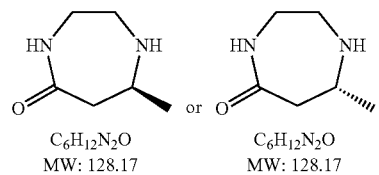

Chiral resolutions were achieved with several chiral acids with varying degree of induction by performing a systematic screening. Here, the best hit will be described as a representative example. DTTA corresponds to (−)-Di-O,O'-toluyl-D-tartaric acid and LTTA corresponds to the enantiomer (+)-Di-O,O'-toluyl-L-tartaric acid. A solution of the chiral acid (62.8 mg, 0.16 mmol) in MeOH (0.5 mL) and a solution of racemic 7-methyl-1,4-diazepan-5-one (41.4 mg, 0.32 mmol) in MeOH (0.8 mL) were combined and allowed to crystallize over night. The solid was filtered and the enantiomeric excess was determined by HPLC. The enantiomeric ratio was >40:1 in both cases, the absolute stereochemistry is determined according to literature proceedings.

Example 8

Reaction of Methyl 3-((2-((tert.-butoxycarbonyl)amino)ethyl)amino)butanoate and 5-Methyl-2-(2H-1,2,3-triazol-2-yl)benzoic Acid

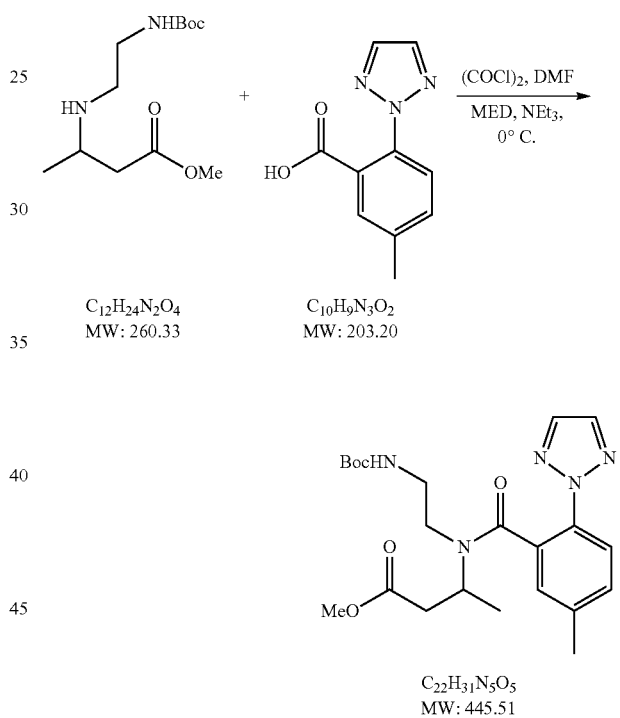

Oxalyl chloride (14.26 g, 118.1 mmol) was added over a period of 14 minutes to a stirred suspension of 5-Methyl-2-(2H-1,2,3-triazol-2-yl)benzoic Acid (20.0 g, 98.4 mmol) in CH$_2$Cl$_2$ (132 mL) and DMF (2.0 mL) at 1° C. After complete addition the reaction mixture was stirred for 30 minutes at 5° C. An addition funnel was charged with a solution of 3-((2-((tert.-butoxycarbonyl)amino)ethyl)amino)butanoate (24.4 g, 93.7 mmol) in CH$_2$Cl$_2$ (340 mL) and NEt$_3$ (19.0 g, 187.4 mmol). The amine solution was added over a period of 40 minutes to the stirred acid chloride solution at a rate to keep the internal temperature <10° C. The reaction progress was monitored by HPLC and the reaction was judged complete after two hours. The reaction was quenched with H$_2$O (250 mL) and the pH-value was adjusted to pH=10.0 by the addition of NaOH (2.0 M). The organic layer was separated and washed with H₂O (250 mL) at a pH=2.0 adjusted with HCl (2.0 M). The organic phase was concentrated under reduced pressure. The residue was taken up in toluene (100 mL) and concentrated under reduced pressure to give 49.6 g residue. The residue was taken up in cyclohexane (~250 mL) and stirred for two hours at room temperature. The solid was filtered, washed twice with cyclohexane (2×20 mL) and dried (40° C., <5 mbar) to give the product (35.4 g, 84% yield) as a crystalline solid.

¹H NMR (300 MHz, DMSO-D₆): δ=6.77-8.07 (series of overlapping m, 6H), 3.88-4.37 (series of overlapping m, 1H), 3.42-3.66 (three s, 3H), 2.56-3.35 (series of overlapping m, 6H), 2.39 (three s, 3H), 0.82-1.40 (series of overlapping m, 12H).

Example 9

Preparation of Methyl 3-(N-(2-aminoethyl)-5-methyl-2-(2H-1,2,3-triazol-2-yl)benzamido)butanoate Hydrochloride by Boc-Cleavage

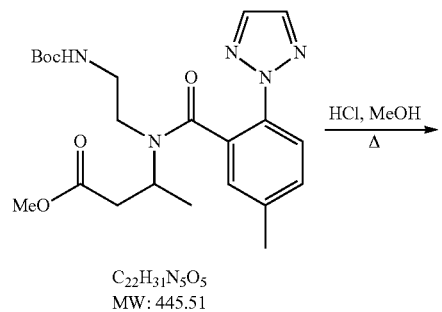

C₂₂H₃₁N₅O₅
MW: 445.51

HCl, MeOH
Δ

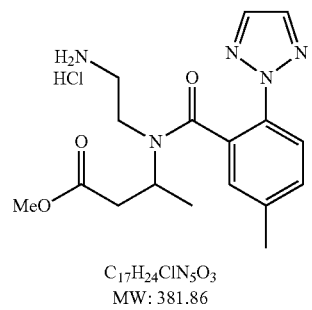

C₁₇H₂₄ClN₅O₃
MW: 381.86

HCl (1.25 M in MeOH, 136.3 mmol) was added to a solution of the Boc-protected amine (30.4 g, 68.2 mmol) in MeOH (304 mL) and the reaction mixture was refluxed. The reaction progress was monitored by HPLC and judged complete after 5.5 hours. The reaction mixture was cooled to room temperature and concentrated under reduced pressure. The residue was taken up in toluene (100 mL) and concentrated under reduced pressure to give 30.5 g foam. Crystallization from toluene and cyclohexane gave Methyl 3-(N-(2-aminoethyl)-5-methyl-2-(2H-1,2,3-triazol-2-yl)benzamido)butanoate Hydrochloride (25.1 g, 97%) as a crystalline solid.

¹H NMR (300 MHz, D₂O): δ=7.14-7.93 (series of overlapping m, 5H), 2.88-4.41 (series of overlapping m, 8H), 2.05-2.77 (series of overlapping m, 5H), 1.10-1.33 (series of d, 3H).

Example 10

Preparation of 7-Methyl-1-(5-methyl-2-(2H-1,2,3-triazol-2-yl)benzoyl)-1,4-diazepan-5-one Via Cyclization of Methyl 3-(N-(2-aminoethyl)-5-methyl-2-(2H-1,2,3-triazol-2-yl)benzamido)butanoate Hydrochloride

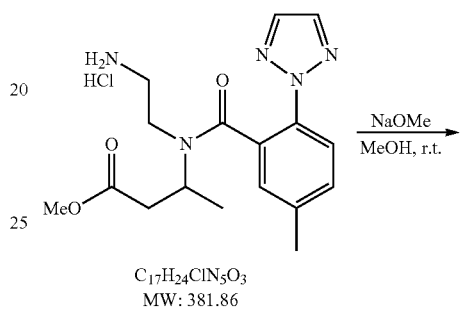

C₁₇H₂₄ClN₅O₃
MW: 381.86

NaOMe
MeOH, r.t.

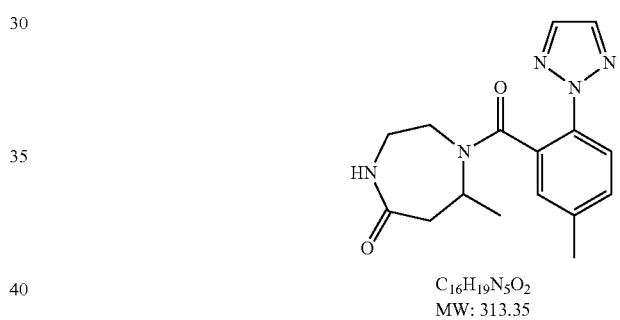

C₁₆H₁₉N₅O₂
MW: 313.35

NaOMe (6.0 g, 115.3 mmol) was added to a solution of Methyl 3-(N-(2-aminoethyl)-5-methyl-2-(2H-1,2,3-triazol-2-yl)benzamido)butanoate Hydrochloride (29.34 g, 76.8 mmol) in MeOH (380 mL) at room temperature and the reaction progress was monitored by HPLC. The reaction was judged complete after 1.5 hours. The suspension was diluted with CH₂Cl₂ (380 mL) and H₂O (380 mL) and the organic layer was separated. The aqueous layer was extracted twice with CH₂Cl₂ (2×200 mL) and the combined organic phases were concentrated under reduced pressure to give a residue that was taken up in cyclohexane (100 mL), filtered and dried to give 7-Methyl-1-(5-methyl-2-(2H-1,2,3-triazol-2-yl)benzoyl)-1,4-diazepan-5-one (17.6 g, 85% yield) as a crystalline solid. A second crystallization from the mother liquor gave additional 7-Methyl-1-(5-methyl-2-(2H-1,2,3-triazol-2-yl)benzoyl)-1,4-diazepan-5-one (1.7 g).

¹H NMR (300 MHz, CDCl₃, suspension): δ=7.76-7.90 (m, 3H), 6.94-7.36 (series of m, 3H), 5.35 (m, ~0.5H), 4.89 (m, ~0.5H), 3.95-4.09 (series of m, ~0.5H), 3.21-3.64 (series of overlapping m, 2H), 2.72-3.15 (series of overlapping m, ~2.5H), 2.16-2.64 (series of m+s, 4H), 0.92-1.36 (series of d, 3H).

Example 11

Preparation of 7-Methyl-1-(5-methyl-2-(2H-1,2,3-triazol-2-yl)benzoyl)-1,4-diazepan-5-one Via Reaction of 7-Methyl-1,4-diazepan-5-one and 5-Methyl-2-(2H-1,2,3-triazol-2-yl)benzoic Acid

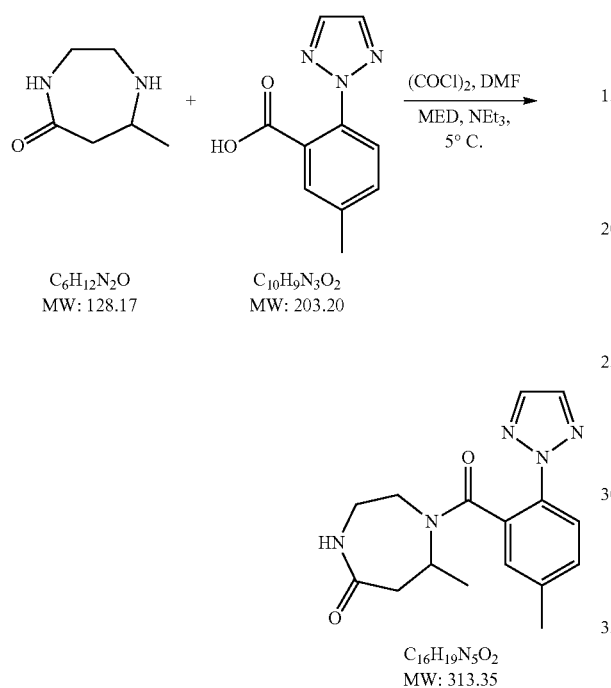

A solution of oxalyl chloride (1.08 mL, 12.6 mmol) in CH$_2$Cl$_2$ (2 mL) was added over a period of 15 minutes to a suspension of 5-Methyl-2-(2H-1,2,3-triazol-2-yl)benzoic Acid (2.13 g, 10.5 mmol) in CH$_2$Cl$_2$ (14 mL) and DMF (0.22 mL) at 0-2° C. The resulting clear solution was stirred for 30 minutes at 5° C. An addition funnel was charged with a solution of 7-Methyl-1,4-diazepan-5-one (1.34 g, 10.0 mmol) in CH$_2$Cl$_2$ (11 mL) and NEt$_3$ (2.9 mL, 21 mmol) and the solution was added over a period of 20 minutes. The reaction mixture was stirred for one hour at 5° C. and the reaction progress was monitored by HPLC. The reaction was quenched by the slow addition of H$_2$O (27 mL) and the two phases were stirred for 15 minutes. The phases were separated and the organic layer was dried over MgSO$_4$, filtered and concentrated under reduced pressure to give 3.3 g of a foam. The crude product was taken up in MeOH (7.5 mL) and the product was allowed to crystallize over night. The solid was filtered off, washed with MeOH and dried over night (40° C., 2 mbar) to give 2.5 g (80% yield) 7-Methyl-1-(5-methyl-2-(2H-1,2,3-triazol-2-yl)benzoyl)-1,4-diazepan-5-one as a crystalline solid.

$^1$H NMR (300 MHz, CDCl$_3$): δ=7.77-7.91 (m, 3H), 6.85-7.37 (series of m, 3H), 5.36 (m, ~0.5H), 4.90 (m, ~0.5H), 3.93-4.13 (series of m, ~0.5H), 3.21-3.64 (series of overlapping m, 2H, 2.16-3.16 (series of overlapping m, ~6.5H), 0.92-1.37 (series of d, 3H). The analytical data are in full agreement with the data obtained via the other variant 1.

Example 12

Preparation of (7-Methyl-1,4-diazepan-1-yl)(5-methyl-2-(2H-1,2,3-triazol-2-yl)phenyl)methanone Via Reduction of 7-Methyl-1-(5-methyl-2-(2H-1,2,3-triazol-2-yl)benzoyl)-1,4-diazepan-5-one

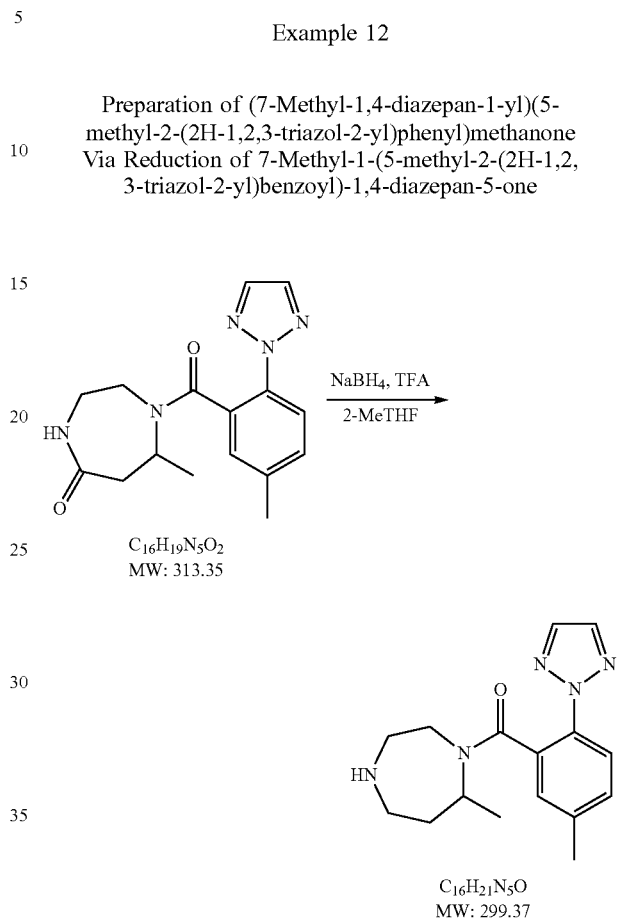

7-Methyl-1-(5-methyl-2-(2H-1,2,3-triazol-2-yl)benzoyl)-1,4-diazepan-5-one (5.0 g, 15.9 mmol) was added to a suspension of NaBH$_4$ (6.03 g, 159.9 mmol) in 2-MeTHF (100 mL) and the suspension was warmed to 45° C. TFA (24.6 mL, 318 mmol) was added via syringe pump over a period of 16 hours at 55° C. (In this case the reaction did not go to completion. Additional NaBH$_4$ and TFA had to be added). The reaction progress was monitored by HPLC and after complete conversion the reaction mixture was cooled to room temperature. The reaction was quenched by the addition of brine (500 mL). The organic phase was separated, washed with H$_2$O (200 mL) and dried over MgSO$_4$. The drying agent was filtered and the solution was concentrated to give (7-Methyl-1,4-diazepan-1-yl)(5-methyl-2-(2H-1,2,3-triazol-2-yl)phenyl)methanone (5.59 g) as a white solid.

The crude product was taken up in a mixture (25 mL) of heptane/ethyl acetate/NEt$_3$ (1/1.5/0.1) and the solid was filtered to give (7-Methyl-1,4-diazepan-1-yl)(5-methyl-2-(2H-1,2,3-triazol-2-yl)phenyl)methanone (3.30 g, 69%) as a crystalline solid.

Figure 3:
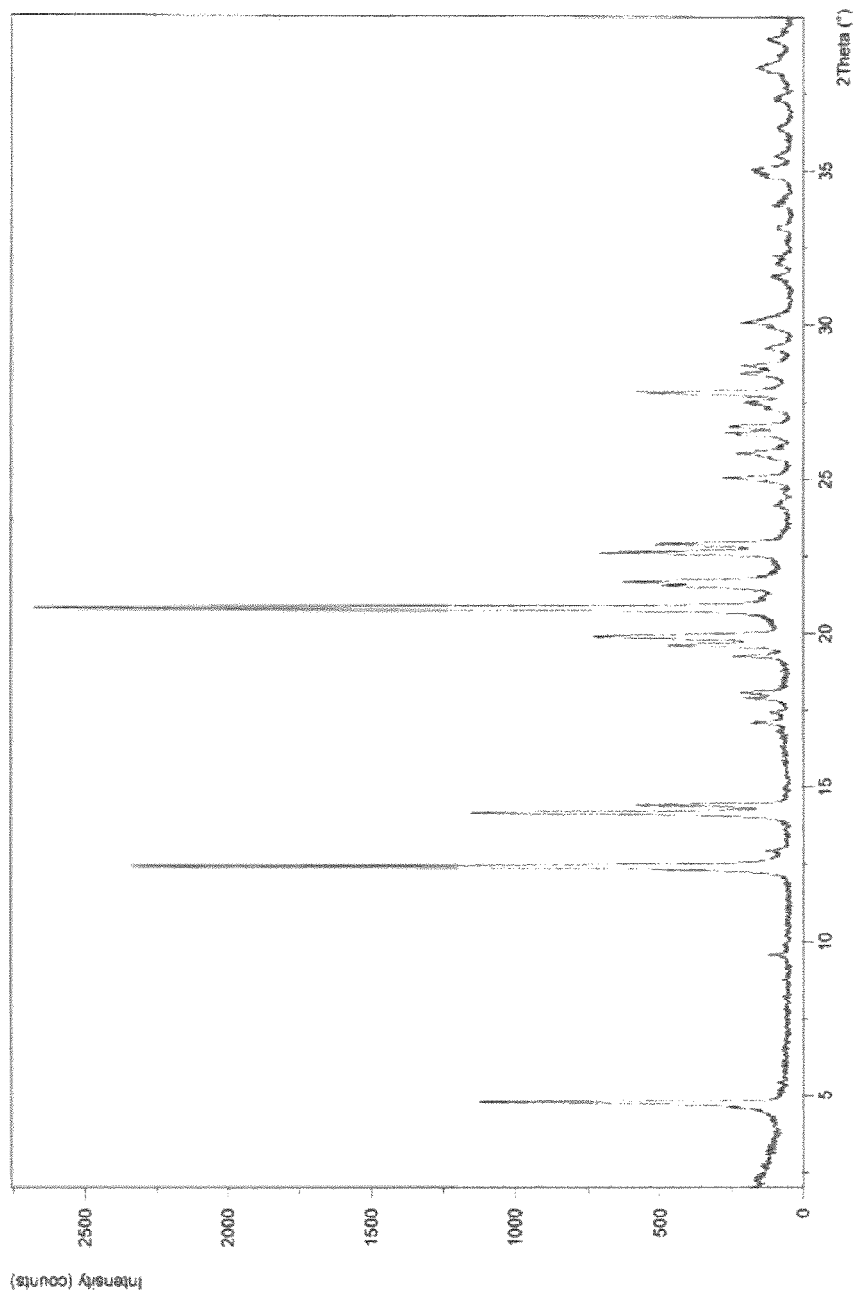
FIG. 3 shows a representative X-ray powder diffraction (XRPD) pattern of the crystalline form of compound (VIIb) according to the present invention, as determined according to Reference Example 1.

The XRPD analysis of the crystalline compound of the title gave the XRPD of FIG. 3

Example 13

Preparation of R-(7-Methyl-1,4-diazepan-1-yl)(5-methyl-2-(2H-1,2,3-triazol-2-yl)phenyl)methanone Via Reduction of 7-Methyl-1-(5-methyl-2-(2H-1,2,3-triazol-2-yl)benzoyl)-1,4-diazepan-5-one

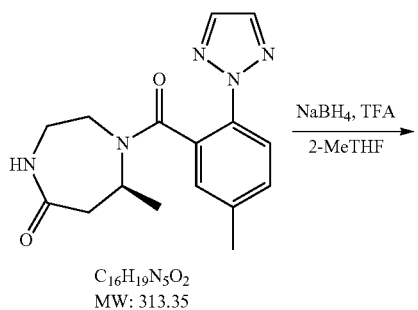

C$_{16}$H$_{19}$N$_5$O$_2$
MW: 313.35

C$_{16}$H$_{21}$N$_5$O
MW: 299.37

40 g of R-7-Methyl-1-(5-methyl-2-(2H-1,2,3-triazol-2-yl)benzoyl)-1,4-diazepan-5-one (5.0 g, 15.9 mmol) was reduced with the same procedure of the above example 12. After extraction 63.6 g of crude reduced compound were obtained. The yield was based on the crude product was >100%.

The crude product was taken up in EtOAc and the solid was filtered to give R-(7-Methyl-1,4-diazepan-1-yl)(5-methyl-2-(2H-1,2,3-triazol-2-yl)phenyl)methanone as a crystalline solid (2.4 mg) in a yield of 6% (assayed by HPLC).

The mother liquor was then washed and distilled off to give 33.5 g of crude reduced compound.

Example 14

Preparation of Hydrochloride Salt of R-(7-Methyl-1,4-diazepan-1-yl)(5-methyl-2-(2H-1,2,3-triazol-2-yl)phenyl)methanone The 33.5 g of R-(7-Methyl-1,4-diazepan-1-yl)(5-methyl-2-(2H-1,2,3-triazol-2-yl)phenyl)methanone recovered from the mother liquor were dissolved in methanolic HCl and the solvent was removed. The formed HCl salt was crystallized from EtOAc and isolated to give 18.2 g of hydrochloride salt (42% yield, assay by HPLC: 98.4%).

Figure 4:
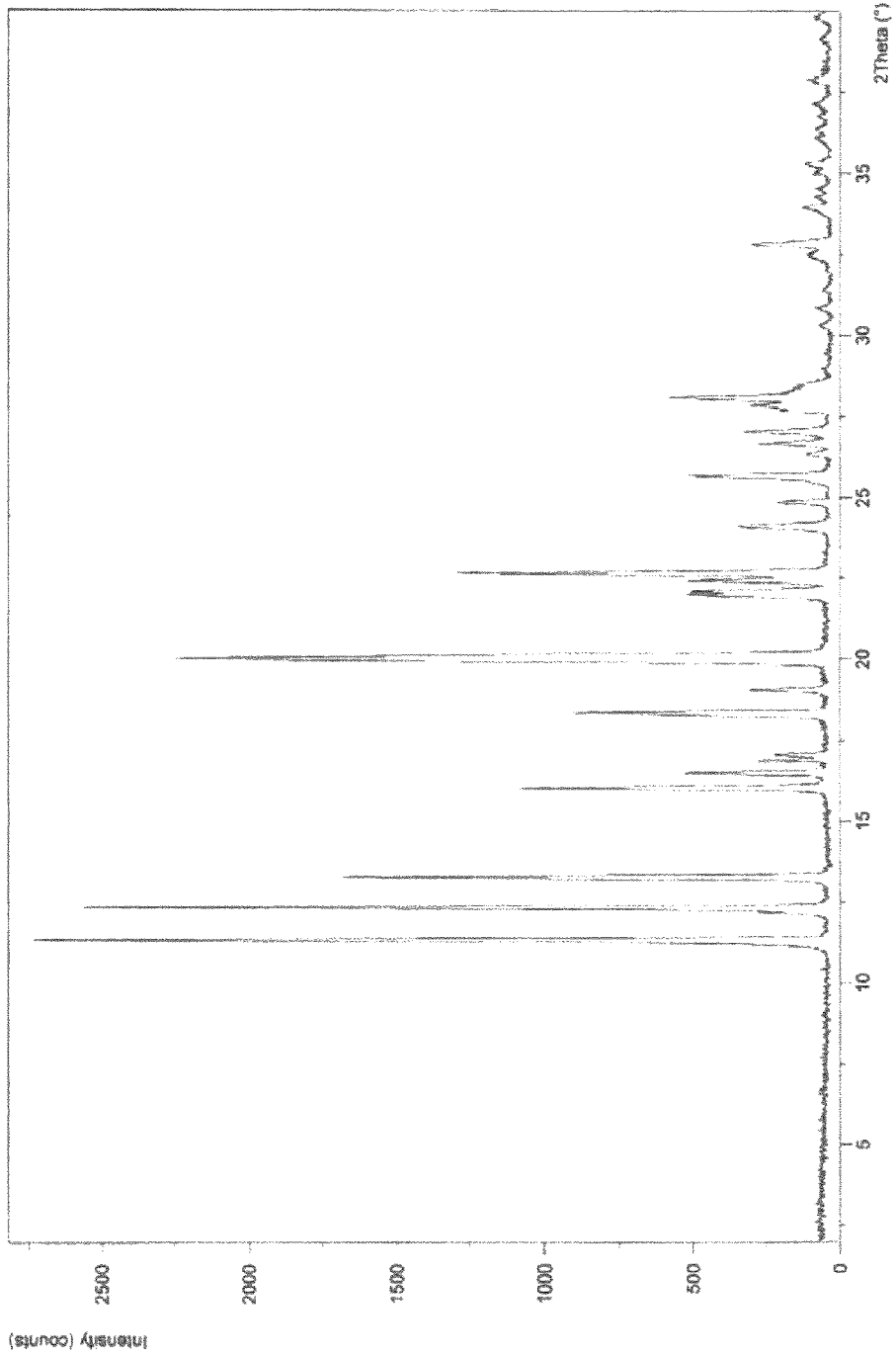
FIG. 4 shows a representative X-ray powder diffraction (XRPD) pattern of the crystalline form (I) of compound (VIIb*) according to the present invention, as determined according to Reference Example 1.

The XRPD analysis of the crystalline compound of the title gave the XRPD of FIG. 4.

Example 15

Preparation of Sulfate Salt of R-(7-Methyl-1,4-diazepan-1-yl)(5-methyl-2-(2H-1,2,3-triazol-2-yl)phenyl)methanone Crystalline Form (VIIb*-S)

To a stirred solution of R-(7-Methyl-1-(5-methyl-2-(2H-1,2,3-triazol-2-yl)benzoyl)-1,4-diazepan-5-one) (100 mg, 0.33 mmol, free amine, as is) in 3 mL MeOH and 3 mL CH$_2$Cl$_2$ was added H$_2$SO$_4$ (10 µL, 0.18 mmol). The solvent was removed under reduced pressure to give the compound of the title as a crystalline residue (73 mg, as is).

Figure 5:
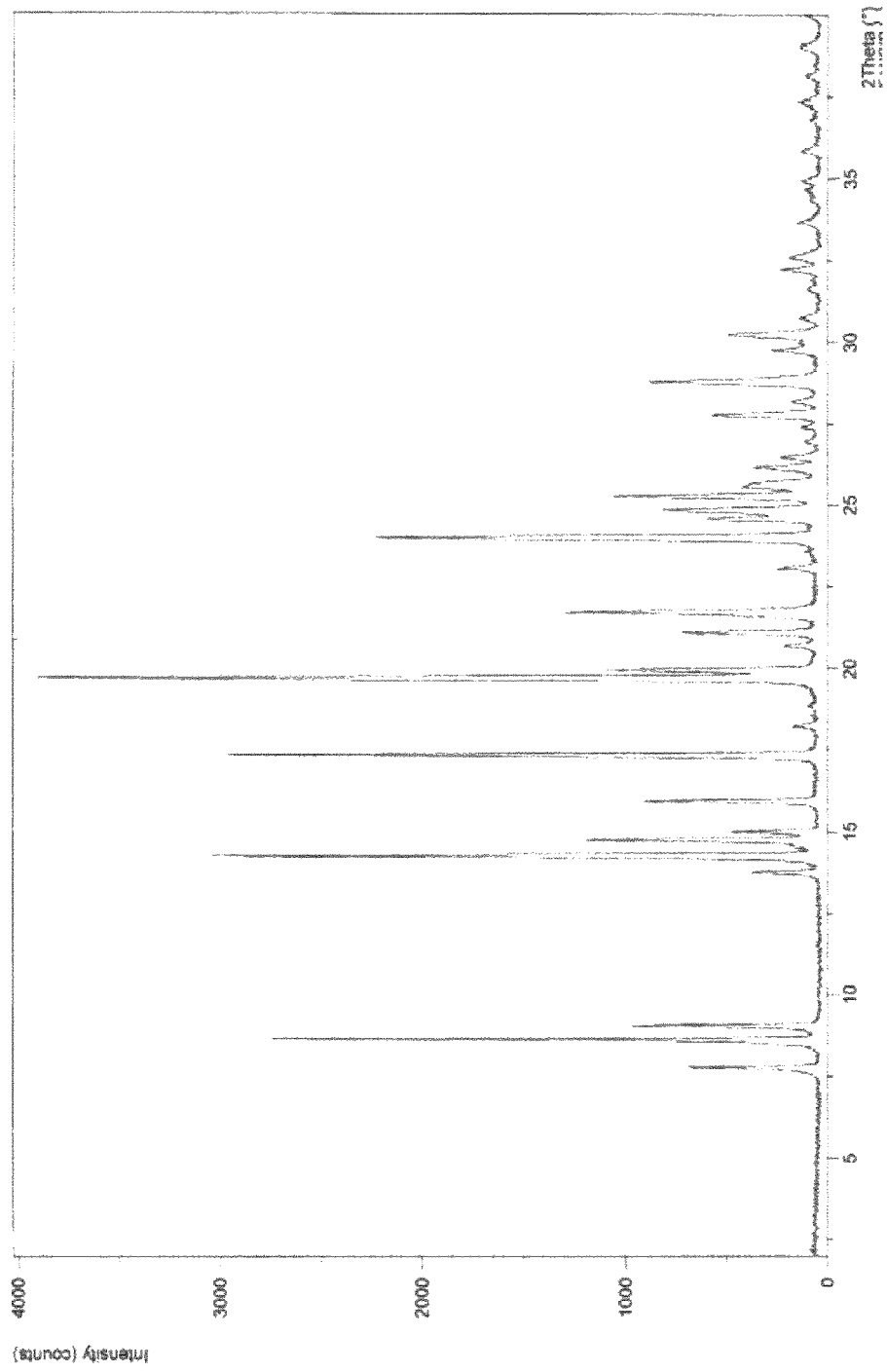
FIG. 5 shows a representative X-ray powder diffraction (XRPD) pattern of the crystalline form (I-S) of the sulphate salt of compound (VIIb*) according to the present invention, as determined according to Reference Example 1.
Figure 6:
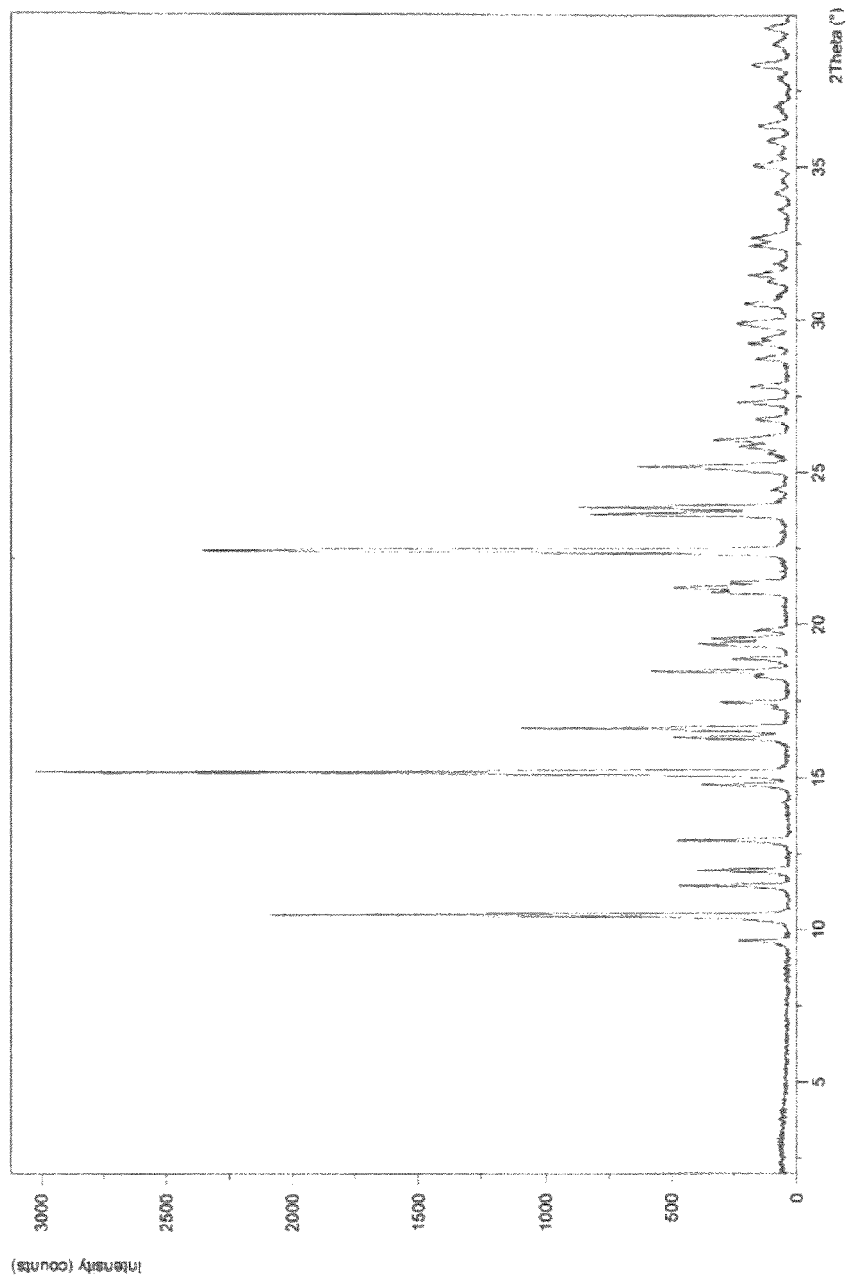
FIG. 6 shows a representative X-ray powder diffraction (XRPD) pattern of the crystalline form (I-Cl) of the hydrochloride salt of compound (VIIb*) according to the present invention, as determined according to Reference Example 1.
Figure 7:
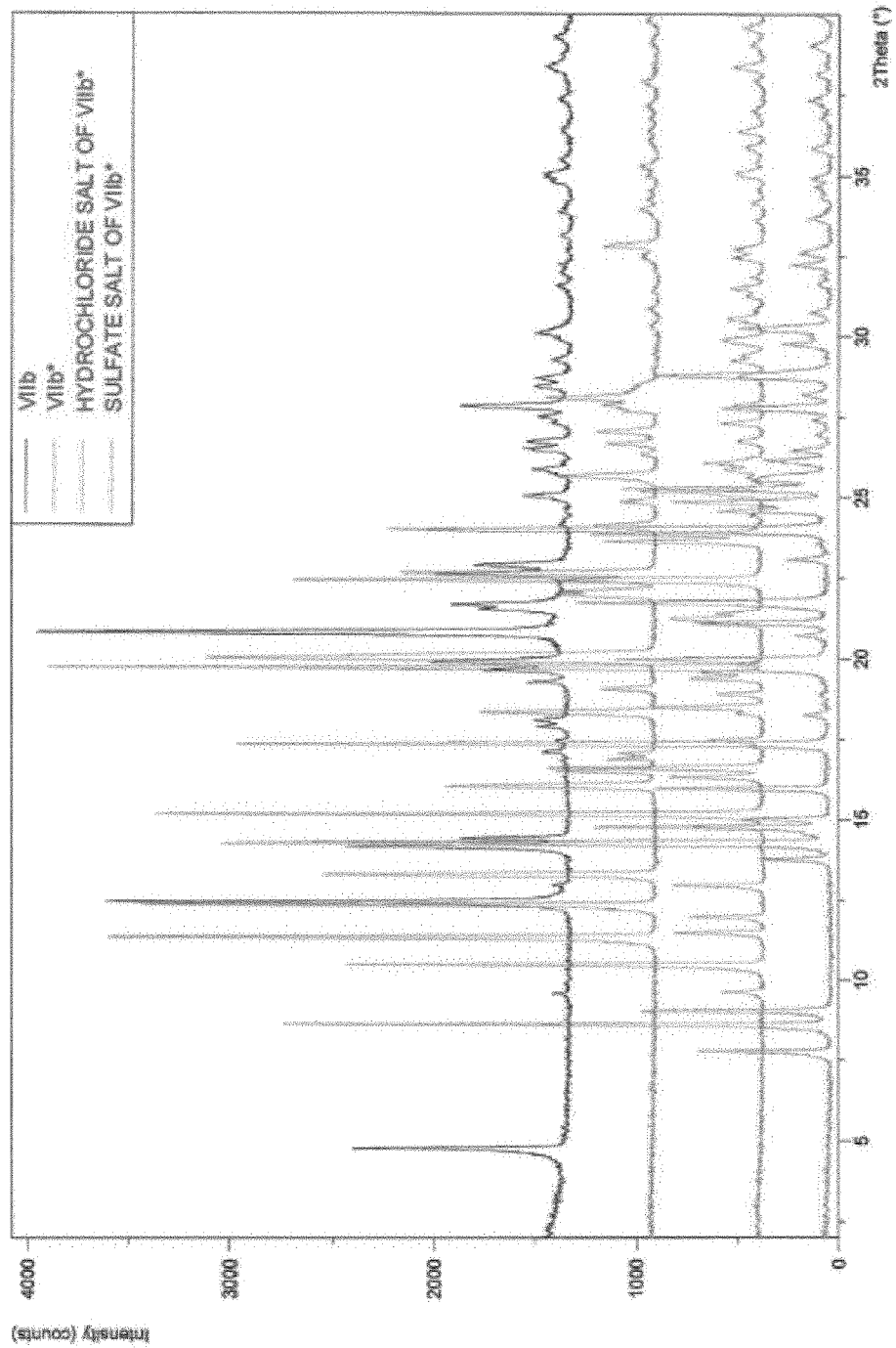
FIG. 7 shows the representative X-ray powder diffraction (XRPD) pattern of FIGS. 3, 4, 5 and 6 for comparison.

The XRPD analysis of the crystalline compound of the title gave the XRPD of FIG. 5.

Example 16

Preparation of Suvorexant from (7-Methyl-1,4-diazepan-1-yl)(5-methyl-2-(2H-1,2,3-triazol-2-yl)phenyl)methanone and 2,5-Dichlorobenzoxazol

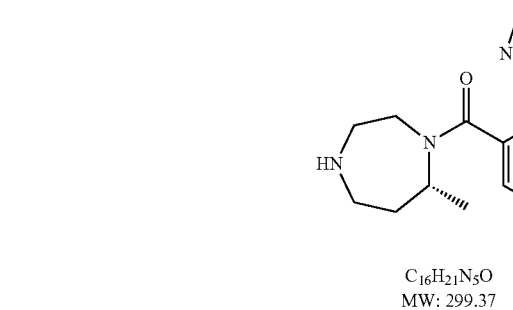

C$_7$H$_4$ClNOS
MW: 185.63

C$_7$H$_3$Cl$_2$NO
MW: 188.01

C$_{16}$H$_{21}$N$_5$O
MW: 299.37

Suvorexant
C$_{23}$H$_{23}$ClN$_6$O$_2$
MW: 450.92

Oxalyl chloride (1.20 g, 9.4 mmol) was added dropwise to a stirred suspension of 2-mercapto-5-chlorobenzoxazol (1.28 g, 6.9 mmol) in CH$_2$Cl$_2$ (37 mL) at <20° C. DMF (4.59 g, 62.8 mmol) was added dropwise. A vigorous gas formation was observed and the suspension turned into a solution halfway throughout the addition. The reaction mixture was stirred for 20 minutes. Two additional aliquots oxalyl chloride (#1:0.20 g, 1.35 mmol; #2:0.40 g, 2.70 mmol) were added and the reaction mixture was stirred for 1.5 hours. HPLC indicated complete conversion of 2-mercapto-5-chlorobenzoxazol into 2,5-Dichlorobenzoxazol.

The solution of 2,5-Dichlorobenzoxazol was added to a solution of (7-Methyl-1,4-diazepan-1-yl)(5-methyl-2-(2H-1,2,3-triazol-2-yl)phenyl)methanone (1.88 g, 6.3 mmol) and NEt$_3$ (3.18 g, 6.3 mmol) in DMF (24 mL) at room temperature. The reaction mixture was then stirred at 70° C. for 19 hours and at 90° C. for 20 hours. The reaction mixture was then cooled to room temperature and quenched with a saturated solution of NaHCO$_3$ (50 mL). The organic phase was separated and washed with H$_2$O (50 mL) followed by brine (50 mL). The organic phase was dried over MgSO$_4$, filtered and concentrated to give crude Suvorexant (3.58 g).

Example 17

Chiral Resolution of a Diazepane (a) Formation of (R)-benzyl 5-methyl-1,4-diazepane-1-carboxylate.DBTA (Compound 12)

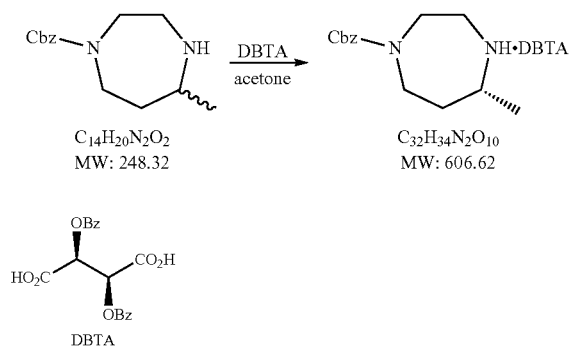

Small Scale

A solution of DBTA (1.48 g, 4.13 mmol) in acetone (6.5 mL) was added to a solution of racemic benzyl 5-methyl-1,4-diazepane-1-carboxylate (1.02 g, 4.11 mmol) and stirred at room temperature. A seeding crystal was added and the crystallization was stirred for 4 hours at room temperature and for 1 hour at 0° C. The solid was filtered, washed with acetone (2.5 mL) and dried in vacuo to give 0.44 g (R)-benzyl 5-methyl-1,4-diazepane-1-carboxylate .DBTA (18% yield) with an enantiomeric ration of e.r.=96.7:3.3.

Large Scale

A solution of DBTA (5.24 g, 14.62 mmol) in acetone (25 mL) was added to a stirred solution of racemic benzyl 5-methyl-1,4-diazepane-1-carboxylate (7.26 g, 29.24 mmol) in acetone (30 mL) at 40° C. The onset of the crystallization occurred after 10 minutes. The crystallization was stirred at 40° C. for 4 hours and at room temperature over night. The solid was filtered, washed twice with acetone (2×8 mL) and dried under reduced pressure (<50 mbar, 45° C.) to give 5.50 g (R)-benzyl 5-methyl-1,4-diazepane-1-carboxylate.DBTA (31% yield) with an enantiomeric ratio of e.r.=88.3:11.7.

(b) Recrystallization of (R)-benzyl 5-methyl-1,4-diazepane-1-carboxylate.DBTA

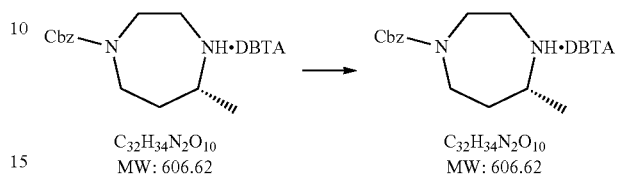

(R)-benzyl 5-methyl-1,4-diazepane-1-carboxylate.DBTA (450 mg, 0.74 mmol) with an enantiomeric ration of e.r.=88.3:11.7 was re-crystallized from EtOH (5 mL) by forming a solution at 60° C. and crystallizing at room temperature. The solid was filtered, washed twice with EtOH (2×2 mL) and dried to give (R)-benzyl 5-methyl-1,4-diazepane-1-carboxylate.DBTA (290 mg, 64% yield) with an enantiomeric ration of e.r.=97.7:2.3.

(c) Isolation of (R)-benzyl 5-methyl-1,4-diazepane-1-carboxylate (Compound (enantio)-4) From (R)-benzyl 5-methyl-1,4-diazepane-1-carboxylate.DBTA

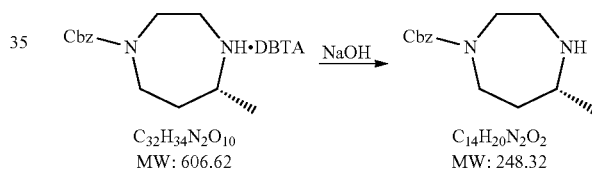

A solution of (R)-benzyl 5-methyl-1,4-diazepane-1-carboxylate.DBTA (2.04 g, 3.36 mmol) in CH$_2$Cl$_2$ (40 mL) was extracted with H$_2$O at pH=12.0 (adjusted with NaOH, 1.0 M). The organic layer was washed twice with H$_2$O (2×20 mL), concentrated under reduced pressure and dried in vacuo to give (R)-benzyl 5-methyl-1,4-diazepane-1-carboxylate (1.02 g, quant. yield).

$^1$H NMR (CDCl$_3$, 300 MHz, hindered rotation is observed): d=7.28-7.36 (m, 5H), 5.13 (m, 2H), 3.54-3.78 (m, 2H), 3.32-3.49 (m, 2H), 3.11 (m~tt, J=13.1, 3.5 Hz, 1H), 2.70-2.87 (m, 2H), 2.08 (br. s, 1H), 1.89 (m, 1H), 1.47 (m, 1H), 1.13 (d, J=5.9 Hz, 1.5H. The analytical data are in full agreement with the analytical data obtained from LKL8-57.

The chirality in (R)-benzyl 5-methyl-1,4-diazepane-1-carboxylate was determined to be R according to the CIP system. The Chirality was determined by protecting the second amine group with Boc$_2$O, by measuring the specific rotation of the product and comparing it to literature values.

Comparative Example 1

Preparation of Suvorexant According to Org. Process Res. Dev. 2011, 15, 367, WO2012/148553

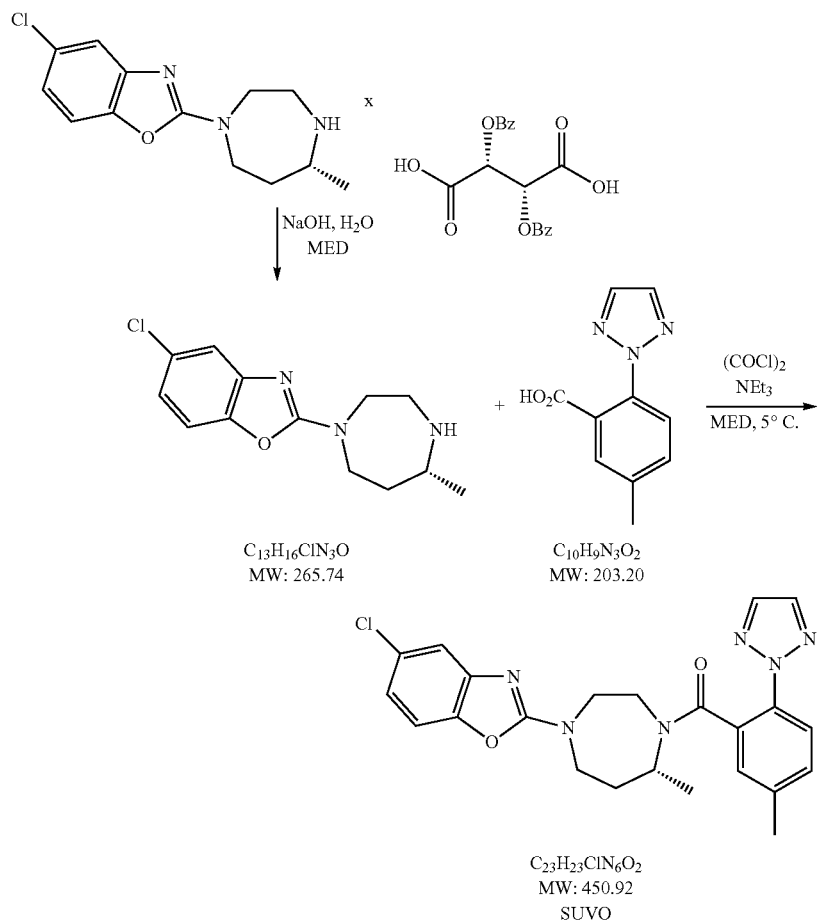

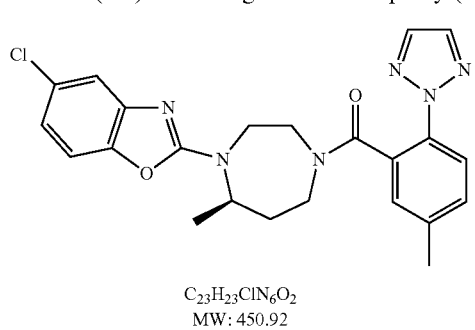

Suvorexant (left) and its regioisomeric impurity (right):

Procedure:

To a solution of the amine. 0.5DBTA salt (4.25 g, 10.0 mmol) in $CH_2Cl_2$ (31 mL) was added a solution of NaOH (10 M solution, 24.6 mL, 246 mmol) in $H_2O$ (40 mL) at room temperature. The heterogeneous mixture was stirred at room temperature for one hour. The two phases were separated. A solution of NaCl (11 g) in $H_2O$ (22 mL) was added to the aqueous phase followed by the addition of $CH_2Cl_2$ (5.5 mL). The heterogeneous mixture was stirred for 10 minutes and the phases were separated. The organic layers were combined and concentrated under reduced pressure to a total volume of approximately 11 mL to give a concentrated solution of the free amine in $CH_2Cl_2$.

Oxalyl chloride (1.08 mL, 10.0 mmol) was added dropwise to a stirred suspension of 5-methyl-2-triazolylbenzoic acid (2.13 g, 10.5 mmol) in $CH_2Cl_2$ (14 mL) and DMF (0.22 mL) at 0° C.-2° C. and the resulting acid chloride solution was stirred for 30 minutes.

$NEt_3$ (2.9 mL, 21 mmol) was added to the solution of the free amine in $CH_2Cl_2$ (total volume approximately 11 mL). The amine solution was then added over a period of 30 minutes to a stirred solution of the acid chloride (total volume approximately 14 mL) at a rate to keep the internal temperature at 5° C.-10° C. The reaction mixture was stirred for one hour before being quenched by the addition of $H_2O$ (27 mL) at a rate to keep the internal temperature <15° C. The two layers were separated and the organic phase was concentrated under reduced pressure to a total volume of approximately 15 mL. Acetonitrile (90 mL) was added followed by the addition of activated charcoal (0.4 g) and the suspension was stirred for 80 minutes at room temperature. The suspension was filtered, the solid was washed with acetonitrile and the solution was concentrated under reduced pressure to a total volume of approximately 18 mL. H$_2$O was added to the solution over a period of 40 minutes at 25° C. The solution was stirred over night. A white precipitate formed during that period. The solid was filtered, washed twice with acetonitrile/H$_2$O (1:5, 5 mL each), washed with H$_2$O, and dried over night in vacuo at 45° C. to give Suvorexant (3.1 g, 68%) with an assay of 89.3 area % according to HPLC. The assay of the "regioisomer" of Suvorexant was 5.2 area %.

Purification of Suvorexant by Extraction and Crystallization-Procedure:

To a solution of Suvorexant (32.6 g) in MeOH (326 mL), CH$_2$Cl$_2$ (163 mL), and H$_2$O (114 mL) at 45° C. was added NaHCO$_3$ in order to adjust the pH-value to pH=10.0 and the solution was stirred at 45° C. for two hours. CH$_2$Cl$_2$ (640 mL) and H$_2$O (320 mL) was added, the organic layer was separated, and concentrated to a total volume of approximately 120 mL. Acetonitril (720 mL) was added and the solution was concentrated to a total weight of approximately 160 g. H$_2$O (360 mL) was added at room temperature. The solid was filtered, washed with H$_2$O and dried at 45° C. over night to give Suvorexant (29.3 g, 90%) with an assay of 96.7 area % according to HPLC. The assay of the "regioisomer" of Suvorexant was 0.9 area %.

The invention claimed is:

1. A process for the preparation of a compound of formula (A)

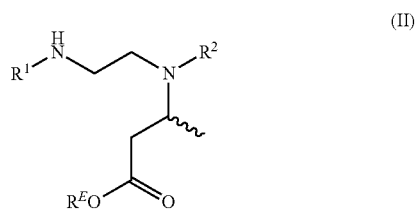

or a pharmaceutically acceptable salt or solvate thereof, wherein R$^1$ is selected from the group consisting of H, PG$^1$ and R$^A$ with R$^A$ being

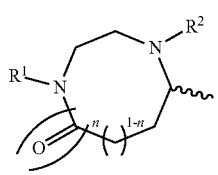

or

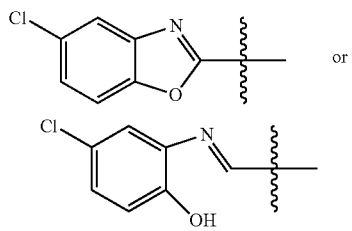

and wherein R$^2$ is selected from the group consisting of H, PG$^2$ and R$^B$ with R$^B$ being

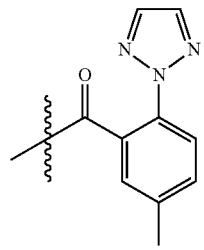 [SMILES: *C(=O)c1cc(C)ccc1-n1nccn1]

and wherein PG$^1$ and PG$^2$ are, independently of each other, suitable protecting groups, and wherein n is 0 or 1, the process comprising (a) providing a compound of formula (II)

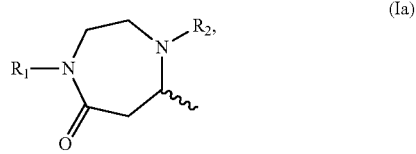

wherein R$^E$ is selected from the group consisting of H, alkyl, aryl, alkylaryl, heteroaryl, cycloalkyl and heterocycloalkyl, (b) reacting the compound of formula (II) with a base and optionally reducing the compound to give the compound of formula (A).

2. The process according to claim 1, wherein the compound of formula (A) has the structure of formula (Ia)

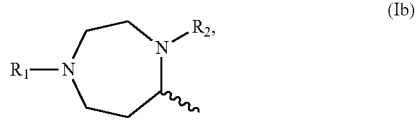

wherein R$^1$ and R$^2$ are as defined in claim 1.

3. The process according to claim 1, wherein the compound of formula (A) has the structure of formula (Ib)

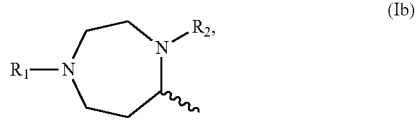

wherein R$^1$ and R$^2$ are as defined in claim 1, wherein in step (b) upon reaction with the base a compound of formula (Ia) is formed,

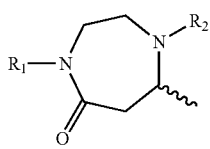
(Ia)

and wherein step (b) further comprises reducing the compound of formula (Ia).

4. The process according to claim 1, wherein the compound of formula (A) has the structure of formula (IX)

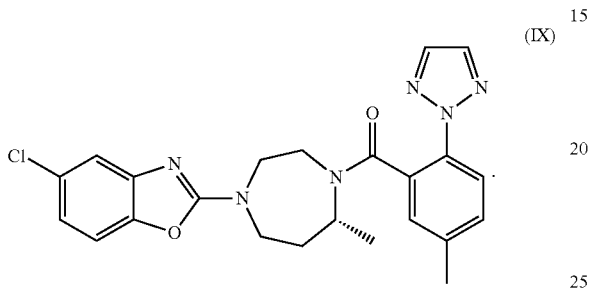
(IX)

5. A process for the preparation of a compound of formula (IX)

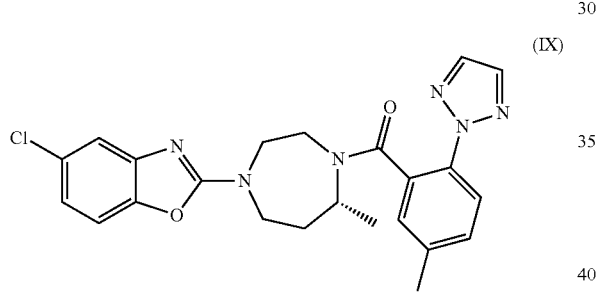
(IX)

comprising (A) preparing a compound of formula (A) according to the method of claim 1, wherein in case n=0, at least one of $R^1$ or $R^2$ is H or a protecting group, (B) transforming the compound of step (A) into the compound of formula (IX).

6. The process of claim 5, wherein step (A) comprises providing a compound of formula (Ia) by a process comprising (a) providing a compound of formula (II)

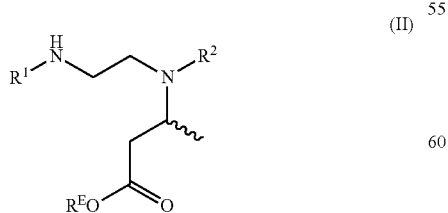
(II)

wherein $R^E$ is selected from the group consisting of H, alkyl, aryl, alkylaryl, heteroaryl, cycloalkyl and heterocycloalkyl, wherein $R^1$ is H and $R^2$ is $PG^2$, (b) reacting the compound of formula (II) with a base, to give the compound of formula (Ia), with $R^1$ being H and with $R^2$ being $PG^2$.

7. The process of claim 5, wherein step (B) comprises
(c1) removal of the protecting group $PG^2$,
(d1) reacting the compound of formula (Ia) with $R^1$ and $R^2$ being H with a compound of formula

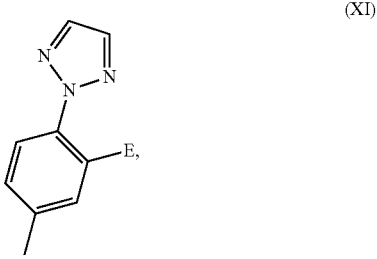
(XI)

wherein E is —COOH or a reactive carboxy group, to give a compound of formula (VIIa), in which $R^1$ is H,

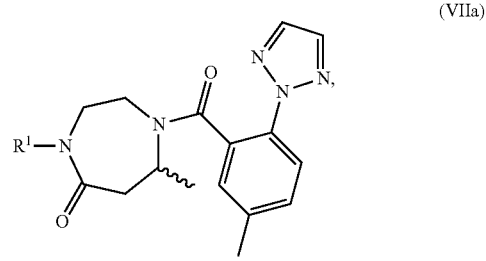
(VIIa)

(e1) reducing the compound, to give a compound of formula (VIIb), in which $R^1$ is H

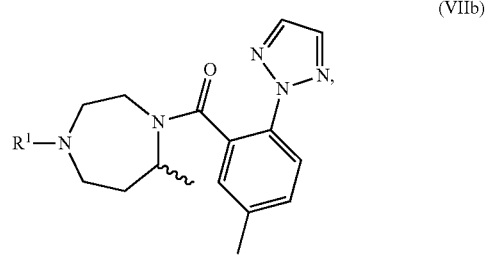
(VIIb)

(f1) reacting the compound of formula (VIIb) with a compound of formula (XII)

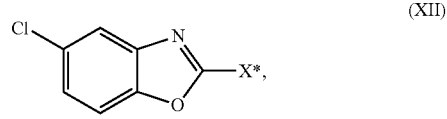
(XII)

wherein X* is a leaving group.

8. The process of claim 7, wherein (e1) comprises
(e1-1) optionally preparing a salt of the compound of formula (VIIb) in which $R^1$ is H,
(e1-2) purifying the compound obtained in (e1) or (e1-1),
(e1-3) optionally transforming the crystalline salt of (e1-2) in the free base of formula (VIIb).

9. Crystalline form (A) of the compound of formula (VIIb-H)

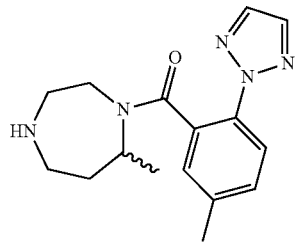
(VIIb-H)

1) having an X-ray powder diffraction pattern comprising a peak at 2-theta angle of approximately 12.4°±0.2°, or at approximately 7.7±0.2°, 11.4°±0.2°, 12.4°±0.2°, 16.2°±0.2° and 18.1°±0.2°, wherein the X-ray powder diffraction pattern is measured at a temperature in the range of from 15 to 25° C. with Cu—K$\alpha_{1,2}$ radiation having a wavelength of 0.15419 nm or 2) having an X-ray powder diffraction pattern comprising a peak at 2-theta angle of approximately 12.4°±0.2°, wherein the X-ray powder diffraction pattern is measured at a temperature in the range of from 15 to 25° C. with Cu—K$\alpha_{1,2}$ radiation having a wavelength of 0.15419 nm.

10. Crystalline form (I) of a compound of formula (VIIb*-H)

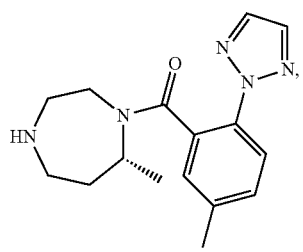
(VIIb*-H)

having an X-ray powder diffraction pattern comprising a peak at 2-theta angle of approximately 11.3°±0.2°, wherein the X-ray powder diffraction pattern is measured at a temperature in the range of from 15 to 25° C. with Cu—K$\alpha_{1,2}$ radiation having a wavelength of 0.15419 nm.

11. Hydrochloride salt of the compound of formula (VIIb) or formula (VIIb*) or (VIIb*)

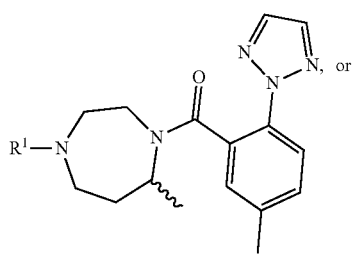
(VIIb)

-continued

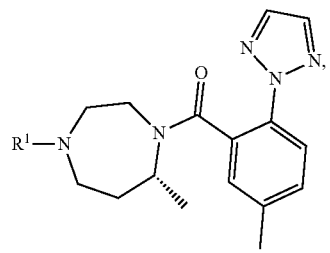
(VIIb*)

wherein R$^1$ is H.

12. The hydrochloride salt of claim 11, wherein the salt is a crystalline form of the hydrochloride salt of formula (VIIb*-Cl)

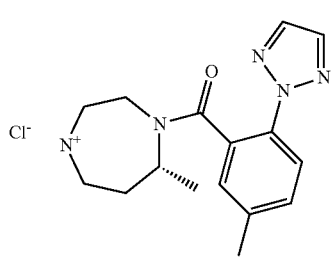
(VIIb*-Cl)

having an X-ray powder diffraction pattern comprising a peak at 2-theta angle of approximately 15.2°±0.2°, wherein the X-ray powder diffraction pattern is measured at a temperature in the range of from 15 to 25° C. with Cu—K$\alpha_{1,2}$ radiation having a wavelength of 0.15419 nm.

13. A compound of formula (IX)

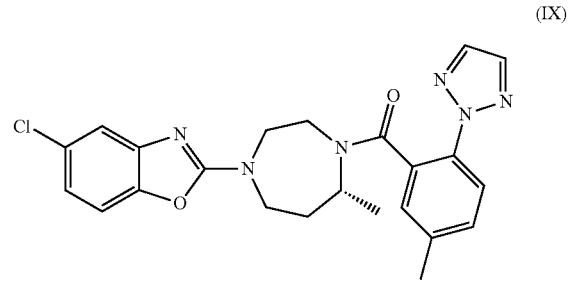 [SMILES: Cc1ccc(-n2nccn2)c(C(=O)N2CCN(c3nc4cc(Cl)ccc4o3)CC[C@H]2C)c1]
(IX)

according to claim 5,
wherein the compound contains less than 5% by weight of the regio-isomeric side product (IX-S) as impurity

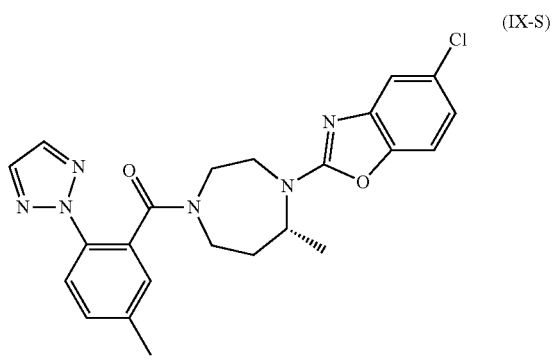 [SMILES: Cc1ccc(-n2nccn2)c(C(=O)N2CC[C@@H](C)N(c3nc4cc(Cl)ccc4o3)CC2)c1]
(IX-S)

based on the total weight of the compound (IX), which includes the compound (IX-S).

14. A compound of formula (A)

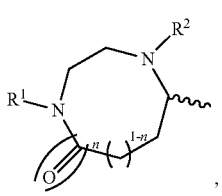

or a pharmaceutically acceptable salt or solvate thereof, wherein R¹ is selected from the group consisting of H, PG¹ and $R^A$ with $R^A$ being

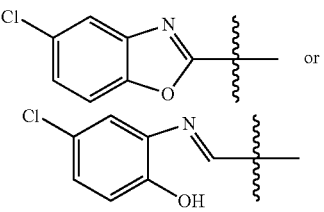

wherein R² is selected from the group consisting of H, PG² and $R^B$ with $R^B$ being

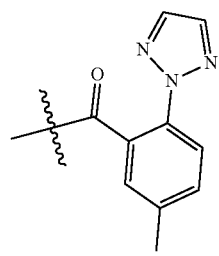 [SMILES: *C(=O)c1cc(C)ccc1-n1nccn1]

wherein PG¹ and PG² are, independently of each other, suitable protecting groups,
wherein n is 0, and
wherein
in case R¹ is $R^A$, R² is not $R^B$ or H
and wherein in case R¹ is H, R² is not $R^B$
and wherein in case R¹ is Cbz, R² is not H or $R^B$
  wherein PG¹ is selected from Boc (t-butyloxycarbonyl), Cbz (carboxybenzyl), Fmoc (Fluorenylmethyloxycarbonyl), benzyl, acetyl, benzoyl, trityl, PNZ (p-nitro benzyloxycarbonyl), Alloc (allyloxycarbonyl), Trifluoroacetate, and Phthalimide, and
  wherein PG² is selected from benzyl, Cbz (carboxybenzyl), PNZ (p-nitrobenzyloxycarbonyl), Alloc (allyloxycarbonyl), Trifluoroacetate, and Phthalimide.

15. A compound of formula (A)

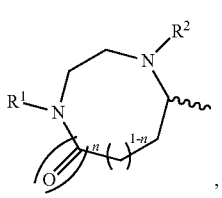

or pharmaceutically acceptable salt or solvate thereof, wherein R¹ is selected from the group consisting of H, PG¹ and $R^A$ with $R^A$ being

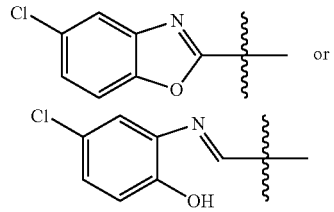

wherein R² is selected from the group consisting of H, PG² and $R^B$ with $R^B$ being

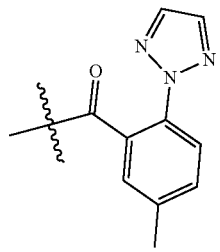 [SMILES: *C(=O)c1cc(C)ccc1-n1nccn1]

wherein PG¹ and PG² are, independently of each other, suitable protecting groups,
wherein n is 1, and wherein when n=1 R¹ and R² are not both H
wherein PG¹ is selected from Boc (t-butyloxycarbonyl), Cbz (carboxybenzyl), Fmoc (Fluorenylmethyloxycarbonyl), benzyl, acetyl, benzoyl, trityl, PNZ (p-nitro benzyloxycarbonyl), Alloc (allyloxycarbonyl), Trifluoroacetate, and Phthalimide, and
wherein PG² is selected from benzyl, Cbz (carboxybenzyl), PNZ (p-nitrobenzyloxycarbonyl), Alloc (allyloxycarbonyl), Trifluoroacetate, and Phthalimide.

16. A process for the preparation of a compound of formula (IX)

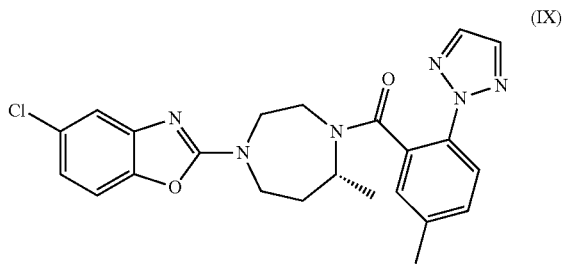 [SMILES: Cc1ccc(-n2nccn2)c(C(=O)N2CCN(c3nc4cc(Cl)ccc4o3)CC[C@H]2C)c1]

comprising
(A) preparing a compound of formula (A) according to the method of claim 1; and
(B) transforming the compound of step (A) into the compound of formula (IX).

* * * * *